US008338467B2

(12) United States Patent
Kolasa et al.

(10) Patent No.: US 8,338,467 B2
(45) Date of Patent: Dec. 25, 2012

(54) COMPOUNDS AS CANNABINOID RECEPTOR LIGANDS

(75) Inventors: Teodozyj Kolasa, Lake Villa, IL (US); Jennifer M. Frost, Grayslake, IL (US); Meena V. Patel, Green Oaks, IL (US); Steven P. Latshaw, Round Lake, IL (US); Arturo Perez-Medrano, Grayslake, IL (US); Xueqing Wang, Evanston, IL (US); Karin Rose Marie Tietje, Mundelein, IL (US); Sridhar Peddi, Grayslake, IL (US); William A. Carroll, Evanston, IL (US)

(73) Assignee: AbbVie Inc., North Chicago, IL (US)

( * ) Notice: Subject to any disclaimer, the term of this patent is extended or adjusted under 35 U.S.C. 154(b) by 0 days.

(21) Appl. No.: 13/245,187

(22) Filed: Sep. 26, 2011

(65) Prior Publication Data

US 2012/0015929 A1    Jan. 19, 2012

Related U.S. Application Data

(62) Division of application No. 12/401,788, filed on Mar. 11, 2009, now Pat. No. 8,058,293.

(60) Provisional application No. 61/035,632, filed on Mar. 11, 2008.

(51) Int. Cl.
    A61K 31/426    (2006.01)
    C07D 277/18    (2006.01)
(52) U.S. Cl. .......................... 514/370; 514/371; 548/195
(58) Field of Classification Search .................. 514/370, 514/371; 548/195
    See application file for complete search history.

(56) References Cited

U.S. PATENT DOCUMENTS

| | | | |
|---|---|---|---|
| 5,468,722 A | 11/1995 | Shibata et al. |
| 5,654,322 A | 8/1997 | Hirata et al. |
| 6,559,186 B1 | 5/2003 | Campbell |
| 7,511,013 B2 | 3/2009 | Molino et al. |
| 7,514,068 B2 | 4/2009 | Tung |
| 7,521,421 B2 | 4/2009 | Naicker et al. |
| 7,528,131 B2 | 5/2009 | Persichetti et al. |
| 7,531,685 B2 | 5/2009 | Czarnik |
| 7,534,814 B2 | 5/2009 | Ascher et al. |
| 7,538,189 B2 | 5/2009 | Naicker et al. |
| 7,560,456 B2 | 7/2009 | Araki et al. |
| 7,674,912 B2 | 3/2010 | Sams et al. |
| 7,683,084 B2 | 3/2010 | Faghih et al. |
| 7,872,006 B2 | 1/2011 | Moritani et al. |
| 7,872,033 B2 | 1/2011 | Carroll et al. |
| 7,875,639 B2 | 1/2011 | Florjancic et al. |
| 7,875,640 B2 | 1/2011 | Kolasa et al. |
| 2004/0259912 A1 | 12/2004 | Matsumoto et al. |
| 2006/0199817 A1 | 9/2006 | Tasker et al. |
| 2008/0058335 A1 | 3/2008 | Florjancic et al. |
| 2008/0058355 A1 | 3/2008 | Westheim |
| 2008/0242654 A1 | 10/2008 | Kolasa et al. |
| 2008/0287510 A1 | 11/2008 | Carroll et al. |
| 2008/0312435 A1 | 12/2008 | Saito et al. |
| 2009/0082471 A1 | 3/2009 | Czarnik |
| 2009/0088416 A1 | 4/2009 | Czarnik |
| 2009/0093422 A1 | 4/2009 | Tung et al. |
| 2009/0105147 A1 | 4/2009 | Masse |
| 2009/0105305 A1 | 4/2009 | Butlin et al. |
| 2009/0105307 A1 | 4/2009 | Galley et al. |
| 2009/0105338 A1 | 4/2009 | Czarnik |
| 2009/0111840 A1 | 4/2009 | Herold et al. |
| 2009/0118238 A1 | 5/2009 | Czarnik |
| 2009/0131363 A1 | 5/2009 | Harbeson |
| 2009/0131485 A1 | 5/2009 | Liu et al. |
| 2009/0137457 A1 | 5/2009 | Harbeson |
| 2010/0041720 A1 | 2/2010 | Carroll et al. |
| 2010/0063022 A1 | 3/2010 | Carroll et al. |
| 2010/0069348 A1 | 3/2010 | Carroll et al. |
| 2010/0069349 A1 | 3/2010 | Carroll et al. |
| 2010/0093814 A1 | 4/2010 | Florjancic et al. |
| 2010/0216760 A1 | 8/2010 | Frost et al. |

FOREIGN PATENT DOCUMENTS

| | | |
|---|---|---|
| CA | 2587667 A1 | 5/2006 |
| DE | 3533331 A1 | 3/1987 |
| EP | 412404 A2 | 2/1991 |
| EP | 568096 A1 | 11/1993 |
| EP | 1219612 A1 | 7/2002 |
| EP | 1820504 A1 | 8/2007 |
| FR | 2796643 A1 | 1/2001 |

(Continued)

OTHER PUBLICATIONS

Abreo, et al., "Novel 3-Pyridyl Ethers with Subnanomolar Affinity for Central Neuronal Nicotonic Acetylcholine Receptors," Journal of Medicinal Chemistry, 1996, vol. 39 (4), pp. 817-825.

(Continued)

*Primary Examiner* — Yong Chu

(74) *Attorney, Agent, or Firm* — Nancy J. Gettel

(57) ABSTRACT

Disclosed herein are compounds of formula (I)

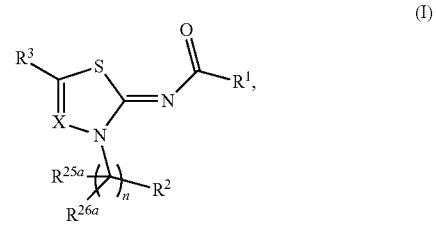

wherein $R^1$, $R^2$, $R^3$, $R^{25a}$, $R^{26a}$, X, and n are as defined in the specification. Pharmaceutical compositions comprising such compounds, and methods of treating conditions and disorders using such compounds and pharmaceutical compositions are also described.

13 Claims, No Drawings

FOREIGN PATENT DOCUMENTS

| WO | WO9507271 A1 | 3/1995 |
|---|---|---|
| WO | WO9710223 A1 | 3/1997 |
| WO | WO02102232 A2 | 12/2002 |
| WO | WO2005058887 A1 | 6/2005 |
| WO | WO2005099353 A2 | 10/2005 |
| WO | WO2006008754 A1 | 1/2006 |
| WO | WO2006051704 A1 | 5/2006 |
| WO | WO2006100208 A1 | 9/2006 |
| WO | WO 2007140385 A2 * | 12/2007 |
| WO | WO2007140385 A2 | 12/2007 |
| WO | WO2007140385 A3 | 12/2007 |
| WO | WO2007140439 A2 | 12/2007 |
| WO | WO2007140439 A3 | 12/2007 |
| WO | WO2008079687 A1 | 7/2008 |
| WO | WO2008121558 A1 | 10/2008 |
| WO | WO2008130953 A2 | 10/2008 |
| WO | WO2008144360 A1 | 11/2008 |
| WO | WO2009048936 A1 | 4/2009 |
| WO | WO2009067613 A1 | 5/2009 |
| WO | WO2009114566 A1 | 9/2009 |
| WO | WO2010019547 A1 | 2/2010 |

OTHER PUBLICATIONS

Ambartsumova, et al., "Effect of Various Factors on the Reaction of 2-Aminobenzothiazoles with Propylene Oxide," Chemistry of Heterocyclic Compounds, 2002, vol. 38 (8), pp. 994-999.

Araki, et al., (2003): STN International HCAPLUS database, (Columbus, OH). Accession No. 2003-931334.

Arevalo-Martin, et al., "Therapeutic Action of Cannabinoids in a Murine Model of Multiple Sclerosis," Journal of Neuroscience, 2003, vol. 23 (7), pp. 2511-2516.

Baker, et al., "Regiospecific Vinyl Phosphate/β-Keto Phosphonate Rearrangements Initiated by Halogen-Metal Exchange," Journal of Organic Chemistry, 1998, vol. 63 (8), pp. 2613-2618.

Benito, et al., "A Glial Endogenous Cannabinoid System is Upregulated in the Brains of Macaques with Simian Immunodeficiency Virus-Induced Encephalitis," Journal of Neuroscience, 2005, vol. 25 (10), pp. 2530-2536.

Benito, et al., "Cannabinoid $CB_2$ Receptors and Fatty Acid Amide Hydrolase are Selectively Overexpressed in Neuritic Plaque-Associated Glia in Alzheimer's Disease Brains," Journal of Neuroscience, 2003, vol. 23 (35), pp. 11136-11141.

Bennett, et al., "A Peripheral Mononeuropathy in Rat that Produces Disorders of Pain Sensation like those Seen in Man," Pain, 1988, vol. 33 (1), pp. 87-107.

Berge, et al., "Pharmaceutical Salts," Journal of Pharmaceutical Sciences, 1977, vol. 66 (1), pp. 1-19.

Beylot, et al., "In Vivo Studies of Intrahepatic Metabolic Pathways," Diabetes Metabolism, 1997, vol. 23 (3), pp. 251-257.

Blagojevic, et al., "Role of heavy water in Boron Neutron Capture Therapy," Topics in Dosimetry & Treatment Planning for Neutron Capture Therapy, 1994, pp. 125-134.

Blake, et al., "Studies With Deuterated Drugs," Journal of Pharmaceutical Sciences, 1975, vol. 64 (3), pp. 367-391.

Bouchard, et al., "Contribution of Endocannabinoids in the Endothelial Protection Afforded by Ischemic Preconditioning in the Isolated Rat Heart," Life Sciences, 2003, vol. 72 (16), pp. 1859-1870.

Boyle, et al., "Osteoclast Differentiation and Activation," Nature, 2003, vol. 423 (6937), pp. 337-342.

Bozidar, et al., "Transformations of 1,2,4-Thiadiazolo/2,3-X/ Azines," Heterocycles, 1987, vol. 26 (3), pp. 689-697.

Bozidar, et al., "Transformations of 1-(2-Chloropyridyl-3)-4-ethoxycarbonyland 1-(2-Chloropyridyl-3)-4-ethoxycarbonylmethyl Thiosemicarbazides. Attempts to Prepare Pyrido [3,2-e]-1,2,4-thiadiazine," Monatshefte Fur Chemie, 1988, vol. 119, pp. 333-339.

Brennan, et al., "Characterization of a Rat Model of Incisional Pain," Pain, 1996, vol. 64, pp. 493-501.

Brickner, et al., "Synthesis and Antibacterial Activity of U-100592 and U-100766, Two Oxazolidinone Antibacterial Agents for the Potential Treatment of Multidrug-Resistant Gram-Positive Bacterial Infections," Journal of Medicinal Chemistry, 1996, vol. 39 (3), pp. 673-679.

Buckley, et al., "Immunomodulation by Cannabinoids is Absent in Mice Deficient for the Cannabinoid $CB_2$ Receptor," European Journal of Pharmacology, 2000, vol. 396, pp. 141-149.

CAPLUS Record of U.S. Patent Application Publication No. 2008/0058335 by Westheim et al., 2007.

CAPLUS Record of U.S. Patent Application Publication No. 2008/0242654 by Kolasa et al., 2008.

Carlisle, et al., "Differential Expression of the $CB_2$ Cannabinoid Receptor by Rodent Macrophages and Macrophage-like Cells in Relation to Cell Activation," International Immunopharmacology, 2002, vol. 2, pp. 69.

Carrier, et al., "Endocannabinoids in Neuroimmunology and Stress," Current Drug Targets—CNS and Neurological Disorders, 2005, vol. 4, pp. 657-665.

Casanova, et al , "Inhibition of Skin Tumor Growth and Angiogenesis in vivo by Activation of Cannabinoid Receptors," Journal of Clinical Investigation, 2003, vol. 111 (1), pp. 43-50.

Chaplan, et al., "Quantitative Assessment of Tactile Allodynia in the Rat Paw," Journal of Neuroscience Methods, 1994, vol. 53, pp. 55-63.

Cichewicz, D., "Synergistic Interactions Between Cannabinoid and Opioid Analgesics," Life Sciences, 2004, vol. 74 (11), pp. 1317-1324.

Clayton, et al., "CB1 and CB2 Cannabinoid Receptors are Implicated in Inflammatory Pain," Pain, 2002, vol. 96 (3), pp. 253-260.

Cotarca, et al., "Bis (trichloromethyl) Carbonate in Organic Synthesis," 1996, vol. 6, pp. 553-576.

Cross, et al., "IUPAC Commission on Nomenclature of Organic Chemistry: Rules for the Nomenclature of Organic Chemistry, Section E: Stereochemistry," Pure and Applied Chemistry, 1976, vol. 45, pp. 13-30.

Czajka, et al., "Effect of Deuterium Oxide on the Reproductive Potential of Mice," Annals of the New York Academy of Sciences, 1960, vol. 84, pp. 770-779.

Czajka, et al., "Physiological Effects of Deuterium on Dogs," American Journal of Physiology, 1961, vol. 201 (2), pp. 357-362.

Dart, et al (2007): STN International HCAPLUS database, Columbus (OH), Accession No. 2007:1396538.

Dixon, W., "Efficient Analysis of Experimental Observations," Annual Review of Pharmacology and Toxicology, 1980, vol. 20, pp. 441-462.

Eckert, et al., "Triphosgene, a Crystalline Phosgene Substitute," Angewandte Chemie International Edition in English, 1987, vol. 26 (9), pp. 894-895.

Filippo, et al., "Cannabinoid CB2 Receptor Activation Reduces Mouse Myocardial Ischemia-Reperfusion Injury: Involvement of Cytokine/Chemokines and PMN," Journal of Leukocyte Biology, 2004, vol. 75 (3), pp. 453-459.

Final Office Action mailed Mar. 10, 2010 for U.S. Appl. No. 11/755,434, filed May 30, 2007.

Final Office Action mailed Sep. 14, 2011 for U.S. Appl. No. 12/274,105, filed Nov. 19, 2008.

Final Office Action mailed Feb. 15, 2011 for U.S. Appl. No. 12/120,969, filed May 15, 2008.

Final Office Action mailed Nov. 16, 2011 for U.S. Appl. No. 12/554,445, filed Sep. 4, 2009.

Final Office Action mailed Nov. 16, 2011 for U.S. Appl. No. 12/560,897, filed Sep. 16, 2009.

Final Office Action mailed Apr. 19, 2011 for U.S. Appl. No. 12/539,120, filed Aug. 11, 2009.

Final Office Action mailed Oct. 19, 2011 for U.S. Appl. No. 12/560,893, filed Sep. 16, 2009.

Final Office Action mailed Mar. 24, 2011 for U.S. Appl. No. 11/755,434, filed May 30, 2007.

Final Office Action mailed Dec. 28, 2011 for U.S. Appl. No. 12/639,173, filed Dec. 16, 2009.

Florancic, et al., (2009): Caplus Entry for WO2009067613, Accession No. 2009:649814.

Florancic, et al., (2010): STN International HCAPLUS database, Columbus (OH), Accession NO. 2010:478868.

Foster, et al., "Deuterium Isotope Effects in the Metabolism of Drugs and Xenobiotics: Implications for Drug Design," Advances in Drug Research, 1985, vol. 14, pp. 2-36.

Galiégue, et al., "Expression of Central and Peripheral Cannabinoid Receptors in Human Immune Tissues and Leukocyte Subpopulations," European Journal of Biochemistry, 1995, vol. 232 (1), pp. 54-61.

Giron, D., "Applications of Thermal Analysis and Coupled Techniques in Pharmaceutical Industry," Journal of Thermal Analysis and Calorimetry, 2002, vol. 68, pp. 335-357.

Giron, D., "Investigations of Polymorphism and Pseudo-Polymorphism in Pharmaceuticals by Combined Thermoanalytical Techniques," The Journal of Thermal Analysis and Calorimetry, 2001, vol. 64, pp. 37-60.

Golech, et al., "Human Brain Endothelium: Coexpression and Function of Vannilloid and Endocannabinoid Receptors," Molecular Brain Research, 2004, vol. 132 (1), pp. 87-92.

Golub, et al., "Molecular Classification of Cancer: Class Discovery and Class Prediction by Gene Expression Monitoring," Science, 1999, vol. 286 (5439), pp. 531-537.

Gouldson, et al., "Mutational Analysis and Molecular Modeling of the Antagonist SR144528 Binding Site on the Human Cannabinoid $CB_2$ Receptor; Figures 4 and 5," European Journal of Pharmacology, 2000, vol. 401 (1), pp. 17-25.

Greene, et al., "Protection for the Amino group," Protective Groups in Organic Synthesis, 1999, Third Edition, pp. 494-653.

Greene, et al., Protective Groups in Organic Synthesis, 3rd Edition, John Wiley and Sons, Inc., 1999, Table of Contents.

Groteniiermen, et al., "IACM $2^{nd}$ Conference on Cannabinoids in Medicine," Expert Opinion in Pharmacotherapy, 2003, vol. 4 (12), pp. 2367-2371.

Hamuro, et al., "Solid-Phase Synthesis of Acyclic and Cyclic Amino Acid Derived Urea Peptidomimetics Using Phoxime Resin," The Journal of Combinatorial Chemistry, 1999, vol. 1, pp. 163-172.

Hanus, et al., "HU-308: A Specific Agonist for $CB_2$, a Peripheral Cannabinoid Receptor," Proceedings of the National Academy of Science, 1999, vol. 96, pp. 14228-14233.

Hargreaves, et al., "A New and Sensitive Method for Measuring Thermal Nociception in Cutaneous Hyperalgesia," Pain, 1988. 32 (1), pp. 77-88.

Hohmann, et al., "Selective Activation of Cannabinoid $CB_2$ Receptors Suppresses Hyperalgesia Evoked by Intradermal Capsaicin," Journal of Pharmacology and Experimental Therapeutics, 2004, vol. 308, pp. 446-453.

Hutchins, et al., "A General Method for the Solid Phase Synthesis of Ureas," Tetrahedron Letters, 1994, vol. 35 (24), pp. 4055-4058.

Hutchins, et al., "A Strategy for Urea Linked Diamine Libraries," Tetrahedron Letters, 1995, vol. 36 (15), pp. 2583-2586.

Ibrahim, et al., "Activation of $CB_2$ Cannabinoid Receptors by AM1241 Inhibits Experimental Neuropathic Pain: Pain Inhibition by Receptors not Present in the CNS," Proceedings of the National Academy of Science, 2003, vol. 100 (18), pp. 10529-10533.

Ibrahim, et al., "$CB_2$ Cannabinoid Receptor Activation Produces Antinociception by Stimulating Peripheral Release of Endogenous Opioids," Proceedings of the National Academy of Science, 2005, vol. 102 (8), pp. 3093-3098.

Idris, et al., "Regulation of Bone Mass, Bone Loss and Osteoclast Activity by Cannabinoid Receptors," Nature Medicine, 2005, vol. 11 (7), pp. 774-779.

Ihenetu, et al, "Inhibition of Interleukin-8 Release in the Human Colonic Epithelial Cell Linc HT-29 by Cannabinoids," European Journal of Pharmacology, 2003, vol. 458 (1-2), pp. 207-215.

International Search Report and Written Opinion for Application No. PCT/US2009/036715, mailed on Jun. 10, 2009, 9 pages.

International Search Report for Application No. PCT/US07/069921, mailed on Nov. 27, 2007, 4 pages.

International Search Report for Application No. PCT/US08/063648, mailed on Aug. 13, 2008, 3 pages.

International Search Report for Application No. PCT/US08/079182, mailed on Dec. 15, 2008, 2 pages.

International Search Report for Application No. PCT/US2009/053369, mailed on Oct. 22, 2009, 3 pages.

International Search Report for Application No. PCT/US2009/056179, mailed on Jun. 9, 2010, 4 pages.

International Search Report for Application No. PCT/US2009/057088, mailed on Oct. 5, 2010, 4 pages.

International Search Report for Application No. PCT/US2009/068173, mailed on Feb. 5, 2010, 3 pages.

Izdebski, et al., "A New Convenient Method for the Synthesis of Symmetrical and Unsymmetrical N,N'-Disubstituted Ureas," Synthesis, 1989, pp. 423-425.

Jain, et al., "The Synthesis and Antimicrobial Screening of Some Novel Aza-Imidoxy Compounds as Potential Chemotherapeutic Agents," Phosphorus Sulfur and Silicon, 2006, vol. 181 (7), pp. 1665-1673.

Joshi, et al., "Comparison of Antinociceptive Actoins of Standard Analgesics in Attenuating Capsaicin and Nerve-Injury-Induced Mechanical Hypersensitivity," Neuroscience, 2006, vol. 143, pp. 587-596.

Julien, et al., "Antifibrogenic Role of the Cannabinoid Receptor $CB_2$ in the Liver," Gastroenterology, 2005, vol. 128, pp. 742-755.

Karsak, et al., "Cannabinoid Receptor Type 2 Gene is Associated with Human Osteoporosis," Human Molecular Genetics, 2005, vol. 14 (22), pp. 3389-3396.

Kato, et al., "Synthesis of Deuterated Mosapride Citrate," Journal of Labelled Compounds and Radiopharmaceuticals, 1995, vol. 36 (10), pp. 927-932.

Katritzky, et al., "A General Synthesis of Unsymmetrical Tetrasubstituted Ureas," Journal of Organic Chemistry, 1997, vol. 62 (11), pp. 4155-4158.

Kim, et al., "An Experimental Model for Peripheral Neuropathy Produced by Segmental Spinal Nerve Ligation in the Rat," Pain, 1992, vol. 50 (3), pp. 355-363.

Knolker, et al., "A Novel Method for the Synthesis of Isocyanates Under Mild Conditions," Angewandte Chemie International Edition in English, 1995, vol. 34 (22), pp. 2497-2500.

Knolker, et al., "Synthesis of Symmetrical and Unsymmetrical Ureas by DMAP-Catalyzed Reaction of Alkyl- and Arylamines with Di-tert-butyldicarbonate," Synlett, 1996, pp. 502-504.

Kolasa, "Thiazolylidene Derivatives as Cannabinoid Receptor Ligands and Their Preparation" Accession No. 2008:1184581, Mar. 22, 2011.

Kreutzberg, et al., "Microglia: A Sensor for Pathological Events in the CNS," Trends in Neuroscience, 1996, vol. 19, pp. 312-318.

Kruijtzer et al., "Approaches to the Synthesis of Ureapeptoid Peptidotnimetics," Tetrahedron Letters, 1997, vol. 38 (30), pp. 5335-5338.

Kushner, et al., "Pharmacological uses and perspectives of heavy water and deuterated compounds," Canadian Journal of Physiology and Pharmacology, 1999, vol. 77 (2), pp. 79-88.

Lamothe et al., "A Simple One-Pot Preparation of N,N'-unsymmetrical ureas from N-Boc Protected Primary Anilines and Amines," Synlett, 1996, vol. 6, pp. 507-508.

Lemoucheux, et al., "Debenzylation of Tertiary Amines Using Phosgene or Triphosgene: An Efficient and Rapid Procedure for the Preparation of Carbamoyl Chlorides and Unsymmetrical Ureas. Application in Carbon-11 Chemistry," Journal of Organic Chemistry, 2003, vol. 68 (19), pp. 7289-7297.

Lepicier, et al., "Endocannabinoids Protect the Rat Isolated Heart Against Ischaemia," British Journal of Pharmacology, 2003, vol. 139, pp. 805-815.

Leung, et al., "S,S-Dimethyl Dithiocarbonate: A Convenient Reagent for the Synthesis of Symmetrical and Unsymmetrical Ureas," Journal of Organic Chemistry, 1996, vol. 61 (12), pp. 4175-4179.

Li, et al., "An Improved Synthesis of Pyran-3,5-Dione: Application to the Synthesis of Abt-598, A Potassium Channel Opener, Via Hantzsch Reaction," Journal of Organic Chemistry, 2006, vol. 71 (4), pp. 1725-1727.

Lizondo, et al., "Linezolid: Oxazolidinone antibacterial," Drugs of the Future, 1996, vol. 21 (11), pp. 1116-1123.

Lotersztajn, et al., "Hepatic Fibrosis: Molecular Mechanisms and Drug Targets," Annual Review of Pharmacology and Toxicology, 2005, vol. 45, pp. 605-628.

Majer, et al., "A Safe and Efficient Method for Preparation of N,"-Unsymmetrically Disubstituted Ureas Utilizing Triphosgene," Journal of Organic Chemistry, 1994, vol. 59, pp. 1937-1938.

Malan, et al., "$CB_2$ Cannabinoid Receptor-Mediated Peripheral Antinociception," Pain, 2001, vol. 93, pp. 239-245.

Maligres, et al., "Stereocontrolled Preparation of a Nonpeptidal (-)-Spirobicyclic NK-1 Receptor Antagonist," Journal of Organic Chemistry, 2002, vol. 67 (4), pp. 1093-1101.

Mallesham, et al., "Highly Efficient Cul-Catalyzed Coupling of Aryl Bromides With Oxazolidinones Using Buchwald's Protocol: A Short Route to Linezolid and Toloxatone," Organic Letters, 2003, vol. 5 (7), pp. 963-965.

Manaka, et al., "2-Acylimino-3H-thiazoline Derivatives: A Novel Template for Platelet GPIIb/IIIa Receptor Antagonists," Bioorganic & Medicinal Chemistry Letters, 2001, vol. 11, pp. 1031-1035.

Maresz, et al., "Modulation of the Cannabinoid $CB_2$ Receptor in Microglial Cells in Response to Inflammatory Stimuli," Journal of Neurochemistry, 2005, vol. 95, pp. 437-445.

Mathison, et al., "Effects of Cannabinoid Receptor-2 Activation on Accelerated Gastrointestinal Transit in Lipopolysaccharide-Treated Rats," British Journal of Pharmacology, 2004, vol. 142, pp. 1247-1254.

McKallip, et al., "Targeting $CB_2$ Cannabinoid Receptors as a Novel Therapy to Treat Malignant Lymphoblastic Disease," Blood, 2002, vol. 15 (2), pp. 627-634.

Miyaura, et al., ed., Topics in Current Chemistry: Cross-Coupling Reactions, Springer, 2002, Table of Contents.

Molina-Holgado, et al., "Endogenous Interleukin-1 Receptor Antagonist Mediates Anti-Inflammatory and Neuroprotective Actions of Cannabinoids in Neurons and Glia," Journal of Neuroscience, 2003, vol. 23 (16), pp. 6470-6474.

Nackley, et al., "Selective Activation of Cannabinoid $CB_2$ Receptors Suppresses Spinal fos Protein Expression and Pain Behavior in a Rat Model of Inflammation," Neuroscience, 2003, vol. 119, pp. 747-757.

Negishi, et al., eds., Handbook of Organopalladium Chemistry for Organic Synthesis, vol. 1, John Wiley & Sons, 2002, Table of Contents.

Ni, et al., "Win 55212-2, a Cannabinoid Receptor Agonist, Attenuates Leukocyte/Endothelial Interactions in an Experimental Autoimmune Encephalomyelitis Model," Multiple Sclerosis, 2004, vol. 10, pp. 158-164.

Nieuwenhuijzen, et al., "Solid and Solution Phase Combinatorial Synthesis of Ureas," Tetrahedron Letters, 1998, vol. 39, pp. 7811-7814.

Non-Final Office Action mailed Jun. 1, 2011 for U.S. Appl. No. 12/554,445, filed Sep. 4, 2009.

Non-Final Office Action mailed Jun. 1, 2011 for U.S. Appl. No. 12/560,897, filed Sep. 16, 2009.

Non-Final Office Action mailed Jun. 2, 2009 for U.S. Appl. No. 11/755,434, filed May 30, 2007.

Non-Final Office Action mailed Sep. 7, 2010 for U.S. Appl. No. 12/120,969 filed May 15, 2008.

Non-Final Office Action mailed Jan. 12, 2010 for U.S. Appl. No. 12/120,969, filed May 15, 2008.

Non-Final Office Action mailed May 17, 2011 for U.S. Appl. No. 12/560,893, filed Sep. 16, 2009.

Non-Final Office Action mailed Aug. 23, 2011 for U.S. Appl. No. 12/639,173, filed Dec. 16, 2009.

Non-Final Office Action mailed Jan. 27, 2011 for US. Appl. No. 12/274,105, filed Nov. 19, 2008.

Non-Final Office Action mailed Jun. 29, 2010 for U.S. Appl. No. 11/755,434, filed May 30, 2007.

Non-Final Office Action mailed Nov. 30, 2010 for U.S. Appl. No. 11/755,434, filed May 30, 2007.

Nunez, et al., "Cannabinoid $CB_2$ Receptors Are Expressed by Perivascular Microglial Cells in the Human Brain: An Immunohistochemical Study," Synapse, 2004, vol. 53, pp. 208-213.

Ohta, et al., "Imine Derivatives as new Potent and Selective $CB_2$ Cannabinoid Receptor agonist with an Analgesic Action," Bioorganic and Medicinal Chemistry, 2007, vol. 16 (3), pp. 1111-1124.

Ohta, et al., "N-Alkyidenearylcarboxamides as a new Potent and Selective $CB_2$ Cannabinoid Receptor Agonist with an Analgesic Action," Bioorganic and Medicinal Chemistry Letters, 2007, vol. 17 (22), pp. 6299-6304.

Opposition filed by "Asociacion de Industrias Farmaceuticas Dominicanas Inc" for the Dominican Patent application Nr P2008-0060, received on Apr. 1, 2009, 8 pages.

Patel, et al , "Inhibition of Guinea-Pig and Human Sensory Nerve Activity and the Cough Reflex in Guinea-Pigs by Cannabinoid ($CB_2$) Receptor Activation," British Journal of Pharmacology, 2003, vol. 140 (2), pp. 261-268.

Pertwee, R., "Cannabinoids and Multiple Sclerosis," Pharmacology & Therapeutics, 2002, vol. 95, pp. 165-174.

Poste, et al., "Lipid Vesicles as Carriers for Introducing Biologically Active Materials into Cells," Methods in Cell Biology, 1976, vol. 14, pp. 33-71.

Quartilho, et al., "Inhibition of Inflammatory Hyperalgesia by Activation of Peripheral $CB_2$ Cannabinoid Receptors," Anesthesiology, 2003, vol. 99, pp. 955-960.

Radulescu, et al., "Actes Du Colloque Franco-Roumain De Chimie Appliquee, 3Rd, Bacau, Romania," 2004, pp. 117-120.

Radulescu, et al., "The Comparative Study on the Synthesis Methods of a Heterocyclic System 2-Aminothiazolo[4,5-13]Pyricline," Revista de Chimie, 2005, vol. 56 (6), pp. 659-662.

Radulescu, et al., "Synthesis and Characteristics of Compact Condensed Heterocyclic System 2-Aminothiazolo[5,4-c]Pyridine," Revista de Chimie, 2004, vol. 55 (11), pp. 889-893.

Ralston, S., "Genetic Determinants of Susceptibility to Osteoporosis," Current Opinion in Pharmacology, 2003, vol. 3, pp. 286-290.

Ramirez, et al., "Prevention of Alzheimers Disease Pathology by Cannabinoids: Neuroprotection Mediated by Blockade of Microglial Activation," Journal of Neuroscience, 2005, vol. 25 (8), pp. 1904-1913.

Rautio, et al, "Prodrugs: Design and Clinical Applications," Nature Reviews Drug Discovery, 2008, vol. 7 (3), pp. 255-270.

Rodriquez-Spong, et al., "General Principles of Pharmaceutical Solid Polymorphism: A Supramolecular Perspective," Advanced Drug Delivery Reviews, 2004, vol. 56 (3), pp. 241-274.

Ross, et al., "Antianaphylactic agents. 1. 2-(Acylamino)oxazoles," Journal of Medicinal Chemistry, 1979, vol. 22(4), pp. 412-417.

Sanchez, et al., "Inhibition of Glioma Growth in Vivo by Selective Activation of the $CB_2$ Cannabinoid Receptor1," Cancer Research, 2001, vol. 61, pp. 5784-5789.

Scialdone, et al., "Phosgenated p-nitrophenyl(polystyrene)ketoxime or phoxime resin. A new resin for the solid-phase synthesis of ureas via thermolytic cleavage of oxime-carbamates", Journal of Organic Chemistry, 1998, vol. 63, pp. 4802-4807.

Smith, D., "Do Prodrugs Deliver", Current Opinion in Drug Discovery and Development, 2007, vol. 10 (5), 550-559.

Souillac, et al, "Characterization of Delivery Systems, Differential Scanning Calorimetry," Encyclopedia of Controlled Drug Delivery, 1999, pp. 217-218.

Steffens, et al., "Low Dose Oral Cannabinoid Therapy Reduces Progression of Atherosclerosis in Mice," Nature, 2005, vol. 434, pp. 782-786.

Takeda, et al., "Convenient Methods for Syntheses of Active Carbamates, Ureas and Nitrosoureas Using N,N-disuccinimido Carbonate (DSC)," Tetrahedron Letters, 1983, vol. 24, pp. 4569-4572.

Testa, B., "Prodrugs: Bridging Pharmacodynamic/Pharmacokinetic Gaps," Current Opinion in Chemical Biology, 2009, vol. 13 (3), pp. 338-344.

Thomson, J., "Physiological Effects of $D_2O$ in Mammals," Annals of the New York Academy of Sciences, 1960, vol. 84, pp. 736-744.

Valenzano, et al., "Pharmacological and Pharmacokinetic Characterization of the Cannabinoid Receptor 2 Agonist, Gw405833, Utilizing Rodent Models of Acute and Chronic Pain, Anxiety, Ataxia and Catalepsy," Neuropharmacology, 2005, vol. 48, pp. 658-672.

Vippagunta, et al., "Crystalline Solids," Advanced Drug Delivery Reviews, 2001, vol. 48 (1), pp. 3-26.

Walter, et al., "Cannabinoids and Neuroinflammation," British Journal of Pharmacology, 2004, vol. 141 (5), pp. 775-785.

Wang, et al., Drug Delivery: Principles and Applications, John Wiley & Sons, Inc., 2005, pp. 136-137.

Warhurst, et al., "Interferon γ Induces Differential Upregulation of α and β Chemokine Secretion in Colonic Epithelial Cell Lines," Gut, 1998, vol. 42 (2), pp. 208-213.

Watkins, et al., "Glial Activation: A Driving Force for Pathological Pain," Trends in Neuroscience, 2001, vol. 24 (8), pp. 450-455.

Werbel, et al., "1-Alkyl-3-(3-alkyl-5-nitro-4-thiazolin-2-ylidene)ureas and Related Compounds as Schistosomicides," Journal of Medicinal Chemistry, 1972, vol. 15 (9), pp. 955-963.

Weyer, et al., "Blutzuckersenkende Chinolin-8-Carboxamidoalkyl-Benzol Sulfonamid Derivate," Arzneimittel-Forschung, 1974, vol. 24 (3), pp. 269-275.

Widdowson, et al., "Palladium Catalysed Suzuki Reactions of Fluoroarenes," Chemical Communication (Camb), 2003, vol. 5, pp. 578-579.

Williams, et al., "Renin Inhibitors Containing Conformationally Restricted P1-P1 Dipeptide Mimetics," Journal of Medicinal Chemistry, 1991, vol. 34 (3), pp. 887-900.

Wright, et al., "Differential Expression of Cannabinoid Receptors in the Human Colon: Cannabinoids Promote Epithelial Wound Healing," Gastroenterology, 2005, vol. 129 (2), pp. 437-453.

Wu, et al., "Regulatory Perspectives of Type II Prodrug Development and Time-Dependent Toxicity Management: Nonclinical Pharm/Tox Analysis and the Role of Comparative Toxicology," Toxicology, 2007, vol. 236 (1-2), pp. 1-6.

Yao, et al., "In Vitro Pharmacological Characterization of Am1241: A Protean Agonist At The Cannabinoid $CB_2$ Receptor," British Journal of Pharmacology, 2006, vol. 149 (2), pp. 145-154.

Yoshihara, et al., "Cannabinoid Receptor Agonists Inhibit Sensory Nerve Activation in Guinea Pig Airways," American Journal of Respiratory and Critical Care Medicine, 2004, vol. 170 (9), pp. 941-946.

Yoshihara, et al., "Endogenous Cannabinoid Receptor Agonists Inhibit Neurogenic Inflammations in Guinea Pig Airways," Allergy and Immunology, 2005, vol. 138, pp. 80-87.

Yoshihara, et al., "The Cannabinoid Receptor Agonist WIN 55212-2 Inhibits Neurogenic Inflammations in Airway Tissues," Journal of Pharmacological Sciences, 2005, vol. 98 (1), pp. 77-82.

Zimmer, et al., "Increased Mortality, Hypoactivity, and Hypoalgesia in Cannabinoid $CB_1$ Receptor Knockout Mice," Proceedings of the National Academy of Science, 1999, vol. 96 (10), pp. 5780-5785.

* cited by examiner

COMPOUNDS AS CANNABINOID RECEPTOR LIGANDS

This application is a divisional application of U.S. Patent application Ser. No. 12/401,788, filed Mar. 11, 2009, which claims the benefit of U.S. Provisional Application Serial No. 61/035,632, filed Mar. 11, 2008 both of which are incorporated herein by reference.

TECHNICAL FIELD

Disclosed herein are compounds that are $CB_2$ receptor ligands, compositions comprising such compounds, and methods of treating conditions and disorders using such compounds and pharmaceutical compositions thereof.

BACKGROUND (−)-$\Delta^9$-Tetrahydrocannabinol ($\Delta^9$-THC), the major psychoactive constituent of marijuana, exerts a broad range of biological effects through its interactions with two cannabinoid (CB) receptor subtypes, $CB_1$ and $CB_2$. $CB_1$ receptors are highly expressed in the central nervous system and to a lesser degree in the periphery in a variety of tissues of the cardiovascular and gastrointestinal systems. By contrast, $CB_2$ receptors are most abundantly expressed in multiple lymphoid organs and cells of the immune system, including spleen, thymus, tonsils, bone marrow, pancreas and mast cells.

The psychotropic effects caused by $\Delta^9$-THC and other nonselective CB agonists are mediated by $CB_1$ receptors. These $CB_1$ receptor-mediated effects, such as euphoria, sedation, hypothermia, catalepsy, and anxiety, have limited the development and clinical utility of nonselective CB agonists. Recent studies have demonstrated that $CB_2$ modulators are analgesic in preclinical models of nociceptive and neuropathic pain without causing the adverse side effects associated with $CB_1$ receptor activation. Therefore, compounds that selectively target $CB_2$ receptors are an attractive approach for the development of novel analgesics.

Pain is the most common symptom of disease and the most frequent complaint with which patients present to physicians. Pain is commonly segmented by duration (acute vs. chronic), intensity (mild, moderate, and severe), and type (nociceptive vs. neuropathic).

Nociceptive pain is the most well known type of pain, and is caused by tissue injury detected by nociceptors at the site of injury. After the injury, the site becomes a source of ongoing pain and tenderness. This pain and tenderness are considered "acute" nociceptive pain. This pain and tenderness gradually diminish as healing progresses and disappear when healing is complete. Examples of acute nociceptive pain include surgical procedures (post-op pain) and bone fractures. Even though there may be no permanent nerve damage, "chronic" nociceptive pain results from some conditions when pain extends beyond six months. Examples of chronic nociceptive pain include osteoarthritis, rheumatoid arthritis, and musculoskeletal conditions (e.g., back pain), cancer pain, etc.

Neuropathic pain is defined as "pain initiated or caused by a primary lesion or dysfunction in the nervous system" by the International Association for the Study of Pain. Neuropathic pain is not associated with nociceptive stimulation, although the passage of nerve impulses that is ultimately perceived as pain by the brain is the same in both nociceptive and neuropathic pain. The term neuropathic pain encompasses a wide range of pain syndromes of diverse etiologies. The three most commonly diagnosed pain types of neuropathic nature are diabetic neuropathy, cancer neuropathy, and HIV pain. In addition, neuropathic pain is diagnosed in patients with a wide range of other disorders, including trigeminal neuralgia, post-herpetic neuralgia, traumatic neuralgia, phantom limb, as well as a number of other disorders of ill-defined or unknown origin.

Managing the spectrum of pain etiologies remains a major public health problem and both patients and clinicians are seeking improved strategies to effectively manage pain. No currently available therapies or drugs effectively treat all types of nociceptive and neuropathic pain states. Compounds described herein are novel $CB_2$ receptor modulators that have utility in treating pain, including nociceptive and neuropathic pain.

SUMMARY

Provided generally herein are compounds that are $CB_2$ receptor ligands and pharmaceutical compositions and methods for the treatment of disorders using these compounds and pharmaceutical compositions.

Presented herein are compounds of formula (I)

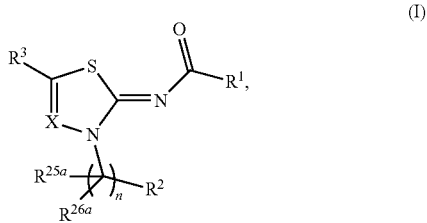

and pharmaceutically acceptable salts, solvates, prodrugs, salts of prodrugs, or any combinations thereof, wherein X is $CR^4$ or N;

$R^1$ is phenyl or quinolin-8-yl wherein said phenyl is substituted with one group represented by $R^{10}$ and optionally further substituted with 1, 2, or 3 groups represented by $R^{11a}$; and wherein said quinolin-8-yl is optionally substituted with 1 or 2 groups represented by $R^{11b}$;

$R^2$ is —$NR^{23a}SO_2R^{105a}$, —$NR^{23b}COR^{105b}$, —$NR^{23b}CO(O)R^{105b}$, —$NR^{23}CONR^{101a}R^{102a}$, —$NR^{23d}SO_2NR^{101b}R^{102b}$, —$NR^{23e}R^{24}$, —$SO_2NR^{101e}R^{102e}$, —$OC(O)NR^{101a}R^{102a}$, $A^1$, $A^2$, or $A^3$; with the proviso that when X is $CR^4$, $R^1$ is substituted phenyl, and $R^2$ is —$OC(O)NR^{101a}R^{102a}$ wherein $R^{101a}$ and $R^{102a}$ are each independently hydrogen, alkyl, alkoxyalkyl, cycloalkyl, haloalkyl, or haloalkoxyalkyl, then $R^{10}$ is other than haloalkoxyalkoxy, —O—$NR^{23f}R^{23g}$, —O—$(CR^{25b}R^{26b})_u$-$A^4$, —O—$(CR^{25b}R^{26b})_u$—C(=S)$NR^{101d}R^{102d}$, —O—$(CR^{25b}R^{26b})_u$—C(O)$NR^{101d}R^{102d}$, —O—$(CR^{25b}R^{26b})_u$—$SO_2NR^{101d}R^{102d}$, and —O—$(CR^{25b}R^{26b})_q$—$NR^{103}R^{104}$;

$A^1$ is a monocyclic heterocycle containing 1 or 2 nitrogen atoms and 0 or 1 sulfur atoms, wherein each $A^1$ is independently unsubstituted or substituted with 1, 2, or 3 substituents represented by $R^{21a}$;

$A^2$ is a bicyclic spiroheterocycle containing 1 or 2 nitrogen atoms and 0 or 1 sulfur atoms, wherein each $A^2$ is independently unsubstituted or substituted with 1, 2, or 3 substituents represented by $R^{21b}$;

$A^3$ is imidazolyl, pyrazolyl, pyrrolyl, thiazolyl, thiadiazolyl, isothiazolyl, triazolyl, or pyridinyl, wherein each $A^3$ is independently unsubstituted or substituted with 1, 2, or 3 substituents represented by $R^{22a}$;

$R^3$ is hydrogen, alkyl, alkenyl, alkynyl, cycloalkyl, cycloalkylalkyl, alkoxyalkyl, hydroxyalkyl, haloalkyl, halo, cyano, or cyanoalkyl; with the proviso that when n is 1, $R^1$ is substituted phenyl, X is $CR^4$ wherein $R^4$ is hydrogen, $R^2$ is $A^3$, and $A^3$ is pyridinyl or 1,3-thiazolyl, then $R^3$ is other than hydrogen;

$R^4$ is alkyl, alkenyl, alkynyl, cycloalkyl, hydrogen, or haloalkyl;

$R^{10}$ is alkoxy, alkoxyalkoxy, alkoxyalkyl, alkyl, alkenyl, alkynyl, alkylcarbonyl, cycloalkylalkyl, cyano, cyanoalkyl, formyl, halo, haloalkoxy, haloalkoxyalkoxy, haloalkyl, —$CR^{106a}$(=N—$OR^{106b}$), —O—$NR^{23f}R^{23g}$, —O—$(CR^{25b}R^{26b})_u$-$A^4$, —O—$(CR^{25b}R^{26b})_u$—C(=O)$NR^{101d}R^{102d}$, —O—$(CR^{25b}R^{26b})_u$—C(=S)$NR^{101d}R^{102d}$, —O—$(CR^{25b}R^{26b})_u$—$SO_2NR^{101d}R^{102d}$, —O—$(CR^{25b}R^{26b})_q$—$NR^{103}R^{104}$, —$NR^{23f}R^{23g}$, —$NR^{23f}$—$(CR^{25b}R^{26b})_u$-$A^4$, —$NR^{23f}$—$(CR^{25b}R^{26b})_u$—C(=O)$NR^{101d}R^{102d}$, —$NR^{23f}$—$(CR^{25b}R^{26b})_u$—C(=S)$NR^{101d}R^{102d}$, —$NR^{23f}$—$(CR^{25b}R^{26b})_u$—$SO_2NR^{101d}R^{102d}$, —$NR^{23f}$—$(CR^{25b}R^{26b})_q$—$NR^{103}R^{104}$, or $A^4$;

$R^{11a}$ and $R^{11b}$, at each occurrence, are each independently alkoxy, alkyl, alkenyl, alkynyl, alkylcarbonyl, cycloalkyl, cycloalkyloxy, cyano, cyanoalkyl, formyl, halo, haloalkoxy, haloalkoxyalkoxy, haloalkyl, —$CR^{106a}$(=N—$OR^{106b}$), furanyl, oxazolyl, oxadiazolyl, isoxazolyl, triazolyl, pyrazolyl, thiazolyl, oxetanyl, tetrahydrofuranyl, or pyranyl;

$R^{21a}$, $R^{21b}$, $R^{21c}$, and $R^{21d}$, at each occurrence, are each independently alkyl, alkenyl, alkynyl, alkoxy, alkoxyalkoxy, alkoxyalkyl, halo, haloalkyl, haloalkoxy, haloalkoxyalkyl, oxo, =S, hydroxy, cyano, cyanoalkyl, =N—CN, =N—$OR^{106b}$, —$CR^{106a}$(=N—$OR^{106b}$), —$CONR^{101d}R^{102d}$, —$SO_2NR^{101d}R^{102d}$, —$COR^{105d}$, —C(O)$OR^{105c}$, or —$SO_2R^{105c}$;

$R^{22a}$ and $R^{22b}$, at each occurrence, are each independently alkyl, alkenyl, alkynyl, alkoxy, alkoxyalkoxy, alkoxyalkyl, halo, haloalkyl, haloalkoxy, haloalkoxyalkyl, hydroxy, cyano, cyanoalkyl, —$CR^{106a}$(=N—$OR^{106b}$), —$CONR^{101d}R^{102d}$, —$SO_2NR^{101d}R^{102d}$, —$COR^{105d}$, —C(O)$OR^{105c}$, or —$SO_2R^{105c}$;

$R^{23a}$, $R^{23b}$, $R^{23c}$, $R^{23d}$, $R^{23e}$, $R^{23f}$, and $R^{23g}$ are each independently hydrogen, alkyl, cycloalkyl, haloalkyl, alkoxyalkyl, or haloalkoxyalkyl;

$R^{24}$ is alkyl, haloalkyl, alkoxyalkyl, haloalkoxyalkyl, or $A^5$;

$A^4$ and $A^5$, at each occurrence, are each independently a cycloalkyl, a monocyclic heterocycle that is optionally substituted with 1, 2, or 3 substituents represented by $R^{21c}$; a bicyclic spiroheterocycle that is optionally substituted with 1, 2, or 3 substituents represented by $R^{21d}$; or a monocyclic heteroaryl that is optionally substituted with 1, 2, or 3 substituents represented by $R^{22b}$;

$R^{25a}$ and $R^{26a}$, at each occurrence, are each independently hydrogen, alkyl, cyclopropyl, cyclobutyl, cyclopentyl, halo, haloalkyl, or alkoxy; $R^{25a}$ and $R^{26a}$ taken together with the carbon atom to which they are attached optionally form a monocyclic ring selected from the group consisting of cyclopropyl, cyclobutyl, cyclopentyl, and cyclohexyl; wherein each of the cyclopropyl, cyclobutyl, cyclopentyl, and cyclohexyl is independently unsubstituted or substituted with 1, 2, 3, 4, 5, or 6 substituents independently selected from the group consisting of alkyl, halo, haloalkyl, alkoxy, oxo, hydroxy, cyano, and haloalkoxy;

$R^{25b}$ and $R^{26b}$, at each occurrence, are each independently hydrogen, alkyl, cyclopropyl, cyclobutyl, cyclopentyl, halo, haloalkyl, or alkoxy;

$R^{101a}$, $R^{101b}$, $R^{101c}$, $R^{102a}$, $R^{102b}$, and $R^{102c}$, at each occurrence, are each independently hydrogen, alkyl, alkoxyalkyl, cycloalkyl, haloalkyl or haloalkoxyalkyl; $R^{101a}$ and $R^{102a}$, or $R^{101b}$ and $R^{102b}$, or $R^{101c}$ and $R^{102c}$, together with the respective nitrogen atom to which they are attached optionally form a 4-7 membered monocyclic heterocycle; wherein said monocyclic heterocycle contains 0 or 1 additional heteroatom, 0 or 1 double bond, and is optionally substituted with 1, 2, or 3 substituents independently selected from the group consisting of alkyl, alkoxy, haloalkyl, halo, hydroxy, and oxo;

$R^{101d}$ and $R^{102d}$, at each occurrence, are each independently hydrogen, alkyl, alkoxyalkyl, cycloalkyl, haloalkyl or haloalkoxyalkyl; $R^{101d}$ and $R^{102d}$, together with the nitrogen atom to which they are attached, optionally form a 4-7 membered monocyclic heterocycle; wherein said monocyclic heterocycle contains 0 or 1 additional heteroatom, 0 or 1 double bond, and is optionally substituted with 1, 2, or 3 substituents independently selected from the group consisting of alkyl, alkoxy, haloalkyl, halo, hydroxy, and oxo;

$R^{103}$ is hydrogen, alkyl, haloalkyl, or alkoxyalkyl;

$R^{104}$ is hydrogen, alkyl, alkylcarbonyl, alkylsulfonyl, alkoxyalkyl, cycloalkyl, haloalkyl, or haloalkoxyalkyl;

$R^{105a}$, $R^{105b}$, and $R^{105c}$, at each occurrence, are each independently alkyl, cycloalkyl, cycloalkylalkyl, alkoxyalkyl, haloalkyl, or cyanoalkyl;

$R^{105d}$, at each occurrence, is independently hydrogen, alkyl, cycloalkyl, cycloalkylalkyl, alkoxyalkyl, haloalkyl, or cyanoalkyl;

$R^{106a}$ and $R^{106b}$, at each occurrence, are each independently hydrogen, methyl, ethyl, propyl, isopropyl, n-butyl, sec-butyl, isobutyl, tert-butyl, cyclopropyl, or cyclobutyl;

n is 1, 2, 3, or 4;

u is 0, 1, 2, 3, or 4;

q is 2, 3, or 4, and each occurrence of the cycloalkyl, the cycloalkyl moiety of the cycloalkylalkyl and the cycloalkyloxy, the cyclopropyl, the cyclobutyl, and the cyclopentyl, as represented by $R^3$, $R^4$, $R^{10}$, $R^{11a}$, $R^{11b}$, $R^{23a}$, $R^{23b}$, $R^{23c}$, $R^{23d}$, $R^{23e}$, $R^{23f}$, $R^{23g}$, $A^4$, $A^5$, $R^{25a}$, $R^{26a}$, $R^{25b}$, $R^{26b}$, $R^{101a}$, $R^{101b}$, $R^{101c}$, $R^{101d}$, $R^{102a}$, $R^{102b}$, $R^{102c}$, $R^{102d}$, $R^{104}$, $R^{105a}$, $R^{105b}$, $R^{105c}$, $R^{105d}$, $R^{106a}$, and $R^{106b}$, are each independently unsubstituted or substituted with 1, 2, 3, 4, 5, or 6 substituents independently selected from the group consisting of alkyl, halo, haloalkyl, alkoxy, oxo, hydroxy, cyano, and haloalkoxy.

Another aspect relates to pharmaceutical compositions comprising therapeutically effective amount of compound(s) described herein or pharmaceutically acceptable salts thereof, in combination with one or more pharmaceutically acceptable carriers. Such compositions can be administered in accordance with methods described herein, typically as part of a therapeutic regimen for treatment or prevention of conditions and disorders related to cannabinoid (CB) receptor subtype $CB_2$. More particularly, the method is useful for treating conditions related to neuropathic pain, nociceptive pain, inflammatory pain, neurological disorders, cancers of the immune system, respiratory disorders, obesity, diabetes, cardiovascular disorders, or for providing neuroprotection.

Yet another aspect relates to methods for treating disease or conditions as described above, or providing neuroprotection, in mammals in need of such treatment. These methods comprise administering to the mammals therapeutically effective amounts of one or more compounds described herein, or pharmaceutically acceptable salts, prodrugs, solvates thereof, or combinations thereof, alone or in combination with one or more pharmaceutically acceptable carriers.

A further aspect relates to the use of compounds described herein or pharmaceutically acceptable salt(s) thereof, in the manufacture of a medicament for the treatment of the disease conditions described above, alone or in combination with one or more pharmaceutically acceptable carrier(s), particularly for the treatment of neuropathic pain, nociceptive pain, inflammatory pain, or combination thereof.

The compounds, compositions comprising the compounds, and methods for treating or preventing conditions and disorders by administering the compounds are further described herein.

These and other objectives are described in the following paragraphs. These objectives should not be deemed to narrow the scope of the invention.

DETAILED DESCRIPTION

Compounds of formula (I) are disclosed

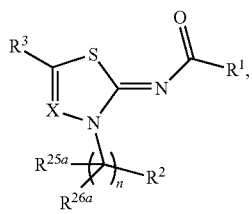

wherein $R^1$, $R^2$, $R^3$, $R^{25a}$, $R^{26a}$, X, and n are as defined above in the Summary and below in the Detailed Description. Compositions comprising such compounds and methods for treating conditions and disorders using such compounds and compositions are also disclosed.

In various embodiments, compounds described herein may contain variables that occur more than one time in any substituent or in the compound described or any other formulae herein. Definition of a variable on each occurrence is independent of its definition at another occurrence. Further, combinations of substituents are permissible only if such combinations result in stable compounds. Stable compounds are compounds, which can be isolated from a reaction mixture.

a. Definitions

As used in the specification and the appended claims, unless specified to the contrary, the following terms have the meaning indicated:

The term "alkenyl" as used herein, means a straight or branched hydrocarbon chain containing from, for example, 2 to 10 carbons and containing at least one carbon-carbon double bond. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkenylene" denotes a divalent group derived from a straight or branched hydrocarbon chain of, for example, 2, 3, or 4 carbon atoms and contains at least one carbon-carbon double. Representative examples of alkenylene include, but are not limited to, —CH═CH— and —CH$_2$CH═CH—.

The term "alkoxy" as used herein, means an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The term "alkoxyalkoxy" as used herein, means an alkoxy group, as defined herein, appended to the parent molecular moiety through another alkoxy group, as defined herein. Representative examples of alkoxyalkoxy include, but are not limited to, tert-butoxymethoxy, 2-ethoxyethoxy, 2-methoxyethoxy, and methoxymethoxy.

The term "alkoxyalkyl" as used herein, means an alkoxy group, as defined herein, appended to the parent molecular moiety through an alkylene group, as defined herein. Representative examples of alkoxyalkyl include, but are not limited to, tert-butoxymethyl, 2-ethoxyethyl, 2-methoxyethyl, and methoxymethyl.

The term "alkyl" as used herein, means a saturated, straight or branched saturated hydrocarbon chain containing from, for example, 1 to 10 carbon atoms. The term "$C_{1-6}$ alkyl" as used herein, means a saturated, straight or branched saturated hydrocarbon chain containing from 1 to 6 carbon atoms. Representative examples of alkyl include, but are not limited to, methyl, ethyl, n-propyl, isopropyl, n-butyl, sec-butyl, isobutyl, tert-butyl, n-pentyl, isopentyl, neopentyl, n-hexyl, 1-methylbutyl, 2-methylbutyl, 3-methylbutyl, 1,1-dimethylpropyl, 1,2-dimethylpropyl, 2,2-dimethylpropyl, 1-methylpropyl, 1-ethylpropyl, 1,2,2-trimethylpropyl, 3-methylhexyl, 2,2-dimethylpentyl, 2,3-dimethylpentyl, n-heptyl, n-octyl, n-nonyl, and n-decyl.

The term "alkylcarbonyl" as used herein, means an alkyl group, as defined herein, appended to the parent molecular moiety through a C(═O) group.

The term "alkylene" means a divalent group derived from a saturated, straight or branched saturated hydrocarbon chain of from, for example, 1 to 10 carbon atoms. Representative examples of alkylene include, but are not limited to, —CH$_2$—, —CH(CH$_3$)—, —CH(C$_2$H$_5$), —CH(CH(CH$_3$)(C$_2$H$_5$))—, —C(H)(CH$_3$)CH$_2$CH$_2$—, —C(CH$_3$)$_2$—, —CH$_2$CH$_2$—, —CH$_2$CH$_2$CH$_2$—, —CH$_2$CH$_2$CH$_2$CH$_2$—, and —CH$_2$CH(CH$_3$)CH$_2$—.

The term "alkynyl" as used herein, means a straight or branched hydrocarbon chain containing from, for example, 2 to 10 carbon atoms and containing at least one carbon-carbon triple bond. Representative examples of alkynyl include, but are not limited, to acetylenyl, 1-propynyl, 2-propynyl, 1,1-dimethylprop-2-ynyl, 1-propyl-pent-3-ynyl, 3-butynyl, 2-pentynyl, and 1-butynyl.

The term "bicyclic spiroheterocycle" or "bicyclic spiroheterocyclic" as used herein refers to a monocyclic heterocycle having two or more substituents wherein two substituents on the same carbon atom, together with said carbon atom, form a second 4-, 5-, or 6-membered monocyclic ring selected from a monocyclic cycloalkyl or a monocyclic heterocycle. The bicyclic spiroheterocyclic groups are connected to the parent molecular moiety through any substitutable carbon atom or any substitutable nitrogen atom contained within the group. The bicyclic spiroheterocyclic groups described herein may also contain an alkenylene bridge of 2, 3, or 4 carbon atoms, or an alkylene bridge of 1, 2, 3, or 4 carbon atoms, wherein each bridge links two non-adjacent carbon atoms within the groups. Examples of bicyclic spiroheterocycles include, but are not limited to, 2-azaspiro[bicyclo [2.2.1]heptane-6,1'-cyclopropane], 2-oxa-5-azaspiro[3.4]octane, 5-azaspiro[2.4]heptane, 5-oxaspiro[3,4]octane and 2,5-dioxaspiro[3.4]octane.

The term "cycloalkyl" as used herein, means a carbocyclic ring system containing 3, 4, 5, 6, 7, or 8 carbon atoms and zero heteroatoms as ring atoms, and zero double bonds. Examples of cycloalkyls include, but are not limited to, cyclopropyl, cyclobutyl, cyclopentyl, cyclohexyl, cycloheptyl, and cyclooctyl. The cycloalkyl groups described herein may contain one or two alkylene bridges of 1, 2, 3, or 4 carbon atoms or one or two alkenylene bridges of 2, 3, or 4 carbon atoms, wherein each of said bridges links two non-adjacent atoms within the cycloalkyl. Examples of such bridged cycloalkyls include, but are not limited to, adamantane, bicyclo[2.2.1]heptane, bicyclo[3.1.1]heptane, bicyclo[2.2.2]octane, bicyclo[3.3.1]nonane. The cycloalkyl groups of the described herein can be appended to the parent molecular moiety through any substitutable carbon atom.

The term "cycloalkylalkyl" as used herein, means a cycloalkyl group, as defined herein, appended to the parent molecular moiety through an alkylene group, as defined herein. Representative examples of cycloalkylalkyl include, but are not limited to, cyclopentylmethyl, cyclohexylmethyl, cyclopropylmethyl, and 1-cyclopropylethyl.

The term "cycloalkyloxy," as used herein means a cycloalkyl group, as defined herein, appended to the parent molecular moiety through an oxygen atom.

The term "cyano," as used herein, means a —CN group.

The term "cyanoalkyl," as used herein, means a cyano group, as defined herein, appended to the parent molecular moiety through an alkylene group, as defined herein. Representative examples of cyanoalkyl include, but are not limited to, cyanomethyl, 2-cyanoethyl, and 3-cyanopropyl.

The term "formyl," as used herein, means a —C(O)H group.

The term "halo" or "halogen," as used herein, means —Cl, —Br, —I or —F.

The term "haloalkoxy," as used herein, means an alkoxy group, as defined herein, in which one, two, three, four, five, or six hydrogen atoms are replaced by halogen. Representative examples of haloalkoxy include, but are not limited to, trifluoromethoxy, difluoromethoxy, 2,2,2-trifluoroethoxy, 2,2-difluoroethoxy, 2-fluoroethoxy, and pentafluoroethoxy.

The term "haloalkoxyalkoxy," as used herein, means a haloalkoxy group, as defined herein, appended to the parent molecular moiety through an alkoxy group, as defined herein.

The term "haloalkoxyalkyl," as used herein, means a haloalkoxy group, as defined herein, appended to the parent molecular moiety through an alkylene group, as defined herein.

The term "haloalkyl," as used herein, means an alkyl group, as defined herein, in which one, two, three, four, five, six, or seven hydrogen atoms are replaced by halogen. Representative examples of haloalkyl include, but are not limited to, chloromethyl, 2-fluoroethyl, 2,2-difluoroethyl, trifluoromethyl, 2,2,2-trifluoroethyl, 2,2,2-trifluoro-1,1-dimethylethyl, difluoromethyl, 3,3,3-trifluoropropyl, pentafluoroethyl, 2-chloro-3-fluoropentyl, and 2-iodoethyl.

The term "monocyclic heteroaryl," as used herein, means a 5- or 6-membered ring containing at least one heteroatom independently selected from the group consisting of O, N, and S. The 5-membered ring contains two double bonds and one, two, three, or four heteroatoms. The 6-membered ring contains three double bonds and one, two, three, or four heteroatoms. Non limiting examples of monocyclic heteroaryl include, furanyl, imidazolyl, isoxazolyl, isothiazolyl, oxadiazolyl, oxazolyl, pyridinyl (including but not limited to, pyridin-2-yl, pyridin-3-yl), pyridazinyl, pyrimidinyl, pyrazinyl, pyrazolyl (e.g. pyrazol-5-yl), pyrrolyl (including, but not limited thereto, 1H-pyrrol-1-yl), tetrazolyl, thiadiazolyl, thiazolyl (including, but not limited thereto, 1,3-thiazol-4-yl, 1,3-thiazol-2-yl, and 1,3-thiazol-5-yl), thienyl, triazolyl, triazinyl, and the like. The monocyclic heteroaryl groups are connected to the parent molecular moiety through any substitutable carbon atom or any substitutable nitrogen atom contained within the groups. Any oxidized forms of nitrogen or sulfur in the monocyclic heteroaryl groups are also contemplated.

The term "heteroatom" includes an oxygen atom, a nitrogen atom, and a sulfur atom.

The term "monocyclic heterocycle" or "monocyclic heterocyclic," as used herein, means a a 3-, 4-5-, 6-, 7-, or 8-membered monocyclic ring containing at least one heteroatom independently selected from the group consisting of O, N, and S. The 3- or 4-membered ring contains 1 heteroatom selected from the group consisting of O, N and S, and optionally one double bond. The 5-membered ring contains zero or one double bond, and one, two or three heteroatoms in the ring selected from the group consisting of O, N and S. The 6-, 7-, or 8-membered ring contains zero, one, or two double bonds, and one, two, or three heteroatoms in the ring selected from the group consisting of O, N and S. Non limiting examples of monocyclic heterocycles include, azetidinyl (including azetidin-1-yl, azetidin-2-yl, azetidin-3-yl), azepanyl, aziridinyl, diazepanyl, 1,3-dioxanyl, 1,4-dioxanyl, 1,3-dioxolanyl, 4,5-dihydroisoxazol-5-yl, 3,4-dihydropyran-6-yl, 1,3-dithiolanyl, 1,3-dithianyl, imidazolinyl, imidazolidinyl (e.g. imidazolidin-1-yl), isothiazolinyl, isothiazolidinyl, isoxazolinyl, isoxazolidinyl, morpholinyl, oxadiazolinyl, oxadiazolidinyl, oxazolinyl, oxazolidinyl, oxetanyl, piperazinyl, piperidinyl (e.g. piperidin-1-yl, piperidin-2-yl, piperidin-3-yl), pyranyl, pyrazolinyl, pyrazolidinyl, pyrrolinyl, pyrrolidinyl (including, but not limited thereto, pyrrolidin-1-yl, pyrrolidin-2-yl), tetrahydrofuranyl (including tetrahydrofuran-2-yl and tetrahydrofuran-3-yl), tetrahydropyranyl, tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, trithianyl, and the like. Monocyclic heterocycle groups described herein may contain an alkenylene bridge of 2, 3, or 4 carbon atoms, or one or two alkylene bridges of 1, 2, 3, or 4 carbon atoms, wherein each bridge links two non-adjacent carbon atoms within the groups. Examples of such bridged heterocycles include, but are not limited to, 2-oxa-5-azabicyclo[2.2.1]heptane, 2-azabicyclo[2.2.1]heptane, oxaadamantane (2-oxatricyclo[3.3.1.1$^{3,7}$]decane), octahydro-2,5-epoxypentalene, hexahydro-2H-2,5-methanocyclopenta[b]furan, hexahydro-1H-1,4-methanocyclopenta[c]furan, oxabicyclo[2.2.1]heptane and 2,4-dioxabicyclo[4.2.1]nonane. The monocyclic heterocycle groups are connected to the parent molecular moiety through any substitutable carbon atom or any substitutable nitrogen atom contained within the groups. Any oxidized form of nitrogen or sulfur, and the quarternized form of any basic nitrogen in the monocyclic heterocycle groups are also contemplated.

The term "hydroxy" as used herein, means an —OH group.

The term "hydroxyalkyl" as used herein, means at least one hydroxy group, as defined herein, is appended to the parent molecular moiety through an alkylene group, as defined herein. Representative examples of hydroxyalkyl include, but are not limited to, hydroxymethyl, 2-hydroxyethyl, 3-hydroxypropyl, 2-hydroxyprop-2-yl, 2,3-dihydroxypentyl, and 2-ethyl-4-hydroxyheptyl.

The term "hydroxy-protecting group" or "O-protecting group" means a substituent that protects hydroxy groups against undesirable reactions during synthetic procedures. Examples of hydroxy-protecting groups include, but are not limited to, substituted methyl ethers, for example, methoxymethyl, benzyloxymethyl, 2-methoxyethoxymethyl, 2-(trimethylsilyl)-ethoxymethyl, benzyl, and triphenylmethyl; tetrahydropyranyl ethers; substituted ethyl ethers, for example, 2,2,2-trichloroethyl and t-butyl; silyl ethers, for example, trimethylsilyl, t-butyldimethylsilyl and t-butyldiphenylsilyl; cyclic acetals and ketals, for example, methylene acetal, acetonide and benzylidene acetal; cyclic ortho esters, for example, methoxymethylene; cyclic carbonates; and cyclic boronates. Commonly used hydroxy-protecting groups are disclosed in T. W. Greene and P. G. M. Wuts, Protective Groups in Organic Synthesis, 3rd edition, John Wiley & Sons, New York (1999).

The term "oxo" means =O.

The term "treating" means, and includes, reversing, alleviating, inhibiting the progress of, or preventing, a disease, a disorder, or condition, or one or more symptoms thereof; and, "treatment" refer to the act of treating, as defined above.

The term "mammal" means humans and other animals.

b. Compounds

Compounds of formula (I) are as described above.

Particular values of variable groups in compounds of formula (I) are as follows. Such values may be used where appropriate with any of the other values, definitions, claims or embodiments defined hereinbefore or hereinafter.

As described generally above for compounds of formula (I), $R^1$ is substituted phenyl or optionally substituted quinolin-8-yl.

In certain embodiments, $R^1$ is phenyl, substituted as described in the Summary, for example, $R^1$ is formula (i)

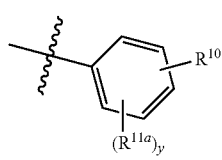

wherein y is 0, 1, 2, or 3, and $R^{10}$ and $R^{11a}$ are as described generally in the Summary and embodiments hereinafter.

Thus, included herein are compounds of formula (I-A)

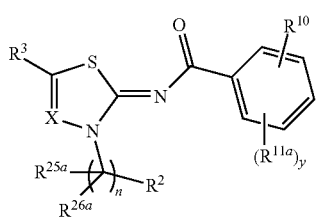

wherein y is 0, 1, 2, or 3, $R^2$, $R^3$, n, X, $R^{10}$, $R^{11a}$, $R^{25a}$, and $R^{26a}$ are each described generally in the Summary and in embodiments described herein.

In conjunction with any of the above or below embodiments, y is 0 or 1.

Certain compounds described herein include those wherein $R^1$ is formula (I) wherein y is 1, for example, such as those represented by formula (ii)

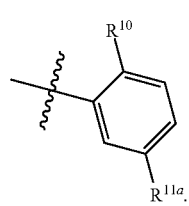

Compounds of formula (I) wherein $R^1$ is formula (II) are represented by formula (I-B)

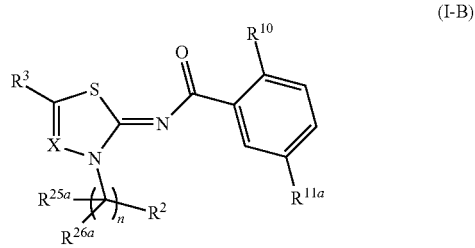

wherein $R^2$, $R^3$, n, X, $R^{10}$, $R^{11a}$, $R^{25a}$, and $R^{26a}$ are each described generally in the Summary and in embodiments described herein.

In yet other embodiments, $R^1$ is formula (iii)

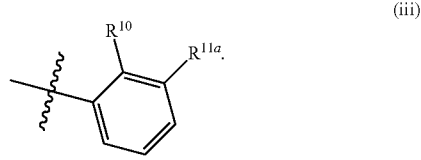

Compounds containing $R^1$ having formula (iii) are represented by formula (I-C)

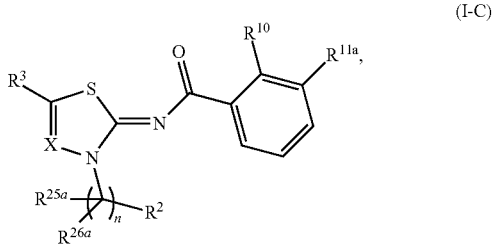

wherein $R^2$, $R^3$, n, X, $R^{10}$, $R^{11a}$, $R^{25a}$, and $R^{26a}$ are each described generally in the Summary and in embodiments described herein.

In yet certain embodiments, $R^1$ is quinolin-8-yl, optionally substituted with 1 or 2 $R^{11b}$ groups, such as those represented by formula (iv)

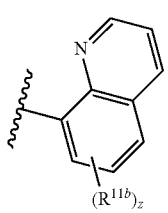

wherein z is 0, 1, or 2, and $R^{11b}$, at each occurrence, represents an optional substituent on any one of the substitutable carbon atoms of the quinoline ring.

Thus, included in the present application are compounds of formula (I) wherein $R^1$ is formula (iv), as represented by formula (I-D)

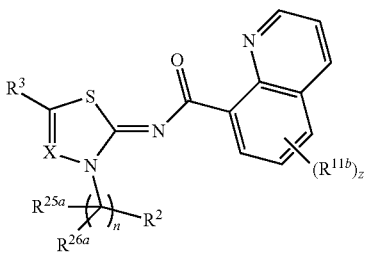

(I-D)

wherein z is 0, 1, or 2, $R^2$, $R^3$, n, X, $R^{11b}$, $R^{25a}$, and $R^{26a}$ are each described generally in the Summary and in embodiments described herein.

In yet certain embodiments, $R^1$ is formula (v)

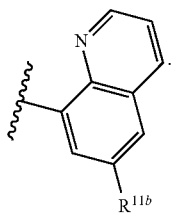

(v)

Thus, included in the present application are compounds of formula (I-E)

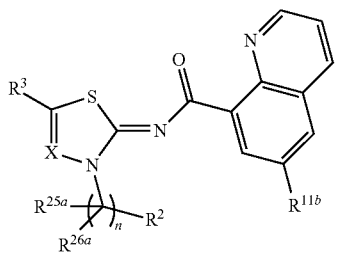

(I-E)

wherein $R^2$, $R^3$, n, X, $R^{11b}$, $R^{25a}$, and $R^{26a}$ are each described generally the Summary and in embodiments described herein.

$R^{10}$ has values as generally described in the Summary. In certain embodiments, $R^{10}$ is, for example, haloalkoxyalkoxy, —O—$NR^{23f}R^{23g}$, —O—$(CR^{25b}R^{26b})_u$-$A^4$, —O—$(CR^{25b}R^{26b})_u$—C(=O)$NR^{101d}R^{102d}$, —O—$(CR^{25b}R^{26b})_u$—C(=S)$NR^{101d}R^{102d}$, —O—$(CR^{25b}R^{26b})_u$—SO$_2$$NR^{101d}R^{102d}$, or —O—$(CR^{25b}R^{26b})_q$—$NR^{103}R^{104}$. In other embodiments, $R^{10}$, for example, is alkoxy, alkoxyalkoxy, alkoxyalkyl, alkyl, alkenyl, alkynyl, alkylcarbonyl, cycloalkylalkyl, cyano, cyanoalkyl, formyl, halo, haloalkoxy, haloalkyl, —$CR^{106a}$(=N—$OR^{106b}$), —$NR^{23f}R^{23g}$, —$NR^{23f}$—$(CR^{25b}R^{26b})_u$-$A^4$, —$NR^{23f}$—$(CR^{25b}R^{26b})_u$—C(=O)$NR^{101d}R^{102d}$, —$NR^{23f}$—$(CR^{25b}R^{26b})_u$—C(=S)$NR^{101d}R^{102d}$, —$NR^{23f}$—$(CR^{25b}R^{26b})_u$—SO$_2$$NR^{101d}R^{102d}$, —$NR^{23f}$—$(CR^{25b}R^{26b})_q$—$NR^{103}R^{104}$, or $A^4$. In yet other embodiments, $R^{10}$, for example, is alkoxy (e.g. methoxy, ethoxy, and the like), haloalkoxy, haloalkyl, halo (e.g., chloro, fluoro, and the like), —O—$NR^{23f}R^{23g}$, —O—$(CR^{25b}R^{26b})_u$-$A^4$, or $A^4$. $R^{23f}$, $R^{23g}$, $R^{25b}$, $R^{26b}$, $R^{101d}$, $R^{102d}$, $R^{103}$, $R^{104}$, $R^{106a}$, $R^{106b}$, q, u, and $A^4$ are as described in the Summary and the embodiments herein below. For example, $R^{25b}$ and $R^{26b}$ are each independently hydrogen or $C_{1-6}$ alkyl (e.g., methyl). $R^{23f}$, for example, is hydrogen. $R^{23g}$, for example, is alkyl (e.g. tert-butyl). $A^4$, for example, is a monocyclic heterocyle (e.g. azetidinyl such as, azetidin-1-yl, azetidin-2-yl, azetidin-3-yl), optionally substituted with 1, 2, or 3 substituents represented by $R^{21c}$, or a monocyclic heteroaryl (e.g. pyridinyl such as pyridin-2-yl and the like), optionally substituted with 1, 2, or 3 substituents represented by $R^{21d}$ wherein $R^{21c}$ and $R^{21d}$ are as described in the Summary. u, for example, is 0 or 1.

In other embodiments, $R^{10}$, for example, is
—O—$NR^{23f}R^{23g}$ wherein $R^{23f}$ is hydrogen and $R^{23g}$, for example, is alkyl (e.g. tert-butyl);
—O—$(CR^{25b}R^{26b})_u$-$A^4$ wherein $R^{25b}$ and $R^{26b}$ are each independently hydrogen or $C_{1-6}$ alkyl (e.g., methyl), u is 0 or 1, and $A^4$, for example, is a monocyclic heterocyle (e.g. azetidinyl such as, azetidin-1-yl, azetidin-2-yl, azetidin-3-yl, pyrrolidin-2-yl, pyrrolidin-3-yl), optionally substituted with 1, 2, or 3 substituents represented by $R^{21c}$, or a monocyclic heteroaryl (e.g. pyridinyl such as pyridin-2-yl and the like), optionally substituted with 1, 2, or 3 substituents represented by $R^{21d}$;
alkoxy (e.g. methoxy, ethoxy);
haloalkoxy (trifluoroethoxy);
halo (e.g. chloro, bromo, fluoro); or
optionally substituted monocyclic heterocycle (e.g. optionally substituted azetidinyl).

$R^{11a}$ and $R^{11b}$ have values as generally described in the Summary. In certain embodiments, $R^{11a}$ and $R^{11b}$ are each independently cyano, haloalkyl (e.g. trifluoromethyl and the like) or halo. In other embodiments, $R^{11a}$ and $R^{11b}$ are each independently fluoro, chloro, bromo, cyano or trifluoromethyl.

As generally described above for compounds of formula (I), X is $CR^4$ or N. In certain embodiments, X is $CR^4$ and $R^4$ is as defined in the Summary. In other embodiments, X is $CR^4$, and $R^4$ is $C_{1-6}$ alkyl (for example, methyl), haloalkyl, or hydrogen. In still other embodiments, X is $CR^4$, and $R^4$ is $C_{1-6}$ alkyl (for example, methyl) or hydrogen. In still other embodiments, X is $CR^4$ and $R^4$ is hydrogen. In yet other embodiments, X is N.

As generally described above for compounds of formula (I), $R^3$ is hydrogen, alkyl, alkenyl, alkynyl, cycloalkyl, cycloalkylalkyl, alkoxyalkyl, hydroxyalkyl, haloalkyl, halo, cyano, or cyanoalkyl; with the proviso that when n is 1, $R^1$ is substituted phenyl, X is $CR^4$ wherein $R^4$ is hydrogen, $R^2$ is $A^3$ wherein $A^3$ is pyridinyl or 1,3-thiazolyl, then $R^3$ is other than hydrogen. In other embodiments, $R^3$ is $C_{1-6}$ alkyl (e.g. methyl, ethyl, tert-butyl), halo (e.g. chloro, bromo), optionally substituted cycloalkyl (e.g. optionally substituted cyclopropyl), haloalkyl, or hydroxyalkyl (e.g. 2-hydroxyprop-2-yl and the like). In other embodiments, $R^3$ is $C_{1-6}$ alkyl (e.g. methyl, ethyl, tert-butyl), halo, or cycloalkyl. In yet other embodiments, $R^3$ is tert-butyl.

As generally described above for compounds of formula (I), $R^2$ is —$NR^{23a}$SO$_2$$R^{105a}$, —$NR^{23b}$COR$^{105b}$, —$NR^{23b}$CO(O)$R^{105b}$, —$NR^{23c}$CONR$^{101a}R^{102a}$, —$NR^{23d}$SO$_2$$NR^{101b}R^{102b}$, —$NR^{23e}R^{24}$, —SO$_2$$NR^{101c}R^{102c}$, —OC(O)$NR^{101a}R^{102a}$, $A^1$, $A^2$, or $A^3$; with the proviso that when X is $CR^4$, $R^1$ is substituted phenyl, and $R^2$ is —OC(O)$NR^{101a}R^{102a}$ wherein $R^{101a}$ and $R^{102a}$ are each independently hydrogen, alkyl, alkoxyalkyl, cycloalkyl, haloalkyl, or haloalkoxyalkyl, then $R^{10}$ is other than haloalkoxyalkoxy, —O—$NR^{23f}R^{23g}$, O—$(CR^{25b}R^{26b})_u$-$A^4$, —O—$(CR^{25b}R^{26b})_u$—C(=S)$NR^{101d}R^{102d}$, —O—

$(CR^{25b}R^{26b})_u$—C(O)NR$^{101d}$R$^{102d}$, —O—$(CR^{25b}R^{26b})_u$—SO$_2$NR$^{101d}$R$^{102d}$, and —O—$(CR^{25b}R^{26b})_q$—NR$^{103}$R$^{104}$.

In certain embodiments, R$^2$ is —NR$^{23a}$SO$_2$R$^{105a}$, —NR$^{23b}$CO(O)R$^{105b}$, —NR$^{23e}$R$^{24}$, —SO$_2$NR$^{101c}$R$^{102c}$, or —OC(O)NR$^{101a}$R$^{102a}$. In certain embodiments, R$^2$ is —NR$^{23a}$SO$_2$R$^{105a}$. In other embodiments, R$^2$ is —NR$^{23b}$CO(O)R$^{105b}$. In yet other embodiments, R$^2$ is —NR$^{23e}$R$^{24}$. In other embodiments, R$^2$ is —SO$_2$NR$^{101c}$R$^{102c}$. In yet other embodiments, R$^2$ is —OC(O)NR$^{101a}$R$^{102a}$. R$^{23a}$, R$^{105a}$, R$^{23b}$, R$^{105b}$, R$^{23e}$, R$^{24}$, R$^{101c}$, R$^{102c}$, R$^{101a}$, and R$^{102a}$ are as described in the Summary and embodiments herein. In conjunction with any of the above or below embodiments, R$^{23a}$, R$^{23b}$, R$^{23e}$ are each independently, for example, but not limited thereto, hydrogen, C$_{1-6}$ alkyl (e.g. methyl and the like), or optionally substituted cycloalkyl (e.g. optionally substituted cyclopropyl), particularly hydrogen or C$_{1-6}$ alkyl (e.g. methyl and the like); R$^{105a}$ and R$^{24}$ are each independently, for example, C$_{1-6}$ alkyl (e.g. methyl, ethyl and the like) or optionally substituted cycloalkyl (e.g. optionally substituted cyclopropyl), particularly C$_{1-6}$ alkyl (e.g. methyl, ethyl and the like); R$^{105b}$ is, for example, C$_{1-6}$ alkyl (e.g. tert-butyl); non-limiting examples of R$^{101a}$, R$^{102a}$, R$^{101c}$, R$^{102c}$, independent of each other, include hydrogen, C$_{1-6}$ alkyl (e.g. methyl, ethyl, tert-butyl and the like), and optionally substituted cyclopropyl, R$^{101a}$ and R$^{102a}$ together with the nitrogen to which they are attached optionally form a 4-7 membered monocyclic heterocycle wherein the monocyclic heterocycle contains 0 or 1 additional heteroatom, 0 or 1 double bond and is optionally substituted with 1, 2, or 3 substituents independently selected from the group consisting of alkyl, alkoxy, haloalkyl, halo, hydroxy and oxo; non-limiting examples of such monocyclic heterocycles include azetidinyl, piperidinyl, and piperazinyl, each of which is optionally substituted as described above.

In another embodiment R$^2$ is —NR$^{23d}$SO$_2$NR$^{101b}$R$^{102b}$ wherein R$^{23d}$, R$^{101b}$, and R$^{102b}$ are as defined in formula (I). R$^{101b}$ and R$^{102b}$ independent of each other, may be chosen from the group consisting of hydrogen, alkyl, alkoxyalkyl, cycloalkyl, haloalkyl and haloalkoxyalkyl. Alternatively, R$^{101b}$ and R$^{102b}$ together with the nitrogen to which they are attached form a 4-7 membered monocyclic heterocycle containing 0 or 1 additional heteroatom, 0 or 1 double bond, and is optionally substituted with 1, 2 or 3 substituents independently selected from the group consisting of alkyl, alkoxy, haloalkyl, halo, hydroxy, and oxo.

In certain embodiments, R$^2$ is A$^1$, A$^2$, or A$^3$.

In certain embodiments, R$^2$ is A$^1$. In other embodiments, R$^2$ is A$^2$. In certain embodiments of formula (I), R$^2$ is A$^3$.

A$^1$, A$^2$, and A$^3$ have meanings as described in the Summary and herein.

In conjunction with any of the above or below embodiments, non limiting examples of A$^1$ include azetidinyl (including, but not limited to, azetidin-3-yl and azetidin-2-yl), pyrrolidinyl (including, but not limited to, pyrrolidin-2-yl and pyrrolidin-1-yl), piperidinyl (including, but not limited to, piperidin-1-yl, piperidin-2-yl, and piperidin-3-yl), and imidazolidinyl (including, but not limited to, imidazolidin-1-yl), wherein each of the azetidinyl, pyrrolidinyl, piperidinyl, and imidazolidinyl groups is independently unsubstituted or substituted with 1, 2, or 3 groups represented by R$^{21a}$ wherein R$^{21a}$ is as described in the Summary and herein. In certain examples of A$^1$, R$^{21a}$ is C$_{1-6}$ alkyl (e.g. methyl, ethyl, and the like), haloalkyl, oxo, =S, —C(O)OR$^{105d}$, or —SO$_2$R$^{105c}$. In certain embodiments of A$^1$, R$^{21a}$, for example, is C$_{1-6}$ alkyl (e.g. methyl, ethyl, and the like), haloalkyl (e.g. trifluoromethyl and the like), oxo, =S, —C(O)OR$^{105d}$, or —SO$_2$R$^{105c}$ wherein R$^{105c}$ is C$_{1-6}$ alkyl (e.g. methyl, ethyl, and the like) or optionally substituted cycloalkyl (e.g. optionally substituted cyclopropyl), and R$^{105d}$ is methyl or ethyl. In yet other examples of A$^1$, R$^{21a}$ is methyl, ethyl, oxo, =S, or —SO$_2$R$^{105c}$ wherein R$^{105c}$ is methyl, ethyl, or optionally substituted cyclopropyl.

In conjunction with any of the above or below embodiments, non limiting examples of A$^3$ include pyrrolyl (including, but not limited to, 1H-pyrrol-1-yl), thiazolyl (including, but not limited to, 1,3-thiazol-4-yl, 1,3-thiazol-5-yl, and 1,3-thiazol-2-yl), pyrazolyl (including, but not limited to, pyrazol-5-yl), or pyridinyl (including, but not limited to, pyridin-3-yl), and each A$^3$ is independently unsubstituted or substituted with 1, 2 or 3 groups represented by R$^{22a}$ wherein R$^{22a}$ is as described in the Summary and herein. In certain examples of A$^3$, R$^{22a}$ is halo, C$_{1-6}$ alkyl (e.g. methyl, ethyl, and the like), or haloalkyl (e.g. trifluoromethyl and the like). In other examples of A$^3$, R$^{22a}$ is methyl, trifluoromethyl, chloro, fluoro, bromo, or iodo.

As described generally in the Summary, R$^{25a}$ and R$^{26a}$, at each occurrence, are each independently hydrogen, alkyl, cyclopropyl, cyclobutyl, cyclopentyl, halo, haloalkyl, or alkoxy; R$^{25a}$ and R$^{26a}$ taken together with the carbon atom to which they are attached optionally form a monocyclic ring selected from the group consisting of cyclopropyl, cyclobutyl, cyclopentyl, and cyclohexyl; wherein each of the cyclopropyl, cyclobutyl, cyclopentyl, and cyclohexyl is independently unsubstituted or substituted with 1, 2, 3, 4, 5, or 6 substituents independently selected from the group consisting of alkyl, halo, haloalkyl, alkoxy, oxo, hydroxy, cyano, and haloalkoxy. In certain embodiments, R$^{25a}$ or R$^{26a}$, at each occurrence, are each independently hydrogen or C$_{1-6}$ alkyl (e.g. methyl, ethyl, and the like). In other embodiments, R$^{25a}$ and R$^{26a}$, at each occurrence, are each independently hydrogen or methyl.

As described generally in the Summary, n is 1, 2, 3, or 4. In certain embodiments, n is 1, 2, or 3. In yet other embodiments, n is 1 or 2.

In certain embodiments, R$^{25a}$ and R$^{26a}$ taken together with the carbon to which they are attached form a monocyclic ring selected from the group consisting of cyclopropyl, cyclobutyl, cyclopentyl, and cyclohexyl. It will be appreciated that only the R$^{25a}$ and R$^{26a}$ groups that are bound to the same carbon atom may form a ring as described above.

It will be appreciated that when R$^{25a}$ and R$^{26a}$ taken together with the carbon to which they are attached form a monocyclic ring as previously described, and n is 2, 3, or 4, then only one set of R$^{25a}$ and R$^{26a}$ may form a ring with the carbon atom to which they are bound to.

Contemplated herein are compounds of formula (I), (I-A), (I-B), (I-C), (I-D) and (I-E) with combinations of the above embodiments, including particular, more particular and preferred embodiments.

For example, within each of the foregoing compounds having formula (I), (I-A), (I-B), (I-C), (I-D), or (I-E), examples of a group include those wherein X is N.

Examples of another group of compounds having formula (I), (I-A), (I-B), (I-C), (I-D), or (I-E) include those wherein X is CR$^4$, and R$^4$ is as described generally above and in embodiments described above and herein, with the proviso that in compounds of formula (I), (I-A), (I-B) or (I-C), when R$^4$ is hydrogen, n is 1, R$^1$ is substituted phenyl, R$^2$ is A$^3$, and A$^3$ is pyridinyl or 1,3-thiazolyl, then R$^3$ is other than hydrogen.

Within each group of compounds of formula (I), (I-A), (I-B), (I-C), (I-D), or (I-E) as described in the preceding paragraphs, y, z, R$^1$, R$^2$, R$^3$, R$^4$, n, R$^{10}$, R$^{11a}$, R$^{11b}$, R$^{25a}$, and R$^{26a}$ are each described generally above and in embodiments described above and herein.

Thus, of each groups of compounds of formula (I), (I-A), (I-B), (I-C), (I-D), or (I-E) as described in the preceding paragraphs, examples of a subgroup include, but are not limited to, those wherein $R^2$ is —$NR^{23a}SO_2R^{105a}$, —$NR^{23b}COR^{105b}$, —$NR^{23b}CO(O)R^{105b}$, —$NR^{23c}CONR^{101a}R^{102a}$, —$NR^{23d}SO_2NR^{101b}R^{102b}$, —$NR^{23e}R^{24}$, —$SO_2NR^{101c}R^{102c}$, or —$OC(O)NR^{101a}R^{102a}$.

Examples of another subgroup include, but are not limited to, those wherein $R^2$ is —$NR^{23a}SO_2R^{105a}$, —$NR^{23b}CO(O)R^{105b}$, —$NR^{23e}R^{24}$, —$SO_2NR^{101c}R^{102c}$, or —$OC(O)NR^{101a}R^{102a}$.

Examples of another subgroup include, but are not limited to, those wherein $R^2$ is —$NR^{23a}SO_2R^{105a}$.

Examples of another subgroup include, but are not limited to, those wherein $R^2$ is —$NR^{23b}CO(O)R^{105b}$.

Examples of yet another subgroup include, but are not limited to, those wherein $R^2$ is —$NR^{23e}R^{24}$.

Examples of yet another subgroup include, but are not limited to, those wherein $R^2$ is —$SO_2NR^{101c}R^{102c}$.

Examples of yet another subgroup include, but are not limited to, those wherein $R^2$ is —$OC(O)NR^{101a}R^{102a}$.

In conjunction with any of the above described groups and subgroups, $R^{23a}$, $R^{23b}$, $R^{23c}$, $R^{23d}$, $R^{23e}$, $R^{24}$, $R^{105a}$, $R^{105b}$, $R^{101a}$, $R^{101b}$, $R^{101c}$, $R^{102a}$, $R^{102b}$, and $R^{102c}$, are as described generally in the Summary and in embodiments or examples described above.

Other examples of a subgroup include those wherein $R^2$ is $A^1$, $A^2$, or $A^3$.

Yet other examples of a subgroup of formula (I), (I-A), (I-B), (I-C), (I-D), or (I-E) include, but are not limited to, those wherein $R^2$ is $A^1$.

Examples of yet another subgroup of compounds of formula (I), (I-A), (I-B), (I-C), (I-D), or (I-E) include, but are not limited to, those wherein $R^2$ is $A^2$.

Examples of still another subgroup of compounds of formula (I), (I-A), (I-B), (I-C), (I-D), or (I-E) include, but are not limited to, those wherein $R^2$ is $A^3$.

In conjunction with any of the three preceeding subgroups $A^1$, $A^2$, and $A^3$ have meanings as described generally in the Summary and in embodiments or examples described above.

Of all examples of the groups and subgroups of compounds of formula (I), (I-A), (I-B), (I-C), (I-D), or (I-E) as discussed herein above, y, z, n, $R^1$, $R^3$, $R^4$, $R^{25a}$, $R^{26a}$, $R^{10}$, $R^{11a}$, and $R^{11b}$ are as described generally in the Summary and in embodiments described above. For example, $R^3$ is alkyl (such as, but not limited to, methyl, tert-butyl), halo (for example, chloro, bromo), cycloalkyl, haloalkyl, or hydroxyalkyl. In certain embodiments, $R^3$ is alkyl (for example, methyl, tert-butyl), halo, or cycloalkyl. Preferably, $R^3$ is tert-butyl. $R^4$, for example, is hydrogen, alkyl (for example, methyl), or haloalkyl.

Thus, examples of compounds of formula (I), (I-A)-(I-E) include, but are not limited to, those wherein X is N, $R^2$ is —$NR^{23a}SO_2R^{105a}$, —$NR^{23b}CO(O)R^{105b}$, —$NR^{23e}R^{24}$, —$SO_2NR^{101c}R^{102c}$, or —$OC(O)NR^{101a}R^{102a}$, and $R^3$ is $C_{1-6}$ alkyl (e.g. methyl, ethyl, tert-butyl, and the like), optionally substituted cycloalkyl (e.g. optionally substituted cyclopropyl), halo (e.g. chloro, bromo), haloalkyl, or hydroxyalkyl (e.g. 2-hydroxyprop-2-yl and the like). $R^1$, $R^{10}$, $R^{11a}$, $R^{11b}$, n, y, z, $R^{23a}$, $R^{23b}$, $R^{23e}$, $R^{24}$, $R^{25a}$, $R^{26a}$, $R^{101a}$, $R^{102a}$, $R^{101c}$, $R^{102c}$, $R^{105a}$, and $R^{105b}$ have meanings as described generally in the Summary and in embodiments described above.

Other examples of compounds of formula (I), (I-A)-(I-E) include, but are not limited to, those wherein X is N, $R^2$ is $A^1$, and $R^3$ is $C_{1-6}$ alkyl (e.g. methyl, ethyl, tert-butyl, and the like), optionally substituted cycloalkyl (e.g. optionally substituted cyclopropyl), halo (e.g. chloro, bromo), haloalkyl, or hydroxyalkyl (e.g. 2-hydroxyprop-2-yl and the like). $A^1$, $R^1$, $R^{10}$, $R^{11a}$, $R^{11b}$, n, y, z, $R^{25a}$, and $R^{26a}$ have meanings as described generally in the Summary and in embodiments described above.

Other examples of compounds of formula (I), (I-A)-(I-E) include, but are not limited to, those wherein X is N, $R^2$ is $A^3$, $R^3$ is $C_{1-6}$ alkyl (e.g. methyl, ethyl, tert-butyl, and the like), optionally substituted cycloalkyl (e.g. optionally substituted cyclopropyl), halo (e.g. chloro, bromo), haloalkyl, or hydroxyalkyl (e.g. 2-hydroxyprop-2-yl and the like). $A^3$, $R^1$, $R^{10}$, $R^{11a}$, $R^{11b}$, n, y, z, $R^{25a}$, and $R^{26a}$ have meanings as described generally in the Summary and in embodiments described above.

Yet other examples of compounds of formula (I), (I-A)-(I-E) include, but are not limited to, those wherein X is $CR^4$, $R^2$ is —$NR^{23a}SO_2R^{105a}$, —$NR^{23b}CO(O)R^{105b}$, —$NR^{23e}R^{24}$, —$SO_2NR^{101c}R^{102c}$, or —$OC(O)NR^{101a}R^{102a}$, $R^3$ is $C_{1-6}$ alkyl (e.g. methyl, ethyl, tert-butyl, and the like), optionally substituted cycloalkyl (e.g. optionally substituted cyclopropyl), halo (e.g. chloro, bromo), haloalkyl, or hydroxyalkyl (e.g. 2-hydroxyprop-2-yl and the like), and $R^4$ is hydrogen, $C_{1-6}$ alkyl (e.g. methyl and the like), or haloalkyl. $R^1$, $R^{10}$, $R^{11a}$, $R^{11b}$, n, y, z, $R^{23a}$, $R^{23b}$, $R^{23e}$, $R^{24}$, $R^{25a}$, $R^{26a}$, $R^{101a}$, $R^{102a}$, $R^{101c}$, $R^{102c}$ $R^{105a}$, and $R^{105b}$ have meanings as described generally in the Summary and in embodiments described above.

Other examples of compounds of formula (I), (I-A)-(I-E) include, but are not limited to, those wherein X is $CR^4$, $R^2$ is $A^1$, $R^3$ is $C_{1-6}$ alkyl (e.g. methyl, ethyl, tert-butyl, and the like), optionally substituted cycloalkyl (e.g. optionally substituted cyclopropyl), halo (e.g. chloro, bromo), haloalkyl, or hydroxyalkyl (e.g. 2-hydroxyprop-2-yl and the like), and $R^4$ is hydrogen, $C_{1-6}$ alkyl (e.g. methyl and the like), or haloalkyl. $A^1$, $R^1$, $R^{10}$, $R^{11a}$, $R^{11b}$, n, y, z, $R^{25a}$, and $R^{26a}$ have meanings as described generally in the Summary and in embodiments described above.

Other examples of compounds of formula (I), (I-A)-(I-E) include, but are not limited to, those wherein X is $CR^4$, $R^2$ is $A^3$, and $R^3$ is $C_{1-6}$ alkyl (e.g. methyl, ethyl, tert-butyl, and the like), optionally substituted cycloalkyl (e.g. optionally substituted cyclopropyl), halo (e.g. chloro, bromo), haloalkyl, or hydroxyalkyl (e.g. 2-hydroxyprop-2-yl and the like), and $R^4$ is hydrogen, $C_{1-6}$ alkyl (e.g. methyl and the like), or haloalkyl. $A^3$, $R^1$, $R^{10}$, $R^{11a}$, $R^{11b}$, n, y, z, $R^{25a}$, and $R^{26a}$ have meanings as described generally in the Summary and in embodiments described above.

In conjunction with any groups or subgroups of compounds described above, $A^1$, $A^3$, $R^1$, $R^{10}$, $R^{11a}$, $R^{11b}$, n, y, z, $R^{23a}$, $R^{23b}$, $R^{23c}$, $R^{23d}$, $R^{23e}$, $R^{24}$, $R^{25a}$, $R^{26a}$, $R^{101a}$, $R^{101a}$, $R^{101c}$, $R^{102a}$, $R^{102b}$, $R^{102c}$ $R^{105a}$, and $R^{105b}$ have meanings as described generally in the Summary and in embodiments described above. In certain embodiments, $R^4$ is hydrogen or alkyl (for example, methyl), or haloalkyl. In certain embodiments, $R^4$ is hydrogen or alkyl (for example, methyl). In other embodiments, $R^4$ is hydrogen. $R^{25a}$ and $R^{26a}$, for example, are hydrogen or $C_{1-6}$ alkyl (e.g. methyl, ethyl, and the like), and n is 1, 2, 3, or 4. In certain embodiments, $R^{25a}$ and $R^{26a}$, for example, are hydrogen or methyl, and n is 1 or 2.

Exemplary compounds include, but are not limited to:
N-[(2Z)-5-tert-butyl-3-{[1-(methylsulfonyl)azetidin-3-yl]methyl}-1,3-thiazol-2(3H)-ylidene]-2-methoxy-5-(trifluoromethyl)benzamide;
N-[(2Z)-5-tert-butyl-3-{[1-(cyclopropylsulfonyl)azetidin-3-yl]methyl}-1,3-thiazol-2(3H)-ylidene]-2-methoxy-5-(trifluoromethyl)benzamide;

5-chloro-2-methoxy-N-[(2Z)-5-methyl-3-{[1-(methylsulfonyl)azetidin-3-yl]methyl}-1,3-thiazol-2(3H)-ylidene]benzamide;
N-[(2Z)-5-tert-butyl-3-{[(2R)-5-oxopyrrolidin-2-yl]methyl}-1,3-thiazol-2(3H)-ylidene]-5-chloro-2-methoxybenzamide;
N-[(2Z)-5-tert-butyl-3-{[(2S)-5-oxopyrrolidin-2-yl]methyl}-1,3-thiazol-2(3H)-ylidene]-5-chloro-2-methoxybenzamide;
N-[(2Z)-5-tert-butyl-3-{[(2S)-5-oxopyrrolidin-2-yl]methyl}-1,3,4-thiadiazol-2(3H)-ylidene]-5-chloro-2-methoxybenzamide;
N-[(2Z)-5-tert-butyl-3-{[(2R)-5-oxopyrrolidin-2-yl]methyl}-1,3,4-thiadiazol-2(3H)-ylidene]-5-chloro-2-methoxybenzamide;
N-[(2Z)-5-tert-butyl-3-{[(2S)-1-methyl-5-oxopyrrolidin-2-yl]methyl}-1,3,4-thiadiazol-2(3H)-ylidene]-5-chloro-2-methoxybenzamide;
N-[(2Z)-5-tert-butyl-3-{[1-(methylsulfonyl)azetidin-3-yl]methyl}-1,3-thiazol-2(3H)-ylidene]-5-chloro-2-methoxybenzamide;
N-[(2Z)-5-tert-butyl-3-{2-[methyl(methylsulfonyl)amino]ethyl}-1,3-thiazol-2(3H)-ylidene]-5-chloro-2-methoxybenzamide;
N-[(2Z)-5-tert-butyl-3-[2-(dimethylamino)ethyl]-1,3-thiazol-2(3H)-ylidene]-5-chloro-2-methoxybenzamide;
N-[(2Z)-5-tert-butyl-3-{2-[(methylsulfonyl)amino]ethyl}-1,3-thiazol-2(3H)-ylidene]-5-chloro-2-methoxybenzamide;
N-[(2Z)-5-tert-butyl-3-{2-[(ethylsulfonyl)(methyl)amino]ethyl}-1,3-thiazol-2(3H)-ylidene]-5-chloro-2-methoxybenzamide;
5-chloro-N-[(2Z)-3-[(6-fluoropyridin-3-yl)methyl]-5-methyl-1,3-thiazol-2(3H)-ylidene]-2-methoxybenzamide;
N-[(2Z)-3-[(2R)-azetidin-2-ylmethyl]-5-tert-butyl-1,3-thiazol-2(3H)-ylidene]-5-chloro-2-methoxybenzamide;
5-chloro-N-[(2Z)-5-chloro-3-(1,3-thiazol-4-ylmethyl)-1,3-thiazol-2(3H)-ylidene]-2-methoxybenzamide;
N-[(2Z)-5-bromo-3-(1,3-thiazol-4-ylmethyl)-1,3-thiazol-2(3H)-ylidene]-5-chloro-2-methoxybenzamide;
5-chloro-2-methoxy-N-[(2Z)-5-methyl-3-(1,3-thiazol-4-ylmethyl)-1,3-thiazol-2(3H)-ylidene]benzamide;
N-[(2Z)-5-tert-butyl-3-(1,3-thiazol-4-ylmethyl)-1,3,4-thiadiazol-2(3H)-ylidene]-5-chloro-2-methoxybenzamide;
2,5-dichloro-N-[(2Z)-5-methyl-3-[(2-methyl-1,3-thiazol-4-yl)methyl]-1,3-thiazol-2(3H)-ylidene]benzamide;
5-chloro-2-methoxy-N-[(2Z)-5-methyl-3-[(2-methyl-1,3-thiazol-4-yl)methyl]-1,3-thiazol-2(3H)-ylidene]benzamide;
5-chloro-2-methoxy-N-[(2Z)-5-methyl-3-(1,3-thiazol-2-ylmethyl)-1,3-thiazol-2(3H)-ylidene]benzamide;
5-chloro-2-methoxy-N-[(2Z)-5-methyl-3-[(4-methyl-1,3-thiazol-2-yl)methyl]-1,3-thiazol-2(3H)-ylidene]benzamide;
5-chloro-N-[(2Z)-3-[(6-chloropyridin-3-yl)methyl]-5-methyl-1,3-thiazol-2(3H)-ylidene]-2-methoxybenzamide;
5-chloro-2-methoxy-N-[(2Z)-5-methyl-3-{[6-(trifluoromethyl)pyridin-3-yl]methyl}-1,3-thiazol-2(3H)-ylidene]benzamide;
N-[(2Z)-5-tert-butyl-3-(1,3-thiazol-4-ylmethyl)-2(3H)-ylidene]-5-chloro-2-methoxybenzamide;
2-ethoxy-N-[(2Z)-5-methyl-3-[3-(1H-pyrrol-1-yl)propyl]-1,3-thiazol-2(3H)-ylidene]benzamide;
5-chloro-2-methoxy-N-[(2Z)-5-methyl-3-[3-(1H-pyrrol-1-yl)propyl]-1,3-thiazol-2(3H)-ylidene]benzamide;
N-[(2Z)-5-tert-butyl-3-[(2S)-pyrrolidin-2-ylmethyl]-1,3-thiazol-2(3H)-ylidene]-5-chloro-2-methoxybenzamide;
N-[(2Z)-5-tert-butyl-3-[(2S)-piperidin-2-ylmethyl]-1,3-thiazol-2(3H)-ylidene]-5-chloro-2-methoxybenzamide;
N-[(2Z)-5-tert-butyl-3-[(2R)-piperidin-2-ylmethyl]-1,3-thiazol-2(3H)-ylidene]-5-chloro-2-methoxybenzamide;
N-[(2Z)-5-tert-butyl-3-{[(2S)-1-methylpyrrolidin-2-yl]methyl}-1,3-thiazol-2(3H)-ylidene]-5-chloro-2-methoxybenzamide;
N-[(2Z)-5-tert-butyl-3-{[(2S)-1-methylpiperidin-2-yl]methyl}-1,3-thiazol-2(3H)-ylidene]-5-chloro-2-methoxybenzamide;
N-[(2Z)-5-tert-butyl-3-{[(2R)-1-methylpiperidin-2-yl]methyl}-1,3-thiazol-2(3H)-ylidene]-5-chloro-2-methoxybenzamide;
N-[(2Z)-5-tert-butyl-3-{[(2R)-1-ethylpiperidin-2-yl]methyl}-1,3-thiazol-2(3H)-ylidene]-5-chloro-2-methoxybenzamide;
N-[(2Z)-5-tert-butyl-3-[(3R)-piperidin-3-ylmethyl]-1,3-thiazol-2(3H)-ylidene]-5-chloro-2-methoxybenzamide;
N-[(2Z)-5-tert-butyl-3-[(2R)-pyrrolidin-2-ylmethyl]-1,3-thiazol-2(3H)-ylidene]-5-chloro-2-methoxybenzamide;
N-[(2Z)-5-tert-butyl-3-[2-(2-oxopyrrolidin-1-yl)ethyl]-1,3-thiazol-2(3H)-ylidene]-5-chloro-2-methoxybenzamide;
N-[(2Z)-5-tert-butyl-3-[2-(2-oxopiperidin-1-yl)ethyl]-1,3-thiazol-2(3H)-ylidene]-5-chloro-2-methoxybenzamide;
N-[(2Z)-5-tert-butyl-3-[2-(2-oxoimidazolidin-1-yl)ethyl]-1,3-thiazol-2(3H)-ylidene]-5-chloro-2-methoxybenzamide;
(Z)—N-(5-tert-butyl-3-(2-sulfamoylethyl)thiazol-2(3H)-ylidene)-2-methoxy-5-(trifluoromethyl)benzamide;
N-[(2Z)-5-tert-butyl-3-{[1-(methylsulfonyl)azetidin-3-yl]methyl}-1,3-thiazol-2(3H)-ylidene]-2-{[(2S)-1-methylpyrrolidin-2-yl]methoxy}-5-(trifluoromethyl)benzamide;
5-chloro-2-methoxy-N-[(2Z)-5-methyl-3-{3-[(methylsulfonyl)amino]propyl}-1,3-thiazol-2(3H)-ylidene]benzamide;
5-chloro-2-methoxy-N-[(2Z)-5-methyl-3-[2-(4-methyl-1,3-thiazol-5-yl)ethyl]-1,3-thiazol-2(3H)-ylidene]benzamide;
2-[(tert-butylamino)oxy]-N-[(2Z)-5-tert-butyl-3-{[(2S)-5-oxopyrrolidin-2-yl]methyl}-1,3,4-thiadiazol-2(3H)-ylidene]-5-(trifluoromethyl)benzamide;
tert-butyl 2-[(2Z)-5-tert-butyl-2-[(5-chloro-2-methoxybenzoyl)imino]-1,3-thiazol-3(2H)-yl]ethylcarbamate;
N-[(2Z)-5-tert-butyl-3-[2-(methylamino)ethyl]-1,3-thiazol-2(3H)-ylidene]-5-chloro-2-methoxybenzamide;
2-(azetidin-3-yloxy)-N-[(2Z)-5-tert-butyl-3-{[1-(methylsulfonyl)azetidin-3-yl]methyl}-1,3-thiazol-2(3H)-ylidene]-5-(trifluoromethyl)benzamide;
5-chloro-N-[(2Z)-3-[(2-fluoropyridin-3-yl)methyl]-5-methyl-1,3-thiazol-2(3H)-ylidene]-2-methoxybenzamide;
N-[(2Z)-5-tert-butyl-3-{[(2R)-5-thioxopyrrolidin-2-yl]methyl}-1,3-thiazol 2(3H)-ylidene]-5-chloro-2-methoxybenzamide;
N-[(2Z)-5-tert-butyl-3-{[(2R)-5-thioxopyrrolidin-2-yl]methyl}-1,3,4-thiadiazol-2(3H)-ylidene]-5-chloro-2-methoxybenzamide;
N-[(2Z)-5-tert-butyl-3-{[(2S)-5-oxopyrrolidin-2-yl]methyl}-1,3,4-thiadiazol-2(3H)-ylidene]-2-methoxy-5-(trifluoromethyl)benzamide;
N-[(2Z)-5-tert-butyl-3-{[(2R)-5-oxopyrrolidin-2-yl]methyl}-1,3,4-thiadiazol-2(3H)-ylidene]-2-methoxy-5-(trifluoromethyl)benzamide;
N-[(2Z)-5-tert-butyl-3-[(1,3-dimethyl-1H-pyrazol-5-yl)methyl]-1,3-thiazol-2(3H)-ylidene]-5-chloro-2-methoxybenzamide;

N-[(2Z)-5-tert-butyl-3-{[(2S)-5-oxopyrrolidin-2-yl]methyl}-1,3,4-thiadiazol-2(3H)-ylidene]-2-{[(2S)-5-oxopyrrolidin-2-yl]methoxy}-5-(trifluoromethyl)benzamide;

N-[(2Z)-5-tert-butyl-3-{[(2S)-5-oxopyrrolidin-2-yl]methyl}-1,3-thiazol-2(3H)-ylidene]-2-{[(2S)-1-methylpyrrolidin-2-yl]methoxy}-5-(trifluoromethyl)benzamide;

N-[(2Z)-5-tert-butyl-3-{[(2S)-5-oxopyrrolidin-2-yl]methyl}-1,3-thiazol-2(3H)-ylidene]-2-fluoro-5-(trifluoromethyl)benzamide;

N-[(2Z)-5-tert-butyl-3-{[(2S)-5-oxopyrrolidin-2-yl]methyl}-1,3-thiazol-2(3H)-ylidene]-2-(pyridin-2-ylmethoxy)-5-(trifluoromethyl)benzamide;

2-[(2Z)-5-tert-butyl-2-[(5-chloro-2-methoxybenzoyl)imino]-1,3-thiazol-3(2H)-yl]ethyl carbamate; and 2-[(2Z)-2-{[2-azetidin-1-yl-5-(trifluoromethyl)benzoyl]imino}-5-tert-butyl-1,3-thiazol-3(2H)-yl]ethyl azetidine-1-carboxylate.

Compounds described herein may exist as stereoisomers wherein asymmetric or chiral centers are present. These stereoisomers are "R" or "S" depending on the configuration of substituents around the chiral carbon atom. The terms "R" and "S" used herein are configurations as defined in IUPAC 1974 Recommendations for Section E, Fundamental Stereochemistry, Pure Appl. Chem., 1976, 45: 13-30.

The various stereoisomers (including enantiomers and diastereomers) and mixtures thereof of the compounds described are also contemplated. Individual stereoisomers of compounds described may be prepared synthetically from commercially available starting materials that contain asymmetric or chiral centers or by preparation of racemic mixtures followed by resolution of the individual stereoisomer using methods that are known to those of ordinary skill in the art. Examples of resolution are, for example, (i) attachment of a mixture of enantiomers to a chiral auxiliary, separation of the resulting mixture of diastereomers by recrystallization or chromatography, followed by liberation of the optically pure product; or (ii) separation of the mixture of enantiomers or diastereomers on chiral chromatographic columns.

Geometric isomers may exist in the present compounds. All various geometric isomers and mixtures thereof resulting from the disposition of substituents around a carbon-carbon double bond, a carbon-nitrogen double bond, a cycloalkyl group, or a heterocycle group are contemplated. Substituents around a carbon-carbon double bond or a carbon-nitrogen bond are designated as being of Z or E configuration and substituents around a cycloalkyl or a heterocycle are designated as being of cis or trans configuration.

It is to be understood that compounds disclosed herein may exhibit the phenomenon of tautomerism.

Thus, the formulae drawings within this specification can represent only one of the possible tautomeric or stereoisomeric forms. It is to be understood that encompassed herein are any tautomeric or stereoisomeric form, and mixtures thereof, and is not to be limited merely to any one tautomeric or stereoisomeric form utilized within the naming of the compounds or formulae drawings.

c. Biological Data (i) In Vitro Methods—$CB_2$ and $CB_1$ Radioligand Binding Assays:

The $CB_1$ and $CB_2$ radioligand binding assays described herein are utilized to determine the selectivity of compounds for binding to $CB_2$ relative to $CB_1$ receptors.

HEK293 cells stably expressing human $CB_2$ receptors were grown until a confluent monolayer was formed. Briefly, the cells were harvested and homogenized in TE buffer (50 mM Tris-HCl, 1 mM $MgCl_2$, and 1 mM EDTA) using a polytron for 2×10 second bursts in the presence of protease inhibitors, followed by centrifugation at 45,000×g for 20 minutes. The final membrane pellet was re-homogenized in storage buffer (50 mM Tris-HCl, 1 mM $MgCl_2$, and 1 mM EDTA and 10% sucrose) and frozen at −78° C. until used. Saturation binding reactions were initiated by the addition of membrane preparation (protein concentration of 5 μg/well for human $CB_2$) into wells of a deep well plate containing [$^3$H] CP-55,940 (120 Ci/mmol, a nonselective CB agonist commercially available from Tocris) in assay buffer (50 mM Tris, 2.5 mM EDTA, 5 mM $MgCl_2$, and 0.5 mg/mL fatty acid free BSA, pH 7.4). After 90 min incubation at 30° C., binding reaction was terminated by the addition of 300 μL/well of cold assay buffer followed by rapid vacuum filtration through a UniFilter-96 GF/C filter plates (pre-soaked in 1 mg/mL BSA for 2 hours). The bound activity was counted in a TopCount using Microscint-20. Saturation experiments were conducted with twelve concentrations of [$^3$H]CP-55,940 ranging from 0.01 to 8 nM. Competition experiments were conducted with 0.5 nM [$^3$H]CP-55,940 and five concentrations of displacing ligands selected from the range of 0.01 nM to 10 μM. The addition of 10 μM unlabeled CP-55,940 (Tocris, Ellisville, Mo.) was used to assess nonspecific binding.

HEK293 cells stably expressing rat $CB_2$ receptors were grown until a confluent monolayer was formed. Briefly, the cells were harvested and homogenized in TE buffer (50 mM Tris-HCl, 1 mM $MgCl_2$, and 1 mM EDTA) using a polytron for 2×10 second bursts in the presence of protease inhibitors, followed by centrifugation at 45,000×g for 20 minutes. The final membrane pellet was re-homogenized in storage buffer (50 mM Tris-HCl, 1 mM $MgCl_2$, and 1 mM EDTA and 10% sucrose) and frozen at −78° C. until used. Saturation binding reactions were initiated by the addition of membrane preparation (protein concentration of 20 μg/well for rat $CB_2$) into wells of a deep well plate containing [$^3$H]CP-55,940 (120 Ci/mmol, a nonselective CB agonist commercially available from Tocris) in assay buffer (50 mM Tris, 2.5 mM EDTA, 5 mM $MgCl_2$, and 0.5 mg/mL fatty acid free BSA, pH 7.4). After 45 min incubation at 30° C., binding reaction was terminated by the addition of 300 μL/well of cold assay buffer followed by rapid vacuum filtration through a UniFilter-96 GF/C filter plates (pre-soaked in 1 mg/mL BSA for 2 hours). The bound activity was counted in a TopCount using Microscint-20. Saturation experiments were conducted with twelve concentrations of [$^3$H]CP-55,940 ranging from 0.01 to 8 nM. Competition experiments were conducted with 0.5 nM [$^3$H] CP-55,940 and five concentrations of displacing ligands selected from the range of 0.01 nM to 10 μM. The addition of 10 μM unlabeled CP-55,940 (Tocris, Ellisville, Mo.) was used to assess nonspecific binding.

Compounds tested were found to bind to $CB_2$ receptors with $K_i$ of less than about 1,000 nM, preferably less than 400 nM, more preferably less than 200 nM, and most preferably lower than 100 nM.

HEK293 human $CB_1$ membranes were purchased from Perkin Elmer. Binding was initiated by the addition of membranes (8-12 μg per well) into wells (Scienceware 96-well DeepWell plate, VWR, West Chester, Pa.) containing [$^3$H] CP-55,940 (120 Ci/mmol, Perkin Elmer, Boston, Mass.) and a sufficient volume of assay buffer (50 mM Tris, 2.5 mM EDTA, 5 mM $MgCl_2$, and 0.5 mg/mL fatty acid free BSA, pH 7.4) to bring the total volume to 250 μL. After incubation (30° C. for 90 minutes), binding was terminated by the addition of 300 μL per well of cold assay buffer and rapid vacuum filtration (FilterMate Cell Harvester, Perkin Elmer, Boston, Mass.) through a UniFilter-96 GF/C filter plate (Perkin Elmer, Boston, Mass.) (pre-soaked in 0.3% PEI at least 3 hours), followed by five washes with cold assay buffer. The bound activity was counted in the TopCount using Microscint-20 (both from Perkin Elmer, Boston, Mass.). Competition experiments were conducted with 1 nM [$^3$H]CP-55,940 and five concentrations (1 nM to 10 μM) of displacing ligands. The addition of 10 μM unlabeled CP-55,940 (Tocris, Ellisville, Mo.) was used to assess nonspecific binding. The compounds tested were found to bind to $CB_1$ receptors with $K_i$ of about 10 fold to about 1000 fold higher than that for $CB_2$ receptors. These results demonstrate that the compounds tested preferably bind to $CB_2$ vs. $CB_1$ receptors, and therefore are selective ligands for the CB2 receptor.

ii) In Vivo Data Animals

Adult male Sprague-Dawley rats (250-300 g body weight, Charles River Laboratories, Portage, Mich.) were used. Animal handling and experimental protocols were approved by the Institutional Animal Care and Use Committee (IACUC) at Abbott Laboratories. For all surgical procedures, animals were maintained under halothane anesthesia (4% to induce, 2% to maintain), and the incision sites were sterilized using a 10% povidone-iodine solution prior to and after surgeries.

Incision Model of Postoperative Pain

A skin incision model of postoperative pain was produced using the procedures described in Brennan et al., 1996, Pain, 64, 493. All rats were anesthetized with isofluorane delivered via a nose cone. Right hind paw incision was performed following sterilization procedures. The plantar aspect of the left hind paw was placed through a hole in a sterile plastic drape. A 1-cm longitudinal incision was made through the skin and fascia of the plantar aspect of the hind paw, starting 0.5 cm from the proximal edge of the heel and extending towards the toes, the plantar muscle was elevated and incised longitudinally leaving the muscle origin and insertion points intact. The skin was then closed with two mattress sutures (5-0 nylon). After surgery, animals were then allowed to recover for 2 hours, at which time tactile allodynia was assessed as described below. To evaluate the anti-nociceptive effects, animals were i.p. administered vehicle or test compound 90 minutes following skin incision and tactile allodynia was assessed 30 minutes after compound administration.

Tactile allodynia was measured using calibrated von Frey filaments (Stoelting, Wood Dale, Ill.) as described in Chaplan, S. R., F. W. Bach, J. W. Porgrel, J. M. Chung and T. L. Yaksh, 1994, Quantitative assessment of tactile allodynia in the rat paw, J. Neurosci. Methods, 53, 55. Rats were placed into inverted individual plastic cage (20×12.5×20 cm) on top of a suspended wire mesh grid, and acclimated to the test chambers for 20 minutes. The von Frey filaments were applied perpendicularly from underneath the cage through openings in the wire mesh floor directly to an area within 1-3 mm (immediately adjacent) of the incision, and then held in this position for approximately 8 seconds with enough force to cause a slight bend in the filament. Positive responses included an abrupt withdrawal of the hind paw from the stimulus, or flinching behavior immediately following removal of the stimulus. A 50% withdrawal threshold was determined using an up-down procedure as described in Dixon, W. J., 1980, Efficient analysis of experimental observations, Ann. Rev. Pharmacol. Toxicol., 20, 441.

Certain compounds tested in the incision model of postoperative pain showed a statistically significant change in paw withdrawal latency versus a saline vehicle at less than about 300 micromoles/kg. In a more preferred embodiment, compounds tested showed efficacy at less than about 50 micromoles/kg in the incision model of postoperative pain.

Capsaicin-Induced Secondary Mechanical Hypersensitivity:

Rats were allowed to acclimate to the study room for 1 hour. They were then briefly restrained, and capsaicin was administered at 10 μg in 10 μL of vehicle (10% ethanol and 2-hydroxypropyl cyclodextrin) by intraplantar injection into the center of the right hind paw. Secondary mechanical hyperalgesia was measured at the heel away from the site of injection at 180 min following capsaicin (Joshi et al 2006, Neuroscience 143, 587-596). Compounds were injected (i.p.) 30 min before testing (150 min post-capsaicin).

Tactile allodynia was measured as described above.

Certain compounds that were tested showed a statistically significant change in paw withdrawal latency versus a saline vehicle at less than about 300 micromoles/kg. In a more preferred embodiment, certain compounds showed efficacy of less than about 50 micromoles/kg.

MIA-Induced Knee Joint Osteoarthritic Pain Model

Unilateral knee joint osteoarthritis was induced in the rats by a single intra-articular (i.a.) injection of sodium monoiodoacetate (MIA, 3 mg in 0.05 mL sterile isotonic saline) into the right knee joint cavity under light isoflurane anesthesia using a 26G needle. The dose of the MIA (3 mg/i.a. injection) was selected based on results obtained from preliminary studies wherein an optimal pain behavior was observed at this dose. Pain behavioral assessment of hind limb grip force were conducted by recording the maximum compressive force exerted on the hind limb strain gauge setup, in a commercially available grip force measurement system (Columbus Instruments, Columbus, Ohio). The grip force data was converted to a maximum hindlimb cumulative compressive force (CFmax) (gram force)/kg body weight for each animal. The analgesic effects of test compounds were determined 20 days following the i.a. injection of MIA. The vehicle control group for each compound being tested was assigned 0% whereas the age matched naïve group was assigned as being 100% (normal). The % effects for each dose group was then expressed as % return to normalcy compared to the naïve group. Compounds were administered either orally (p.o.) or intraperitoneally (i.p.). The assessment of the analgesic effects of test compounds is typically made anytime between about 1 hour and about 5 hours following oral administration. The assessment of the analgesic effects of test compounds is typically made anytime between about 0.5 hour and about 2 hours following i.p. administration. Selection of the preferred time points for measuring the analgesic effects of test compounds is based upon consideration of the individual pharmacokinetic characteristics of test compounds in the rat. Time points known or expected to provide higher plasma concentrations of test compounds are preferred over those that were known or expected to provide lower concentrations. The assessment of the analgesic effects of test compounds can be made following a single dose or following repeated dosing of test compounds wherein the frequency of dosing is 1 to 2 times daily. The duration of such repeated daily dosing may last for any time greater than one day. A typical duration of repeated daily dosing is about 5 days to about 12 days.

A representative compound of formula (I) tested showed a statistically significant change in hind limb grip force strength versus a saline vehicle at less than about 50 micromoles/kg in the MIA model of osteoarthritic pain following a single oral dose.

d. Methods of Using the Compounds

One embodiment provides a method for treating pain (for example, inflammatory pain, osteoarthritic pain, neuropathic pain or nociceptive pain) in a mammal (including human) in need of such treatment. The method comprises administering to the mammal therapeutically effective amount of any of the compounds as described herein, or pharmaceutically acceptable salts or solvates thereof. The method further comprises administration of compounds described herein as a single dose. The method also comprises repeated or chronic administration of present compounds over a period of days, weeks, months, or longer. Compounds described herein may be administered alone, or in combination with one or more other compounds described herein, or in combination (i.e. co-administered) with one or more additional pharmaceutical agents. For example, one or more compound of formula (I), or pharmaceutically acceptable salts or solvates thereof, may be administered in combination with acetaminophen, or with one or more nonsteroidal anti-inflammatory drug (NSAID) such as, but not limited to, aspirin, diclofenac, diflusinal, etodolac, fenbufen, fenoprofen, flufenisal, flurbiprofen, ibuprofen, indomethacin, ketoprofen, ketorolac, meclofenamic acid, mefenamic acid, meloxicam, nabumetone, naproxen, nimesulide, nitroflurbiprofen, olsalazine, oxaprozin, phenylbutazone, piroxicam, sulfasalazine, sulindac, tolmetin and zomepirac; or administered with a combination of acetaminophen and one or more NSAID. In certain embodiments, the nonsteroidal anti-inflammatory drug (NSAID) is ibuprofen.

Another embodiment provides a method for treating a disorder selected from the group consisting of neurological disorders, cancers of the immune system, respiratory disorders, and cardiovascular disorders in a mammal in need of such treatment. The method comprises administering to the mammal therapeutically effective amount of one or more of the compound(s) described herein or pharmaceutically acceptable salts or solvates thereof.

Yet another embodiment relates to a method for providing neuroprotection in a mammal in need of such treatment. This method comprises administering to the mammal therapeutically effective amount of one or more compound(s) described herein or pharmaceutically acceptable salts or solvates thereof.

A further embodiment provides a method of increasing the therapeutic effectiveness or potency of compounds described herein by repeated or chronic administration of the compound(s) or the pharmaceutical composition over a period of days, weeks, or months.

In addition to the data contained herein, several lines of evidence support the assertion that $CB_2$ receptors play a role in analgesia. HU-308 is one of the first highly selective $CB_2$ agonists identified that elicits an antinociceptive response in the rat formalin model of persistent pain (Hanus, L., et al., Proc. Nat. Acad. Sci., 1999, 96, 14228-14233). The $CB_2$-selective cannabiniod ligand AM-1241 exhibits robust analgesic efficacy in animal models of acute thermal pain (Malan, T. P., et al., Pain, 2001, 93, 239-245; Ibrahim, M. M., et al., Proc. Nat. Acad. Sci., 2005, 102(8), 3093-3098), persistent pain (Hohmann, A. G., et al., J. Pharmacol. Exp. Ther., 2004, 308, 446-453), inflammatory pain (Nackley, A. G., et al., Neuroscience, 2003, 119, 747-757; Quartilho, A. et al., Anesthesiology, 2003, 99, 955-60), and neuropathic pain (Ibrahim, M. M., et al., Proc. Nat. Acad. Sci., 2003, 100, 10529-10533). The $CB_2$-selective partial agonist GW405833, also known as L768242, is efficacious in rodent models of neuropathic, incisional, and both chronic and acute inflammatory pain (Valenzano, K. J., et al., Neuropharmacology, 2005, 48, 658-672 and Clayton, N., et al., Pain, 2002, 96, 253-260).

The potential exists for $CB_2$ modulators to have opioid sparing effects. A synergy between the analgesic effects of morphine and the nonselective CB agonist $\Delta^9$-THC has been documented (Cichewicz, D. L., Life Sci. 2004, 74, 1317-1324). Therefore, $CB_2$ ligands have additive or synergistic analgesic effects when used in combination with lower doses of morphine or other opioids, providing a strategy for reducing adverse opioid events, such as tolerance, constipation, and respiratory depression, without sacrificing analgesic efficacy.

$CB_2$ receptors are present in tissues and cell types associated with immune functions and $CB_2$ receptor mRNA is expressed by human B cells, natural killer cells, monocytes, neutrophils, and T cells (Galiegue et al., Eur. J. Biochem., 1995, 232, 54-61). Studies with $CB_2$ knockout mice have suggested a role for $CB_2$ receptors in modulating the immune system (Buckley, N. E., et al., Eur. J. Pharmacol. 2000, 396, 141-149). Although immune cell development and differentiation are similar in knockout and wild type animals, the immunosuppressive effects of $\Delta^9$-THC are absent in the $CB_2$ receptor knockout mice, providing evidence for the involvement of $CB_2$ receptors in immunomodulation. As such, selective $CB_2$ modulators may be useful for the treatment of autoimmune diseases including but not limited to multiple sclerosis, rheumatoid arthritis, systemic lupus, myasthenia gravis, type I diabetes, irritable bowel syndrome, psoriasis, psoriatic arthritis, and hepatitis; and immune related disorders including but not limited to tissue rejection in organ transplants, gluten-sensitive enteropathy (Celiac disease), asthma, chronic obstructive pulmonary disease, emphysema, bronchitis, acute respiratory distress syndrome, allergies, allergic rhinitis, dermatitis, and Sjogren's syndrome.

Microglial cells are considered to be the immune cells of the central nervous system (CNS) where they regulate the initiation and progression of immune responses. $CB_2$ receptor expression on microglia is dependent upon inflammatory state with higher levels of $CB_2$ found in primed, proliferating, and migrating microglia relative to resting or fully activated microglial (Carlisle, S. J., et al. Int. Immunopharmacol., 2002, 2, 69). Neuroinflammation induces many changes in microglia cell morphology and there is an upregulation of $CB_2$ receptors and other components of the endocannabinoid system.—Neuroinflammation occurs in several neurodegenerative diseases, and induction of microglial $CB_2$ receptors has been observed (Carrier, E. J., et al., Current Drug Targets—CNS & Neurological Disorders, 2005, 4, 657-665). Thus, $CB_2$ ligands may be clinically useful for the treatment of neuroinflammation.

Multiple sclerosis is common immune-mediated disease of the CNS in which the ability of neurons to conduct impulses becomes impaired through demyelination and axonal damage. The demyelination occurs as a consequence of chronic inflammation and ultimately leads to a broad range of clinical symptoms that fluctuate unpredictably and generally worsen with age. These include painful muscle spasms, tremor, ataxia, motor weakness, sphincter dysfunction, and difficulty speaking (Pertwee, R. G., Pharmacol. Ther. 2002, 95, 165-174). The $CB_2$ receptor is up-regulated on activated microglial cells during experimental autoimmune encephalomyelitis (EAE) (Maresz, K., et al., J. Neurochem. 2005, 95, 437-445). $CB_2$ receptor activation prevents the recruitment of inflammatory cells such as leukocytes into the CNS (Ni, X., et al., Multiple Sclerosis, 2004, 10, 158-164) and plays a protective role in experimental, progressive demyelination (Arevalo-Martin, A.; et al., J. Neurosci., 2003, 23(7), 2511-2516), which are critical features in the development of multiple sclerosis. Thus, $CB_2$ receptor modulators may provide a unique treatment for demyelinating pathologies.

Alzheimer's disease is a chronic neurodegenerative disorder accounting for the most common form of elderly dementia. Recent studies have revealed that $CB_2$ receptor expression is upregulated in neuritic plaque-associated microglia from brains of Alzheimer's disease patients (Benito, C., et al., J. Neurosci., 2003, 23(35), 11136-11141). In vitro, treatment with the $CB_2$ agonist JWH-133 abrogated β-amyloid-induced microglial activation and neurotoxicity, effects that can be blocked by the $CB_2$ antagonist SR144528 (Ramirez, B. G., et al., J. Neurosci. 2005, 25(8), 1904-1913). $CB_2$ modulators may possess both anti-inflammatory and neuroprotective actions and thus have clinical utility in treating neuroinflammation and in providing neuroprotection associated with the development of Alzheimer's disease.

Increased levels of epithelial $CB_2$ receptor expression are observed in human inflammatory bowel disease tissue (Wright, K., et al., Gastroenterology, 2005, 129, 437-453). Activation of $CB_2$ receptors re-established normal gastrointestinal transit after endotoxic inflammation was induced in rats (Mathison, R., et al., Br. J. Pharmacol. 2004, 142, 1247-1254). $CB_2$ receptor activation in a human colonic epithelial cell line inhibited TNF-α-induced interleukin-8 (IL-8) release (Ihenetu, K. et al., Eur. J. Pharmacol. 2003, 458, 207-215). Chemokines released from the epithelium, such as the neutrophil chemoattractant IL-8, are upregulated in inflammatory bowel disease (Warhurst, A. C., et al., Gut, 1998, 42, 208-213). Thus, administration of $CB_2$ receptor modulators may represent a novel approach for the treatment of inflammation and disorders of the gastrointestinal tract including but not limited to inflammatory bowel disease, irritable bowel syndrome, secretory diarrhea, ulcerative colitis, Crohn's disease and gastroesophageal reflux disease (GERD).

Hepatic fibrosis occurs as a response to chronic liver injury and ultimately leads to cirrhosis, which is a major worldwide health issue due to the severe accompanying complications of portal hypertension, liver failure, and hepatocellular carcinoma (Lotersztajn, S., et al., Annu. Rev. Pharmacol. Toxicol., 2005, 45, 605-628). Although $CB_2$ receptors were not detectable in normal human liver, $CB_2$ receptors were expressed liver biopsy specimens from patients with cirrhosis. Activation of $CB_2$ receptors in cultured hepatic myofibroblasts produced potent antifibrogenic effects (Julien, B., et al., Gastroenterology, 2005, 128, 742-755). In addition, $CB_2$ knockout mice developed enhanced liver fibrosis after chronic administration of carbon tetrachloride relative to wild-type mice. Administration of $CB_2$ receptor modulators may represent a unique approach for the treatment of liver fibrosis.

Cough is a dominant and persistent symptom of many inflammatory lung diseases, including asthma, chronic obstructive pulmonary disease, viral infections, and pulmonary fibrosis (Patel, H. J., et al., Brit. J. Pharmacol., 2003, 140, 261-268). Recent studies have provided evidence for the existence of neuronal $CB_2$ receptors in the airways, and have demonstrated a role for $CB_2$ receptor activation in cough suppression (Patel, H. J., et al., Brit. J. Pharmacol., 2003, 140, 261-268 and Yoshihara, S., et al., Am. J. Respir. Crit. Care Med., 2004, 170, 941-946). Both exogenous and endogenous cannabinoid ligands inhibit the activation of C-fibers via $CB_2$ receptors and reduce neurogenic inflammatory reactions in airway tissues (Yoshihara, S., et al., J. Pharmacol. Sci. 2005, 98(1), 77-82; Yoshihara, S., et al., Allergy and Immunology, 2005, 138, 80-87). Thus, $CB_2$-selective modulators may have utility as antitussive agents for the treatment of pulmonary inflammation, chronic cough, and a variety of airway inflammatory diseases including but not limited to asthma, chronic obstructive pulmonary disease, and pulmonary fibrosis.

There is a substantial genetic contribution to bone mass density and the $CB_2$ receptor gene is associated with human osteoporosis (Karsak, M., et al., Human Molecular Genetics, 2005, 14(22), 3389-3396). Osteoclasts and osteoblasts are largely responsible for maintaining bone structure and function through a process called remodeling, which involves resorption and synthesis of bone (Boyle, W. J., et al., Nature, 2003, 423, 337-342). $CB_2$ receptor expression has been detected on osteoclasts and osteoblastic precursor cells, and administration of a $CB_2$ agonist in mice caused a dose-dependent increase in bone formation (Grotenhermen, F. and Muller-Vahl, K., Expert Opin. Pharmacother., 2003, 4(12), 2367-2371). Cannabinoid inverse agonists, including the $CB_2$-selective inverse agonist SR144528, have been shown to inhibit osteoclast activity and reverse ovariectomy-induced bone loss in mice, which is a model for post-menopausal osteoporosis (Ralston, S. H., et al., Nature Medicine, 2005, 11, 774-779). Thus, $CB_2$ modulators may be useful for the treatment and prevention of osteoporosis, osteoarthritis, and bone disorders.

Artherosclerosis is a chronic inflammatory disease and is a leading cause of heart disease and stroke. $CB_2$ receptors have been detected in both human and mouse atherosclerotic plaques. Administration of low doses of THC in apolipoprotein E knockout mice slowed the progression of atherosclerotic lesions, and these effects were inhibited by the $CB_2$-selective antagonist SR144528 (Steffens, S., et al., Nature, 2005, 434, 782-786). Thus, compounds with activity at the $CB_2$ receptor may be clinically useful for the treatment of atherosceloris.

$CB_2$ receptors are expressed on malignant cells of the immune system and targeting $CB_2$ receptors to induce apoptosis may constitute a novel approach to treating malignancies of the immune system. Selective $CB_2$ agonists induce regression of malignant gliomas (Sanchez, C., et al., Cancer Res., 2001, 61, 5784-5789), skin carcinomas (Casanova, M. L., et al., J. Clin. Invest., 2003, 111, 43-50), and lymphomas (McKallip, R. J., et al., Blood, 2002, 15(2), 637-634). Thus, $CB_2$ modulators may have utility as anticancer agents against tumors of immune origin.

Activation of $CB_2$ receptors has been demonstrated to protect the heart against the deleterious effects of ischemia and reperfusion (Lepicier, P., et al., Brit. J. Pharm. 2003, 139, 805-815; Bouchard, J.-F., et al., Life Sci. 2003, 72, 1859-1870; Filippo, C. D., et al., J. Leukoc. Biol. 2004, 75, 453-459). Thus, $CB_2$ modulators may have utility for the treatment or prophylaxis of cardiovascular disease and the development of myocardial infarction.

Actual dosage levels of active ingredients in the pharmaceutical compositions can be varied so as to obtain an amount of the active compound(s) that is effective to achieve the desired therapeutic response for a particular patient, compositions and mode of administration. The selected dosage level will depend upon the activity of the particular compound, the route of administration, the duration of treatment, the severity of the condition being treated and the condition and prior medical history of the patient being treated. However, it is within the skill of the art to start doses of the compound at levels lower than required to achieve the desired therapeutic effect and to gradually increase the dosage until the desired effect is achieved. In the treatment of certain medical conditions, repeated or chronic administration of compounds may be required to achieve the desired therapeutic response. "Repeated or chronic administration" refers to the administration of compounds daily (i.e., every day) or intermittently (i.e., not every day) over a period of days, weeks, months, or longer. In particular, the treatment of chronic painful conditions is anticipated to require such repeated or chronic administration of the compounds. Compounds described herein may become more effective upon repeated or chronic administration such that the therapeutically effective doses on repeated or chronic administration may be lower than the therapeutically effective dose from a single administration.

Combination therapy includes administration of a single pharmaceutical dosage formulation containing one or more of the compounds described herein and one or more additional pharmaceutical agents, as well as administration of the compounds and each additional pharmaceutical agent, in its own separate pharmaceutical dosage formulation. For example, a compound described herein and one or more additional pharmaceutical agents, may be administered to the patient together, in a single oral dosage composition having a fixed ratio of each active ingredient, such as a tablet or capsule; or each agent may be administered in separate oral dosage formulations.

Where separate dosage formulations are used, present compounds and one or more additional pharmaceutical agents may be administered at essentially the same time (e.g., concurrently) or at separately staggered times (e.g., sequentially).

Compounds described herein can also be administered as a pharmaceutical composition comprising the compounds of interest in combination with one or more pharmaceutically acceptable carriers. The phrase "therapeutically effective amount" of the present compounds means sufficient amounts of the compounds to treat disorders, at a reasonable benefit/risk ratio applicable to any medical treatment. It will be understood, however, that the total daily usage of the compounds and compositions will be decided by the attending physician within the scope of sound medical judgment. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well-known in the medical arts. For example, it is well within the skill of the art to start doses of the compound at levels lower than required to achieve the desired therapeutic effect and to gradually increase the dosage until the desired effect is achieved.

The total daily dose of the compounds administered to a human or other animal range from about 0.01 mg/kg body weight to about 100 mg/kg body weight. More preferable doses can be in the range of from about 0.03 mg/kg body weight to about 30 mg/kg body weight. If desired, the effective daily dose can be divided into multiple doses for purposes of administration. Consequently, single dose compositions may contain such amounts or submultiples thereof to make up the daily dose. It is understood that the effective daily dose may vary with the duration of the treatment.

e. Pharmaceutical Compositions

Pharmaceutical compositions comprise compounds described herein or pharmaceutically acceptable salts or solvates thereof are also described. The pharmaceutical compositions comprising compounds described herein may be formulated together with one or more non-toxic pharmaceutically acceptable carriers.

Another aspect relates to pharmaceutical compositions comprising present compounds, or pharmaceutically acceptable salts or solvates thereof, and one or more pharmaceutically acceptable carriers, alone or in combination with one or more nonsteroidal anti-inflammatory drug (NSAID), or other analgesics (for example, acetaminophen), or combinations thereof.

The pharmaceutical compositions can be administered to humans and other mammals orally, rectally, parenterally, intracisternally, intravaginally, intraperitoneally, topically (as by powders, ointments or drops), bucally or as an oral or nasal spray. The term "parenterally" as used herein, refers to modes of administration which include intravenous, intramuscular, intraperitoneal, intrasternal, subcutaneous and intraarticular injection and infusion.

The term "pharmaceutically acceptable carrier" as used herein, means a non-toxic, inert solid, semi-solid or liquid filler, diluent, encapsulating material or formulation auxiliary of any type. Some examples of materials which can serve as pharmaceutically acceptable carriers are sugars such as, but not limited to, lactose, glucose and sucrose; starches such as, but not limited to, corn starch and potato starch; cellulose and its derivatives such as, but not limited to, sodium carboxymethyl cellulose, ethyl cellulose and cellulose acetate; powdered tragacanth; malt; gelatin; talc; excipients such as, but not limited to, cocoa butter and suppository waxes; oils such as, but not limited to, peanut oil, cottonseed oil, safflower oil, sesame oil, olive oil, corn oil and soybean oil; glycols; such a propylene glycol; esters such as, but not limited to, ethyl oleate and ethyl laurate; agar; buffering agents such as, but not limited to, magnesium hydroxide and aluminum hydroxide; alginic acid; pyrogen-free water; isotonic saline; Ringer's solution; ethyl alcohol, and phosphate buffer solutions, as well as other non-toxic compatible lubricants such as, but not limited to, sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Pharmaceutical compositions for parenteral injection comprise pharmaceutically acceptable sterile aqueous or non-aqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), vegetable oils (such as olive oil), injectable organic esters (such as ethyl oleate) and suitable mixtures thereof. Proper fluidity can be maintained, for example, by the use of coating materials such as lecithin, by the maintenance of the required particle size in the case of dispersions and by the use of surfactants.

These compositions may also contain adjuvants such as preservatives, wetting agents, emulsifying agents and dispersing agents. Prevention of the action of microorganisms can be ensured by the inclusion of various antibacterial and antifungal agents, for example, paraben, chlorobutanol, phenol sorbic acid and the like. It may also be desirable to include isotonic agents such as sugars, sodium chloride and the like. Prolonged absorption of the injectable pharmaceutical form can be brought about by the inclusion of agents which delay absorption such as aluminum monostearate and gelatin.

In some cases, in order to prolong the effect of the drug, it is desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution which, in turn, may depend upon crystal size and crystalline form.

Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Solid dosage forms for oral administration include capsules, tablets, pills, powders and granules. In such solid dosage forms, the active compound may be mixed with at least one inert, pharmaceutically acceptable excipient or carrier, such as sodium citrate or dicalcium phosphate and/or a) fillers or extenders such as starches, lactose, sucrose, glucose, mannitol and silicic acid; b) binders such as carboxymethylcellulose, alginates, gelatin, polyvinylpyrrolidone, sucrose and acacia; c) humectants such as glycerol; d) disintegrating agents such as agar-agar, calcium carbonate, potato or tapioca starch, alginic acid, certain silicates and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay and i) lubricants such as talc, calcium stearate, magnesium stearate, solid polyethylene glycols, sodium lauryl sulfate and mixtures thereof. In the case of capsules, tablets and pills, the dosage form may also comprise buffering agents.

Solid compositions of a similar type may also be employed as fillers in soft and hard-filled gelatin capsules using such carriers as lactose or milk sugar as well as high molecular weight polyethylene glycols and the like.

The solid dosage forms of tablets, dragees, capsules, pills and granules can be prepared with coatings and shells such as enteric coatings and other coatings well-known in the pharmaceutical formulating art. They may optionally contain opacifying agents and may also be of a composition such that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned carriers.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor and sesame oils), glycerol, tetrahydrofurfuryl alcohol, polyethylene glycols and fatty acid esters of sorbitan and mixtures thereof.

Besides inert diluents, the oral compositions may also include adjuvants such as wetting agents, emulsifying and suspending agents, sweetening, flavoring and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, tragacanth and mixtures thereof.

Compositions for rectal or vaginal administration are preferably suppositories which can be prepared by mixing the compounds with suitable non-irritating carriers or carriers such as cocoa butter, polyethylene glycol or a suppository wax which are solid at room temperature but liquid at body temperature and therefore melt in the rectum or vaginal cavity and release the active compound.

The compounds can also be administered in the form of liposomes. As is known in the art, liposomes are generally derived from phospholipids or other lipid substances. Liposomes are formed by mono- or multi-lamellar hydrated liquid crystals which are dispersed in an aqueous medium. Any non-toxic, physiologically acceptable and metabolizable lipid capable of forming liposomes can be used. The present compositions in liposome form can contain, in addition to compounds described herein, stabilizers, preservatives, excipients and the like. The preferred lipids are natural and synthetic phospholipids and phosphatidyl cholines (lecithins) used separately or together.

Methods to form liposomes are known in the art. See, for example, Prescott, Ed., Methods in Cell Biology, Volume XIV, Academic Press, New York, N.Y. (1976), p. 33 et seq.

Dosage forms for topical administration of compounds described herein include powders, sprays, ointments and inhalants. The active compounds may be mixed under sterile conditions with a pharmaceutically acceptable carrier and any needed preservatives, buffers or propellants which may be required. Ophthalmic formulations, eye ointments, powders and solutions are also contemplated as being within the scope.

The compounds can be used in the form of pharmaceutically acceptable salts derived from inorganic or organic acids. The phrase "pharmaceutically acceptable salt" means those salts which are, within the scope of sound medical judgment, suitable for use in contact with the tissues of humans and lower animals without undue toxicity, irritation, allergic response and the like and are commensurate with a reasonable benefit/risk ratio.

Pharmaceutically acceptable salts are well known in the art. For example, S. M. Berge et al. describe pharmaceutically acceptable salts in detail in (J. Pharmaceutical Sciences, 1977, 66: 1 et seq). The salts can be prepared in situ during the final isolation and purification of the compounds or separately by reacting a free base function with a suitable organic acid. Representative acid addition salts include, but are not limited to acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, fumarate, hydrochloride, hydrobromide, hydroiodide, 2-hydroxyethanesulfonate (isothionate), lactate, malate, maleate, methanesulfonate, nicotinate, 2-naphthalenesulfonate, oxalate, palmitoate, pectinate, persulfate, 3-phenylpropionate, picrate, pivalate, propionate, succinate, tartrate, thiocyanate, phosphate, glutamate, bicarbonate, p-toluenesulfonate and undecanoate. Also, the basic nitrogen-containing groups can be quaternized with such agents as lower alkyl halides such as, but not limited to, methyl, ethyl, propyl, and butyl chlorides, bromides and iodides; dialkyl sulfates like dimethyl, diethyl, dibutyl and diamyl sulfates; long chain halides such as, but not limited to, decyl, lauryl, myristyl and stearyl chlorides, bromides and iodides; arylalkyl halides like benzyl and phenethyl bromides and others. Water or oil-soluble or dispersible products are thereby obtained. Examples of acids which can be employed to form pharmaceutically acceptable acid addition salts include such inorganic acids as hydrochloric acid, hydrobromic acid, sulfuric acid, and phosphoric acid and such organic acids as acetic acid, fumaric acid, maleic acid, 4-methylbenzenesulfonic acid, succinic acid and citric acid.

Basic addition salts can be prepared in situ during the final isolation and purification of compounds by reacting a carboxylic acid-containing moiety with a suitable base such as, but not limited to, the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as, but not limited to, lithium, sodium, potassium, calcium, magnesium and aluminum salts and the like and nontoxic quaternary ammonia and amine cations including ammonium, tetramethylammonium, tetraethylammonium, methylamine, dimethylamine, trimethylamine, triethylamine, diethylamine, ethylamine and the like. Other representative organic amines useful for the formation of base addition salts include ethylenediamine, ethanolamine, diethanolamine, piperidine, piperazine and the like.

The term "pharmaceutically acceptable prodrug" or "prodrug" as used herein, represents those prodrugs of the compounds which are, within the scope of sound medical judgment, suitable for use in contact with the tissues of humans and lower animals without undue toxicity, irritation, allergic response, and the like, commensurate with a reasonable benefit/risk ratio, and effective for their intended use.

Contemplated also are compounds formed by synthetic means or formed by in vivo biotransformation of a prodrug.

Compounds described herein can exist in unsolvated as well as solvated forms, including hydrated forms, such as hemi-hydrates. In general, the solvated forms, with pharmaceutically acceptable solvents such as water and ethanol among others are equivalent to the unsolvated forms.

f. General Synthesis

Encompassed herein are compounds prepared by synthetic processes or by metabolic processes. Preparation of the compounds by metabolic processes includes those occurring in the human or animal body (in vivo) or processes occurring in vitro.

Compounds described herein can be prepared by a variety of processes well known for the preparation of compounds of this class. For example, the compounds of formula (I) wherein the groups X, n, $R^1$, $R^2$, $R^3$, $R^4$, $R^{21a}$, $R^{25a}$, $R^{26a}$, $R^{101a}$, $R^{102a}$, $R^{101d}$, $R^{102d}$, $R^{105a}$, $R^{105b}$, and $R^{105}$ have the meanings as set forth in the summary section unless otherwise noted, can be prepared by general procedures such as, but not limited to, those outlined in Schemes 1-9.

As used in the descriptions of the schemes and the examples, certain abbreviations are intended to have the following meanings: HPLC for high performance liquid chromatography or high pressure liquid chromatography, Boc for tert-butoxycarbonyl, DBU for 1,8-diazabicyclo[5.4.0]undec-7-ene; DMSO for dimethylsulfoxide, OMs or mesylate for methanesulfonate, and OTs or tosylate for p-toluenesulfonate.

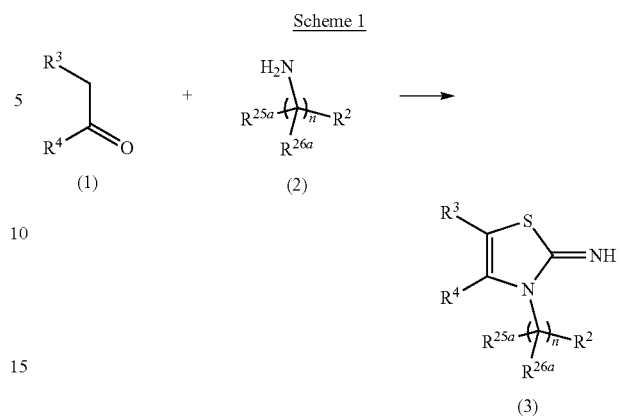

Scheme 1

Compounds of formula (3) may be prepared according to the sequence outlined in Scheme 1. Carbonyl compounds (1) can be reacted at room temperature with amino compounds (2) in a suitable solvent such as, but not limited to, acetonitrile, tetrahydrofuran, or dichloromethane for a period of about 1 hour to about 24 hours in the presence of a dehydrating agent such as, but not limited to, 4 Å molecular sieves; followed by the addition of potassium thiocyanate and iodine with heating at about 50° C. for a period of about 4 hours to about 24 hours to provide the compounds (3).

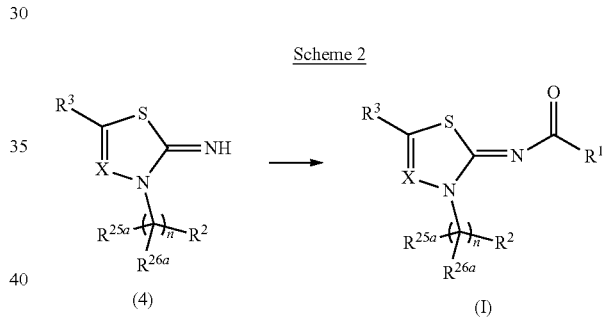

Scheme 2

Compounds of general formula (4) can be converted to the compounds of formula (I) as outlined in Scheme 2 by reaction with an acid chloride ($R^1COCl$) or carboxylic acid ($R^1CO_2H$) under appropriate conditions. For example, intermediates (4) can be reacted with $R^1COCl$ in a solvent such as, but not limited to, tetrahydrofuran, dimethylformamide, or dichloromethane at a temperature from about 25° C. to about 50° C. in the presence of a base such as, but not limited to, triethylamine, diisopropylethylamine, or potassium carbonate, and optionally in the presence of a catalyst such as 4-dimethylaminopyridine. Alternatively, intermediates (4) can be reacted with $R^1CO_2H$ in a solvent such as, but not limited to, tetrahydrofuran or dimethylformamide, in the presence of a coupling reagent such as 1,1'-carbonyldiimidazole (CDI), bis (2-oxo-3-oxazolidinyl)phosphinic chloride (BOPCl), 1,3-dicyclohexylcarbodiimide (DCC), polymer supported 1,3-dicyclohexylcarbodiimide (PS-DCC), O-(7-azabenzotriazol-1-yl)-N,N,N',N'-tetramethyluronium hexafluorophosphate (HATU), O-benzotriazol-1-yl-N,N,N',N'-tetramethyluronium tetrafluoroborate (TBTU), or 1-propanephosphonic acid cyclic anhydride, and in the presence or absence of a coupling auxiliary such as, but not limited to, 1-hydroxy-7-azabenzotriazole (HOAT), or 1-hydroxybenzotriazole hydrate (HOBT). The reaction is generally conducted in the presence or absence of a base such as, but not limited to, N-methyl morpholine, triethylamine, or diisopropylethylamine.

Scheme 3

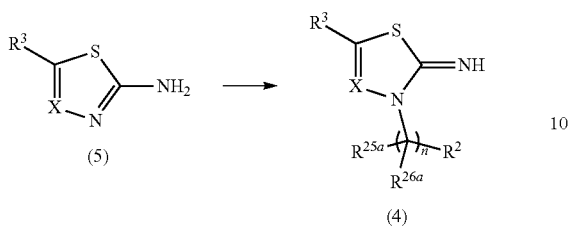

Compounds (4) may be prepared using the sequence outlined in Scheme 3. Amino compounds of formula (5) can be reacted with compounds of formula $R^2$—$(CR^{25a}R^{26a})_n$—$X^{201}$, wherein $X^{201}$ is Cl, Br, I, OTs, or OMs, to form compounds (4). This reaction may be performed either neat or in a solvent such as, but not limited to, tetrahydrofuran, dimethylformamide, dimethylsulfoxide, or dioxane, at about room temperature or up to about 150° C., and optionally in the presence of a catalyst such as, but not limited to, tetrabutylammonium iodide or sodium iodide. In certain cases, it may be beneficial to conduct this reaction in the presence of a base such as, but not limited to, triethylamine, potassium carbonate, potassium tert-butoxide, or sodium hydride.

Scheme 4

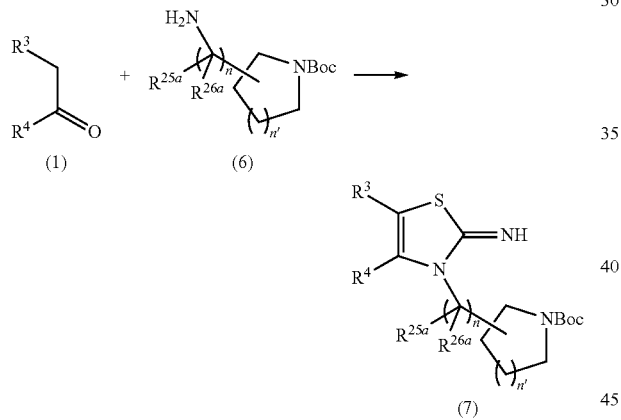

Compounds of formula (7) wherein n' is 0, 1, 2, 3, or 4, may be prepared according to the sequence outlined in Scheme 4. Carbonyl compounds (1) can be reacted at room temperature with amino compounds (6) using the reaction conditions outlined in Scheme 1 for the conversion of (1) to (3), to provide intermediates (7).

Scheme 5

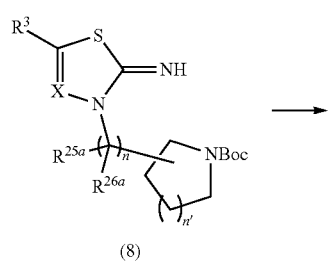

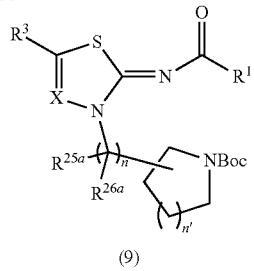

Using the methods provided above in Scheme 2 for the conversion of the intermediates (4) to compounds of formula (I), intermediates (8) wherein n' is 0, 1, 2, 3, or 4, can be converted to compounds (9) as outlined in Scheme 5.

Scheme 6

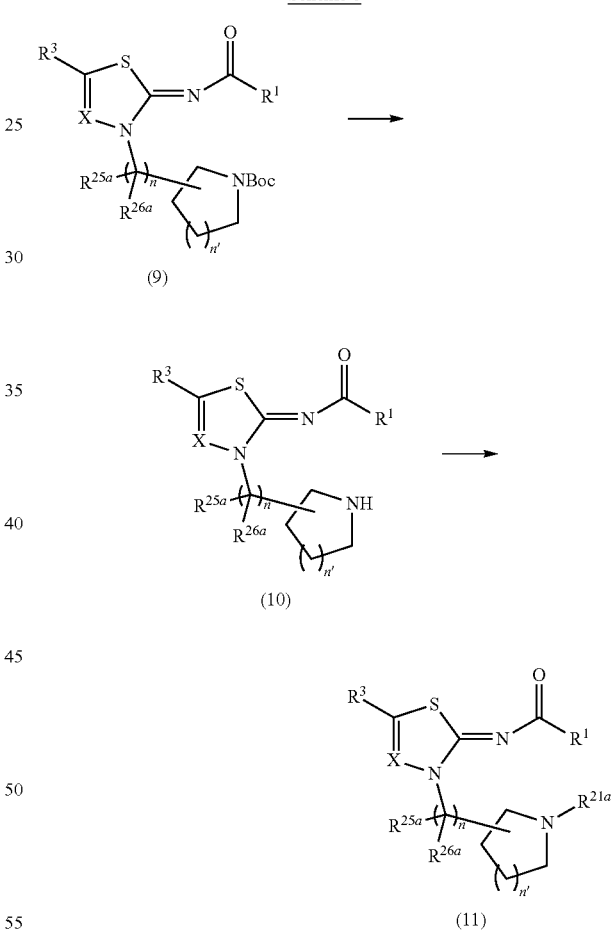

Amine compounds of formulae (10) and (11) may be prepared according to the sequence outlined in Scheme 6. Compounds (9) wherein n' is 0, 1, 2, 3, or 4, can be converted to compounds (10) by treatment with an acid such as, but not limited to, trifluoroacetic acid or hydrochloric acid, in a solvent such as but not limited to dichloromethane at temperatures ranging from about 0° C. to about room temperature. Amine compounds (10) can be converted to amine compounds (11) wherein $R^{21a}$ is alkyl by reactions known in the art. For example, the conversion can be achieved via reductive amination reaction with a suitable aldehyde or ketone in the presence of a reducing agent such as sodium triacetoxyhydroborate or sodium cyanoborohydride, in a solvent such as acetonitrile and the like. When treated with reagents of formula $ClSO_2R^{105c}$ in a solvent such as, but not limited to, tetrahydrofuran or dichloromethane, and in the presence of a base such as triethylamine, diisopropylethylamine, or DBU, at a temperature ranging from about 0° C. to about room temperature, compound (10) can be transformed into compounds (11) wherein $R^{21a}$ is $SO_2R^{105c}$.

Similarly compounds (10) can be reacted with reagents such as $ClCOR^{105d}$ (wherein $R^{105d}$ is other than hydrogen), $ClC(O)OR^{105c}$, $ClCONR^{101d}R^{102d}$, and $O=C=NR^{101d}$ to provide compounds (11) wherein $R^{21a}$ is $COR^{105d}$ (wherein $R^{105d}$ is other than hydrogen), $C(O)OR^{105c}$, and $CONR^{101d}R^{102d}$ respectively.

Compounds of formula (I) may also be prepared according to the sequence outlined in Scheme 7. Compounds (5) can be converted to compounds (12) using the conditions described in Scheme 2 for the conversion of compounds (4) to compounds of formula (I). Compounds (12) can be converted to compounds of formula (I) using conditions similar to those described in Scheme 3 for the conversion of compounds (5) to compounds (4). Compounds (12) can also be converted to compounds of formula (I) using phase transfer conditions, for example: refluxing of compound (12) with compounds of formula $R^2(CR^{25a}R^{26a})_n$—$X^{201}$, wherein $X^{201}$ is Cl, Br, I, OTs, or OMs in toluene, in the presence of a base like potassium carbonate. Examples of phase transfer agents include, but are not limited to, tetrabutylammonium iodide, tetrabutylammonium hydrogensulfate, tetraethylammonium iodide, and the like.

Scheme 8

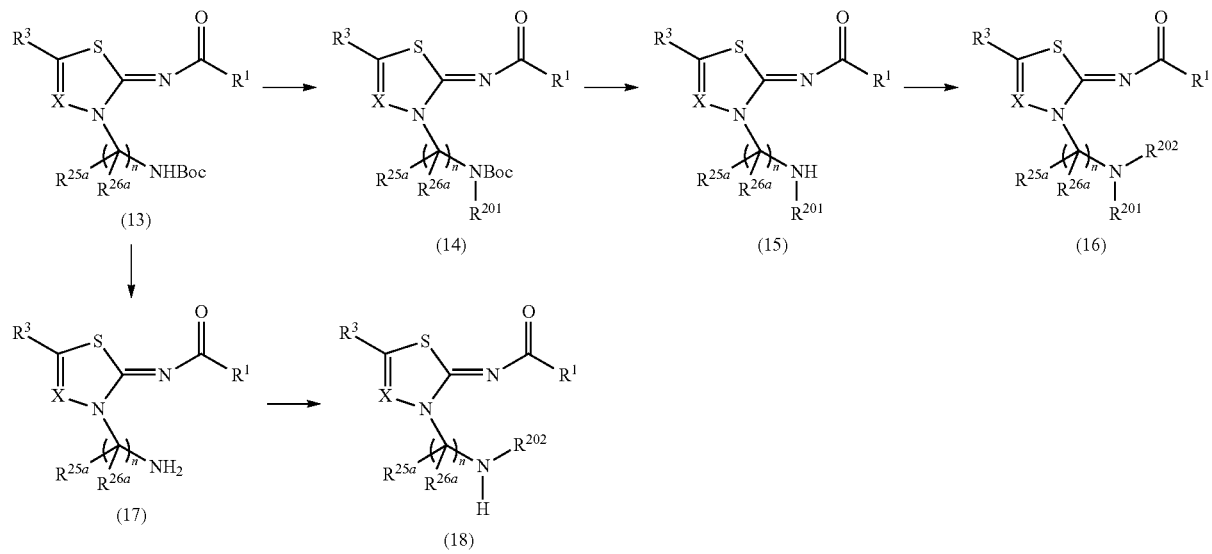

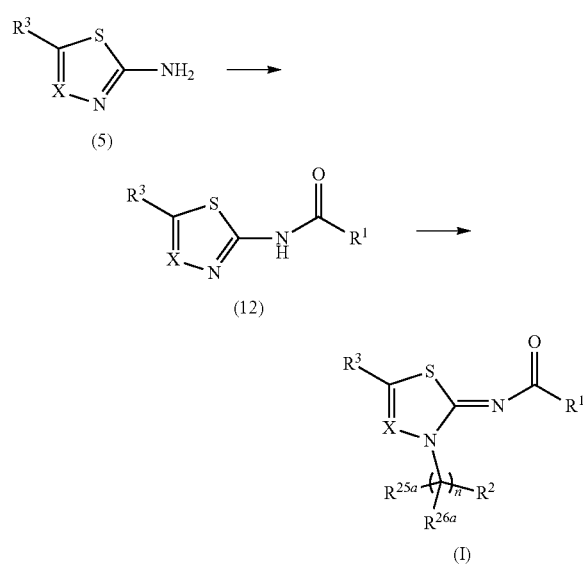

Scheme 7

Compounds of formula (15), (16), (17) and (18) may be prepared according to the sequences outlined in Scheme 8. Compounds (13) can be converted to compounds (14) by reaction with a reagent $R^{201}$—$X^{201}$, wherein $R^{201}$ is $R^{23a}$, $R^{23b}$, or $R^{23c}$ (each of which is independently alkyl, haloalkyl, alkoxyalkyl, or haloalkoxyalkyl), and $X^{201}$ is Cl, Br, I, OTs, or OMs, in solvents such as, but not limited to, tetrahydrofuran, or dimethylformamide, and in the presence of a base such as, but not limited to, sodium hydride, potassium carbonate, or potassium tert-butoxide. Compounds (14) can be transformed to compounds (15) by treatment with an acid such as, but not limited to, trifluoroacetic acid or hydrochloric acid, in solvents such as, but not limited to, dichloromethane at temperatures ranging from about 0° C. to about room temperature.

Compounds (13) can be transformed to compounds (17) by removal of the Boc protecting group using similar conditions to those described for the conversion of compounds (14) to compounds (15).

Compounds (15) and (17) can be converted to compounds (16) and (18) wherein $R^{202}$ is —$SO_2R^{105a}$, respectively, by treatment with reagents $ClSO_2R^{105a}$ in a solvent such as, but not limited to, tetrahydrofuran or dichloromethane, in the presence of a base such as triethylamine, diisopropylethylamine, or DBU, at a temperature ranging from about 0° C. to about room temperature.

Similarly, compounds (15) and (17) can be converted to compounds (16) and (18) wherein $R^{202}$ is —$COR^{105b}$, —$C(O)OR^{105b}$, or —$CONR^{101a}R^{102a}$, respectively, by reacting with reagents such as $ClCOR^{105b}$, $ClC(O)OR^{105b}$, $ClCONR^{101a}R^{102a}$, or $O=C=NR^{101a}$.

Scheme 9

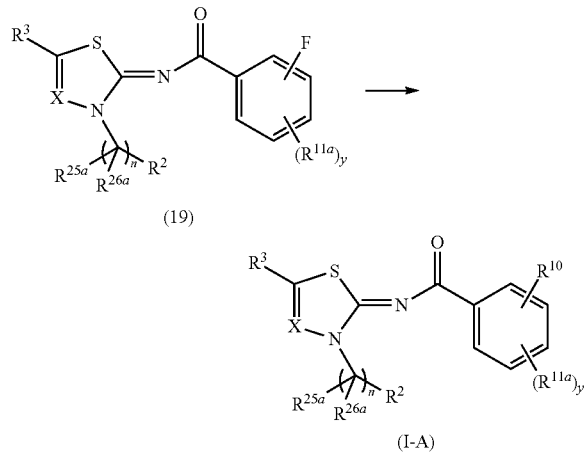

Compounds of formula (I-A), wherein y is 0, 1, or 2; $R^2$, $R^3$, $R^{25a}$, $R^{26a}$, $R^{11a}$, X, and n are as defined in formula (I); and $R^{10}$ is alkoxy, alkoxyalkoxy, haloalkoxy, haloalkoxyalkoxy, —O—$NR^{23f}R^{23g}$, —O—$(CR^{25b}R^{26b})_u$-$A^4$, —O—$(CR^{25b}R^{26b})_u$—C(=O)$NR^{101d}R^{102d}$, —O—$(CR^{25b}R^{26b})_u$—C(=S)$NR^{101d}R^{102d}$, —O—$(CR^{25b}R^{26b})_u$—$SO_2NR^{101d}R^{102d}$, —O—$(CR^{25b}R^{26b})_q$—$NR^{103}R^{104}$, —$NR^{23f}R^{23g}$, —$NR^{23f}$—$(CR^{25b}R^{26b})_u$-$A^4$, —$NR^{23f}$—$(CR^{25b}R^{26b})_u$—C(=O)$NR^{101d}R^{102d}$, —$NR^{23f}$—$(CR^{25b}R^{26b})_u$—C(=S)$NR^{101d}R^{102d}$, —$NR^{23f}$—$(CR^{25b}R^{26b})_u$—$SO_2NR^{101d}R^{102d}$, or —$NR^{23}$—$(CR^{25b}R^{26b})_q$—$NR^{103}R^{104}$ can be prepared from compounds of formula (19). The reaction may be conducted by reacting compounds (19) with an appropriate amine or alcohol reagent in the presence of a base such as, but not limited to, triethylamine, potassium tert-butoxide, sodium tert-butoxide or sodium hydride in a solvent such as, but not limited to, tetrahydrofuran or dimethylformamide at temperatures from 0° C. to 150° C. This reaction may be assisted by microwave irradiation.

It will be appreciated that the synthetic schemes and specific examples as illustrated in the Examples section are illustrative and are not to be read as limiting the scope as it is defined in the appended claims. All alternatives, modifications, and equivalents of the synthetic methods and specific examples are included within the scope of the claims.

Optimum reaction conditions and reaction times for each individual step may vary depending on the particular reactants employed and substituents present in the reactants used. Unless otherwise specified, solvents, temperatures and other reaction conditions may be readily selected by one of ordinary skill in the art. Specific procedures are provided in the Examples section. Reactions may be worked up in the conventional manner, e.g. by eliminating the solvent from the residue and further purified according to methodologies generally known in the art such as, but not limited to, crystallization, distillation, extraction, trituration and chromatography. Unless otherwise described, the starting materials and reagents are either commercially available or may be prepared by one skilled in the art from commercially available materials using methods described in the chemical literature.

The skilled artisan will also appreciate that not all of the substituents in the compounds of formula (I) will tolerate certain reaction conditions employed to synthesize the compounds. Routine experimentations, including appropriate manipulation of the reaction conditions, reagents and sequence of the synthetic route, protection of any chemical functionality that may not be compatible with the reaction conditions, and deprotection at a suitable point in the reaction sequence of the method, followed by further transformation of the molecules using standard chemical techniques well known to those skilled in the art such as alkylation, acylation, reductive amination, sulfonylation, oxidation, reduction and the like, are included within the scope. Suitable protecting groups and the methods for protecting and deprotecting different substituents using such suitable protecting groups are well known to those skilled in the art; examples of which may be found in T. Greene and P. Wuts, Protecting Groups in Chemical Synthesis (3rd ed.), John Wiley & Sons, NY (1999), which is incorporated herein by reference in its entirety.

Furthermore, the skilled artisan will appreciate that in many circumstances, the order in which moieties are introduced may not be critical. The particular order of steps required to produce the compounds of formula (I) is dependent upon the particular compounds being synthesized, the starting compound, and the relative lability of the substituted moieties. Thus, synthesis of the present compounds may be accomplished by methods analogous to those described in the synthetic schemes described hereinabove and in specific examples, and routine experimentations, including appropriate manipulation of the reaction conditions, reagents and sequence of the synthetic route are within the scope.

Starting materials, if not commercially available, may be prepared by procedures selected from standard organic chemical techniques, techniques that are analogous to the synthesis of known, structurally similar compounds, or techniques that are analogous to the above described schemes or the procedures described in the synthetic examples section.

When an optically active form of a compound is required, it may be obtained by carrying out one of the procedures described herein using an optically active starting material (prepared, for example, by asymmetric induction of a suitable reaction step), or by resolution of a mixture of the stereoisomers of the compound or intermediates using a standard procedure (such as chromatographic separation, recrystallization or enzymatic resolution).

Similarly, when a pure geometric isomer of a compound is required, it may be obtained by carrying out one of the above procedures using a pure geometric isomer as a starting material, or by resolution of a mixture of the geometric isomers of the compound or intermediates using a standard procedure such as chromatographic separation.

Following Examples may be used for illustrative purposes and should not be deemed to narrow the scope.

g. Examples

Example 1

N-[(2Z)-5-tert-butyl-3-{[1-(methylsulfonyl)azetidin-3-yl]methyl}-1,3-thiazol-2(3H)-ylidene]-2-methoxy-5-(trifluoromethyl)benzamide Example 1A tert-butyl 3-((5-tert-butyl-2-iminothiazol-3(2H)-yl)methyl)azetidine-1-carboxylate A mixture of 3,3-dimethylbutanal (3.71 mL, 29.5 mmol), tert-butyl 3-(aminomethyl)azetidine-1-carboxylate (Astatech, 5 g, 26.8 mmol), and 8 g of 4 Å molecular sieves (8-12 mesh beads) in acetonitrile (50 mL) was stirred at ambient temperature for 72 h. The material was filtered through Celite with acetonitrile (additional 25 mL) then potassium thiocyanate (3.47 g, 35.7 mmol) was added and the mixture was warmed to 50° C. Iodine (6.81 g, 26.8 mmol) was added and the mixture stirred at 50° C. for 16 h then was cooled to ambient temperature. The mixture was stirred with 75 mL of 20% aqueous sodium metabisulfite for 1 h then the layers were separated and the aqueous layer was extracted with 3×10 mL $CH_2Cl_2$. The combined organics were dried over anhydrous $Na_2SO_4$, filtered, and concentrated under reduced pressure to give the crude title compound (6.3 g, 19.4 mmol, 72% yield) which was carried on without further purification. MS (DCI/$NH_3$) m/z 326 (M+H)$^+$.

Example 1B 2-methoxy-5-(trifluoromethyl)benzoyl chloride

A solution of 2-methoxy-5-(trifluoromethyl)benzoic acid (0.68 g, 3.1 mmol) in thionyl chloride (10 mL) was warmed to reflux and was allowed to stir for 2 h. The mixture was cooled to ambient temperature, concentrated under reduced pressure and diluted with 10 mL of toluene. This material was again concentrated under reduced pressure and was again diluted with 10 mL of toluene. This concentration and dilution was repeated for an additional time and the crude acid chloride was carried on to the next step.

Example 1C (Z)-tert-butyl 3-((5-tert-butyl-2-(2-methoxy-5-(trifluoromethyl)benzoylimino)thiazol-3(2H)-yl)methyl)azetidine-1-carboxylate To a solution of the product of Example 1A (1 g, 3.1 mmol) in tetrahydrofuran (20 mL) was added triethylamine (1.3 mL, 9.2 mmol). Example 1B (3 mmol) in 5 mL tetrahydrofuran was added via cannula. This mixture was warmed to 50° C. and was allowed to stir for 4 h. The mixture was then stirred at ambient temperature for 72 h. The reaction mixture was quenched with 10 mL of saturated, aqueous $NH_4Cl$ and the layers were separated. The aqueous layer was extracted with 3×10 mL ethyl acetate and the combined organics were dried over anhydrous $Na_2SO_4$, filtered, and concentrated under reduced pressure. The crude material was purified by column chromatography ($SiO_2$, 60% hexanes in ethyl acetate) to give the title compound (0.55 g, 1.04 mmol, 34% yield). MS (DCI/$NH_3$) m/z 528 (M+H)$^+$.

Example 1D (Z)—N-(3-(azetidin-3-ylmethyl)-5-tert-butylthiazol-2(3H)-ylidene)-2-methoxy-5-(trifluoromethyl)benzamide To a solution of the product of Example IC (1.79 g, 3.4 mmol) in $CH_2Cl_2$ (25 mL) at 0° C. was added trifluoroacetic acid (12 mL, 156 mmol) dropwise over 15 min. The mixture was allowed to warm to ambient temperature and was allowed to stir for 3 hours. The mixture was concentrated under reduced pressure and purified by column chromatography ($SiO_2$, 100% $CH_2Cl_2$ then 9:1:0.1 $CH_2Cl_2$:methanol:$NH_4OH$) to give the title compound (1.76 g, 3.29 mmol, 97% yield). MS (DCI/$NH_3$) m/z 428 (M+H)$^+$.

Example 1E

N-[(2Z)-5-tert-butyl-3-{[1-(methylsulfonyl)azetidin-3-yl]methyl}-1,3-thiazol-2(3H)-ylidene]-2-methoxy-5-(trifluoromethyl)benzamide To a solution of the product of Example 1D (0.35 g, 0.66 mmol) and triethyl amine (0.27 mL, 2.0 mmol) in tetrahydrofuran (10 mL) at 0° C. was added methanesulfonyl chloride (0.061 mL, 0.79 mmol). The mixture was stirred at 0° C. for 10 min and then was allowed to warm to ambient temperature and was stirred for 1 h. The reaction mixture was quenched with 5 mL saturated, aqueous $NaHCO_3$, the layers were separated and the aqueous layer was extracted with 3×5 mL ethyl acetate. The combined organics were dried over anhydrous $Na_2SO_4$, filtered, and concentrated under reduced pressure. The crude material was purified by column chromatography ($SiO_2$, 60% hexanes in ethyl acetate) to give the title compound (0.22 g, 0.44 mmol, 66% yield). $^1$H NMR (300 MHz, $CDCl_3$) δ ppm 1.35 (s, 9 H), 2.83 (s, 3 H), 3.15-3.34 (m, 1 H), 3.84 (dd, J=8.1, 5.8 Hz, 2 H), 3.97 (s, 3 H), 4.04 (t, J=8.3 Hz, 2 H), 4.42 (d, J=7.5 Hz, 2H), 6.64 (s, 1H), 7.06 (d, J=8.7 Hz, 1 H), 7.65 (dd, J=8.7, 2.0 Hz, 1 H), 8.22 (d, J=2.4 Hz, 1 H); MS (DCI/$NH_3$) m/z 506 (M+H)$^+$; Anal. calculated for $C_{21}H_{26}F_3N_3O_4S_2$: C, 49.89; H, 5.18; N, 8.31. Found: C, 49.93; H, 5.16; N, 8.05.

Example 2

N-[(2Z)-5-tert-butyl-3-{[1-(cyclopropylsulfonyl)azetidin-3-yl]methyl}-1,3-thiazol-2(3H)-ylidene]-2-methoxy-5-(trifluoromethyl)benzamide To a solution of the product of Example 1D (0.35 g, 0.66 mmol) and triethyl amine (0.27 mL, 2.0 mmol) in tetrahydrofuran (10 mL) at 0° C. was added cyclopropanesulfonyl chloride (0.080 mL, 0.79 mmol). The mixture was stirred at 0° C. for 10 minutes and then was allowed to warm to ambient temperature and was stirred for 2 h. The mixture was quenched with 5 mL saturated, aqueous $NaHCO_3$, the layers were separated and the aqueous layer was extracted with 3×5 mL ethyl acetate. The combined organics were dried over $Na_2SO_4$, filtered, and concentrated under reduced pressure. The crude material was purified by column chromatography ($SiO_2$, 60% hexanes in ethyl acetate) to give the title compound (0.25 g, 0.47 mmol, 72% yield). $^1$H NMR (300 MHz, $CDCl_3$) δ ppm 0.90-1.00 (m, 2 H), 1.06-1.17 (m, 2 H), 1.35 (s, 9 H), 2.22-2.36 (m, 1 H), 3.17-3.33 (m, 1 H), 3.85 (dd, J=8.1, 5.8 Hz, 2 H), 3.97 (s, 3 H), 4.06 (t, J=8.1 Hz, 2 H), 4.42 (d, J=7.1 Hz, 2 H), 6.64 (s, 1 H), 7.05 (d, J=8.8 Hz, 1 H), 7.64 (dd, J=9.0, 2.9 Hz, 1H), 8.21 (d, J=2.4 Hz, 1 H)); MS (DCI/$NH_3$) m/z 532 (M+H)$^+$; Anal. calculated for $C_{23}H_{28}F_3N_3O_4S_2.0.1C_4H_8O_2$: C, 52.01; H, 5.37; N, 7.78. Found: C, 52.01; H, 4.98; N, 7.43.

Example 3

5-chloro-2-methoxy-N-[(2Z)-5-methyl-3-{[1-(methylsulfonyl)azetidin-3-yl]methyl}-1,3-thiazol-2(3H)-ylidene]benzamide Example 3A tert-butyl 3-(hydroxymethyl)azetidine-1-carboxylate To a solution of 1-Boc-azetidine-3-carboxylic acid (Astatech, 1.0 g, 4.97 mmol) in tetrahydrofuran (10 mL) at −10° C.

was added 4-methylmorpholine (0.55 mL, 5.0 mmol). This mixture was stirred for 1 minute and then ethyl chloroformate (0.47 mL, 4.97 mmol) was added dropwise. The mixture was stirred at −10° C. for 15 min then was filtered through Celite and the filtrate was added dropwise via syringe to a mixture of NaBH$_4$ (0.42 g, 11.2 mmol) in H$_2$O (5 mL) at 5° C. The mixture was allowed to warm to ambient temperature and was stirred vigorously for 3 h. The reaction mixture was quenched with 5 mL saturated, aqueous NH$_4$Cl, the layers were separated and the aqueous layer was extracted with 3×5 mL ethyl acetate. The combined organics were dried over anhydrous Na$_2$SO$_4$, filtered, concentrated under reduced pressure and purified by column chromatography (SiO$_2$, 30% hexanes in ethyl acetate) to give the title compound (0.62 g, 3.3 mmol, 66% yield). MS (DCI/NH$_3$) m/z 188 (M+H)$^+$.

Example 3B tert-butyl 3-(tosyloxymethyl)azetidine-1-carboxylate

To a solution of the product of Example 3A (0.62 g, 3.3 mmol) in CH$_2$Cl$_2$ (7 mL) and pyridine (7 mL) was added p-toluenesulfonyl chloride (0.63 g, 3.3 mmol) portionwise over 5 min. The mixture was stirred at ambient temperature for 24 h then was quenched with 10 mL 5% aqueous HCl. The layers were separated and the aqueous layer was extracted (3×5 mL CH$_2$Cl$_2$). The combined organics were dried over anhydrous Na$_2$SO$_4$, filtered, concentrated under reduced pressure and purified by column chromatography (SiO$_2$, 50% hexanes in ethyl acetate) to give the title compound (0.95 g, 2.8 mmol, 84% yield). MS (DCI/NH$_3$) m/z 359 (M+NH$_4$)$^+$.

Example 3C tert-butyl 3-((2-imino-5-methylthiazol-3(2H)-yl)methyl)azetidine-1-carboxylate A mixture of 2-amino-5-methylthiazole (0.32 g, 2.8 mmol), the product of Example 3B (0.95 g, 2.8 mmol) and tetrabutylammonium iodide (0.51 g, 1.4 mmol) in 1 mL N,N-dimethylformamide was warmed to 85° C. and was allowed to stir for 16 h. The mixture was allowed to cool to ambient temperature, was diluted with CH$_2$Cl$_2$ (10 mL) and washed with 5 mL saturated, aqueous NaHCO$_3$. The layers were separated and the aqueous layer was extracted with 3×5 mL CH$_2$Cl$_2$. The combined organics were dried over anhydrous Na$_2$SO$_4$, filtered, concentrated under reduced pressure and purified by column chromatography (SiO$_2$, 10% CH$_3$OH in ethyl acetate then 9:1:0.1 CH$_2$Cl$_2$:CH$_3$OH:NH$_4$OH) to give the title compound (0.55 g, 1.9 mmol, 69% yield). MS (DCI/NH$_3$) m/z 284 (M+NH$_4$)$^+$.

Example 3D 5-chloro-2-methoxybenzoyl chloride

A solution of 5-chloro-2-methoxybenzoic acid (0.37 g, 2.0 mmol) in 10 mL of SOCl$_2$ was warmed to reflux and was allowed to stir for 2 hours. The mixture was cooled to ambient temperature and concentrated under reduced pressure. The crude material was diluted with 5 mL of toluene and concentrated under reduced pressure. This dilution with toluene and concentration was repeated two additional times to afford the title compound. $^1$H NMR (300 MHz, dimethylsulfoxide-d$_6$) δ ppm 3.82 (s, 3 H), 7.16 (d, J=8.8 Hz, 1 H), 7.49-7.59 (m, 1 H), 7.61 (d, J=2.7 Hz, 1 H).

Example 3E (Z)-tert-butyl 3-((2-(5-chloro-2-methoxybenzoylimino)-5-methylthiazol-3(2H)-yl)methyl)azetidine-1-carboxylate To a solution of the product of Example 3C (0.55 g, 1.9 mmol) in tetrahydrofuran (15 mL) was added triethyl amine (0.81 mL, 5.8 mmol) followed by Example 3D (1.9 mmol) in 3 mL tetrahydrofuran. This mixture was warmed to 50° C. and was stirred for 4 h. The mixture was cooled to ambient temperature, was quenched with 10 mL NH$_4$Cl and the resulting layers were separated. The aqueous layer was extracted with 3×5 mL ethyl acetate and the combined organics were dried over anhydrous Na$_2$SO$_4$, filtered, concentrated under reduced pressure and purified by column chromatography (SiO$_2$, 40% hexanes in ethyl acetate) to give the title compound (0.56 g, 1.2 mmol, 64% yield). MS (DCI/NH$_3$) m/z 452 (M+NH$_4$)$^+$.

Example 3F (Z)—N-(3-(azetidin-3-ylmethyl)-5-methylthiazol-2(3H)-ylidene)-5-chloro-2-methoxybenzamide To a solution of the product of Example 3E (0.52 g, 1.15 mmol) in CH$_2$Cl$_2$ (10 mL) at 0° C. was added trifluoroacetic acid (5 mL) dropwise via syringe. The mixture was allowed to warm to ambient temperature and was stirred for 2 h. The mixture was concentrated under reduced pressure and purified by column chromatography (SiO$_2$, 9:1:0.1 CH$_2$Cl$_2$:CH$_3$OH:NH$_4$OH) to give the title compound (0.36 g, 1.0 mmol, 89% yield). MS (DCI/NH$_3$) m/z 352 (M+NH$_4$)$^+$.

Example 3G 5-chloro-2-methoxy-N-[(2Z)-5-methyl-3-{[1-(methylsulfonyl)azetidin-3-yl]methyl}-1,3-thiazol-2(3H)-ylidene]benzamide To a solution of the product of Example 3F (0.15 g, 0.43 mmol) in tetrahydrofuran (10 mL) at ambient temperature was added triethyl amine (0.18 mL, 1.3 mmol) followed by methanesulfonyl chloride (40 µL, 0.51 mmol). This mixture was stirred at ambient temperature for 24 h then was quenched with 5 mL saturated, aqueous NaHCO$_3$. The layers were separated and the aqueous layer was extracted 3×5 mL ethyl acetate. The combined organics were dried over anhydrous Na$_2$SO$_4$, filtered, concentrated under reduced pressure and purified by column chromatography (SiO$_2$, 20% hexanes in ethyl acetate) to give the title compound (0.13 g, 0.30 mmol, 70% yield). $^1$H NMR (300 MHz, CD$_3$OD) δ ppm 2.34 (d, J=1.4 Hz, 3 H), 2.89 (s, 3 H), 3.11-3.26 (m, 1 H), 3.87 (dd, J=8.3, 5.9 Hz, 2 H), 3.86 (s, 3 H), 4.00 (t, J=8.3 Hz, 2 H), 4.50 (d, J=7.1 Hz, 2 H), 7.08 (d, J=8.8 Hz, 1 H), 7.15-7.20 (m, 1 H), 7.40 (dd, J=8.8, 2.7 Hz, 1 H), 7.80 (d, J=2.7 Hz, 1 H); MS (DCI/NH$_3$) m/z 430 (M+H)$^+$; Anal. calculated for C$_{17}$H$_{20}$ClN$_3$O$_4$S$_2$: C, 47.49; H, 4.69; N, 9.77. Found: C, 47.64; H, 4.65; N, 9.46.

Example 4

N-[(2Z)-5-tert-butyl-3-{[(2R)-5-oxopyrrolidin-2-yl]methyl}-1,3-thiazol-2(3H)-ylidene]-5-chloro-2-methoxybenzamide

Example 4A (R)-(5-oxopyrrolidin-2-yl)methyl 4-methylbenzenesulfonate

To a mixture of (R)-ethyl 5-oxopyrrolidin-2-carboxylate (Aldrich, 3 g, 19 mmol) and sodium borohydride (1.89 g, 50 mmol) in tetrahydrofuran (30 mL) at 50° C. was added dropwise for 30 min methanol (10 mL). The reaction was then continued for an additional 15 min and cooled to room temperature. The mixture was treated with 1N HCl to pH=3 and concentrated under reduced pressure. The residue was triturated with anhydrous methanol and the solid was filtered off and washed with methanol. The filtrate and washings were combined and concentrated under reduced pressure. The concentrate was then triturated with anhydrous tetrahydrofuran and filtered. The filtrate was concentrated under reduced pressure and the concentrate was dissolved in anhydrous $CH_2Cl_2$ (20 mL). p-Toluenesulfonyl chloride (3.64 g, 19 mmol) was added, the mixture was cooled to 0° C. and triethylamine (2.66 mL, 19 mmol) was added dropwise. The reaction mixture was allowed to warm to room temperature and stirred for 12 h. The mixture was then washed with water, brine, dried with anhydrous $MgSO_4$ and concentrated under reduced pressure. The residue was chromatographed ($SiO_2$, ethyl acetate-ethanol 9:1) to afford 3.5 g of the title compound. $^1H$ NMR (300 MHz, DMSO-$d_6$) δ 1.62 (m 1H), 2.06 (m, 3H), 2.42 (s, 3H), 3.71 (m, 1H), 3.87 (dd, J=10 Hz, 4 Hz, 1H), 3.97 (dd, J=10 Hz, 4 Hz, 1H), 7.49 (d, J=9 Hz, 2H), 7.75 (broad s, 1H), 7.82 (d, J=9 Hz, 2H); MS (DCI/$NH_3$) m/z 270 $(M+H)^+$, 287 $(M+NH_4)^+$.

Example 4B 5-tert-butylthiazol-2-amine

To a solution of 3,3-dimethylbutyraldehyde (10 g, 99.8 mmol) in 200 mL of cyclohexane was added pyrrolidine (8.7 mL, 0.11 mol) followed by p-toluenesulfonic acid monohydrate (0.95 g, 5.0 mmol). This reaction flask was equipped with a Dean-Stark trap and the mixture was warmed to reflux and was allowed to stir for 3 hours. The mixture was cooled to ambient temperature, filtered, and concentrated under reduced pressure. The residue was dissolved in 75 mL of $CH_3OH$, sulfur was added (3.2 g, 99.8 mmol), and the mixture was cooled to 0° C. Cyanamide (4.2 g, 99.8 mmol) was added portion-wise over 10 minutes and the mixture was allowed to warm to ambient temperature and stir for 18 hours. The reaction mixture was concentrated under reduced pressure and purified by column chromatography ($SiO_2$, ethyl acetate then 10% methanol in ethyl acetate) to afford the title compound. MS (DCI/$NH_3$) m/z 157 $(M+H)^+$.

Example 4C

N-(5-tert-butylthiazol-2-yl)-5-chloro-2-methoxybenzamide

To a solution of Example 4B (0.94 g, 6.0 mmol) in tetrahydrofuran (40 mL) was added Example 3D (1.23 g, 6.0 mmol), triethylamine (2.4 mL, 18 mmol), and 4-dimethylaminopyridine (7.5 mg, 0.06 mmol). The reaction mixture was stirred at 60° C. for 14 hours and then cooled to ambient temperature, diluted with saturated aqueous $NaHCO_3$ (20 mL) and extracted with ethyl acetate (3×30 mL). The combined organic extracts were dried over anhydrous $Na_2SO_4$, filtered, and concentrated under reduced pressure. The residue was purified by column chromatography using an Analogix® Intelliflash280 ™ ($SiO_2$, 0-100% ethyl acetate in hexanes) to afford the title compound. MS (ESI$^+$) m/z 325 $(M+H)^+$.

Example 4D

N-[(2Z)-5-tert-butyl-3-{[(2R)-5-oxopyrrolidin-2-yl]methyl}-1,3-thiazol-2(3H)-ylidene]-5-chloro-2-methoxybenzamide A mixture of Example 4C (650 mg, 2 mmol), Example 4A (700 mg, 2.6 mmol), potassium carbonate (653 mg, 4 mmol), tetrabutylammonium iodide (20 mg, 0.05 mmol), tetrabutylammonium hydrogensulfate (20 mg, 0.06 mmol) and tetraethylammonium iodide (20 mg, 0.07 mmol) in anhydrous toluene (60 mL) was refluxed for 15 h. The mixture was then washed with water, brine, dried with anhydrous $MgSO_4$, filtered, and concentrated under reduced pressure. The residue was chromatographed ($SiO_2$, ethyl acetate-ethanol 9:1) to afford 490 mg of the title compound. $^1H$ NMR (300 MHz, DMSO-$d_6$) δ 1.31 (s, 9H), 1.83 (m, 1H), 2.07 (m, 3H), 3.78 (s, 3H), 4.09 (m, 2H), 4.30 (m, 1H), 7.10 (d, J=9 Hz, 1H), 7.27 (s, 1H), 7.45 (dd, J=9 Hz, 3 Hz, 1H), 7.62 (d, J=3 Hz, 1H), 7.85 (broad s, 1H); MS (DCI/$NH_3$) m/z 422 $(M+H)^+$.

Example 5

N-[(2Z)-5-tert-butyl-3-{[(2S)-5-oxopyrrolidin-2-yl]methyl}-1,3-thiazol-2(3H)-ylidene]-5-chloro-2-methoxybenzamide A mixture of Example 4C (810 mg, 2.49 mmol), (S)-(5-oxopyrrolidin-2-yl)methyl 4-methylbenzenesulfonate (Aldrich, 807 mg, 3 mmol), potassium carbonate (828 mg, 6 mmol), tetrabutylammonium iodide (20 mg, 0.05 mmol), tetrabutylammonium hydrogensulfate (20 mg, 0.06 mmol) and tetraethylammonium iodide (20 mg, 0.07 mmol) in anhydrous toluene (100 mL) was refluxed for 15 h. The mixture was cooled to room temperature, washed with water, brine, dried with anhydrous $MgSO_4$, filtered, and concentrated under reduced pressure. The residue was chromatographed ($SiO_2$, ethyl acetate-ethanol 9:1) to afford 510 mg of the title compound. $^1H$ NMR (300 MHz, DMSO-$d_6$) δ 1.32 (s, 9H), 1.83 (m, 1H), 2.07 (m, 3H), 3.78 (s, 3H), 4.09 (m, 2H), 4.30 (m, 1H), 7.10 (d, J=9 Hz, 1H), 7.27 (s, 1H), 7.45 (dd, J=9 Hz, 3 Hz, 1H), 7.62 (d, J=3 Hz, 1H), 7.82 (broad s, 1H); MS (DCI/$NH_3$) m/z 422 $(M+H)^+$. Anal. calcd for $C_{20}H_{24}ClN_3O_3S.0.25H_2O$: C, 56.33; H, 5.79; N, 9.85. Found: C, 56.42; H, 5.55; N, 9.25.

Example 6

N-[(2Z)-5-tert-butyl-3-{[(2S)-5-oxopyrrolidin-2-yl]methyl}-1,3,4-thiadiazol-2(3H)-ylidene]-5-chloro-2-methoxybenzamide

Example 6A

N-(5-tert-butyl-1,3,4-thiadiazol-2-yl)-5-chloro-2-methoxybenzamide

To a solution of 5-tert-butyl-1,3,4-thiadiazole-2-amine (Aldrich, 1.57 g, 10 mmol) and Example 3D (2.05 g, 10 mmol) in anhydrous CH$_2$Cl$_2$ (45 mL) at 0° C. was added dropwise triethylamine (1.67 mL, 12 mmol) and the reaction mixture was allowed to warm to room temperature and stirred for 12 h. The mixture was then washed with water, brine, dried with anhydrous MgSO$_4$, filtered, and concentrated under reduced pressure to afford 3.2 g of the title compound. $^1$H NMR (300 MHz, DMSO-d$_6$) δ 1.42 (s, 9H), 3.87 (s, 3H), 7.22 (d, J=9 Hz, 1H), 7.60 (m, 2H), 12.40 (broad s, 1H); MS (DCI/NH$_3$) m/z 326 (M+H)$^+$.

Example 6B

N-[(2Z)-5-tert-butyl-3-{[(2S)-5-oxopyrrolidin-2-yl]methyl}-1,3-thiazol-2(3H)-ylidene]-5-chloro-2-methoxybenzamide A mixture of Example 6A (325 mg, 1 mmol), (S)-(5-oxopyrrolidin-2-yl)methyl 4-methylbenzenesulfonate (Aldrich, 400 mg, 1.5 mmol), potassium carbonate (276 mg, 2 mmol), tetrabutylammonium iodide (15 mg, 0.04 mmol), tetrabutylammonium hydrogensulfate (15 mg, 0.04 mmol) and tetraethylammonium iodide (15 mg, 0.06 mmol) in anhydrous toluene (50 mL) was refluxed for 15 h. The mixture was then cooled to room temperature, washed with water, brine, dried with anhydrous MgSO$_4$, filtered, and concentrated under reduced pressure. The residue was purified by chromatography (SiO$_2$, ethyl acetate-ethanol 9:1) to afford 260 mg of the title compound. $^1$H NMR (300 MHz, DMSO-d$_6$) δ 1.38 (s, 9H), 1.90 (m, 1H), 2.12 (m, 3H), 3.80 (s, 3H), 4.10 (m, 1H), 4.27 (dd, J=13 Hz, 6 Hz, 1H), 4.44 (dd, J=13 Hz, 6 Hz, 1H), 7.14 (d, J=9 Hz, 1H), 7.50 (dd, J=9 Hz, 3 Hz, 1H), 7.71 (d, J=3 Hz, 1H), 7.80 (broad s, 1H); MS (DCI/NH$_3$) m/z 423 (M+H)$^+$. Anal. calcd for C$_{19}$H$_{23}$ClN$_4$O$_3$S.0.25H$_2$O: C, 53.39; H, 5.54; N, 13.11. Found: C, 53.59; H, 5.41; N, 12.79.

Example 7

N-[(2Z)-5-tert-butyl-3-{[(2R)-5-oxopyrrolidin-2-yl]methyl}-1,3,4-thiadiazol-2(3H)-ylidene]-5-chloro-2-methoxybenzamide A mixture of Example 6A (650 mg, 2 mmol), Example 4A (807 mg, 3 mmol), potassium carbonate (522 mg, 3.8 mmol), tetrabutylammonium iodide (20 mg, 0.05 mmol), tetrabutylammonium hydrogensulfate (20 mg, 0.06 mmol) and tetraethylammonium iodide (15 mg, 0.06 mmol) in anhydrous toluene (80 mL) was refluxed for 15 h. The mixture was then cooled to room temperature, washed with water, brine, dried with anhydrous MgSO$_4$, filtered, and concentrated under reduced pressure. The residue was purified by chromatography (SiO$_2$, ethyl acetate-ethanol 9:1) to afford 540 mg of the title compound. $^1$H NMR (300 MHz, DMSO-d$_6$) δ 1.38 (s, 9H), 1.90 (m, 1H), 2.12 (m, 3H), 3.80 (s, 3H), 4.10 (m, 1H), 4.27 (dd, J=13 Hz, 6 Hz, 1H), 4.44 (dd, J=13 Hz, 6 Hz, 1H), 7.14 (d, J=9 Hz, 1H), 7.50 (dd, J=9 Hz, 3 Hz, 1H), 7.71 (d, J=3 Hz, 1H), 7.85 (broad s, 1H); MS (DCI/NH$_3$) m/z 423 (M+H)$^+$. Anal. calcd for C$_{19}$H$_{23}$ClN$_4$O$_3$S: C, 53.96; H, 5.48; N, 13.25. Found: C, 54.35; H, 5.60; N, 12.88.

Example 8

N-[(2Z)-5-tert-butyl-3-{[(2S)-1-methyl-5-oxopyrrolidin-2-yl]methyl}-1,3,4-thiadiazol-2(3H)-ylidene]-5-chloro-2-methoxybenzamide

Example 8A (5S)-5-(hydroxymethyl)-1-methylpyrrolidin-2-one

To a solution of (S)-methyl 5-oxo-pyrrolidine-2-carboxylate (Aldrich, 2.86 g, 20 mmol) in tetrahydrofuran (50 mL) at 0° C. was added in portions 60% oil dispersion NaH (720 mg, 30 mmol). Methyl iodide (1.88 mL, 30 mmol) was added and the mixture was allowed to warm to ambient temperature and stirred for 16 h. The mixture was concentrated under reduced pressure and residue was partitioned between water and ethyl acetate. The organic layer was washed with water, brine, dried with anhydrous MgSO$_4$, filtered, and concentrated under reduced pressure. The residue was redissolved in anhydrous tetrahydrofuran (50 mL), sodium borohydride (946 mg, 25 mmol) was added followed by dropwise addition (~20 min) of methanol (20 mL) at 50° C. The reaction mixture was stirred for an additional 1 h at a range from 45° C. to 50° C., then cooled to room temperature and concentrated under reduced pressure. Citric acid (10%) was added and the mixture was extracted with ethyl acetate. The organic layer was washed with water, brine, dried with anhydrous MgSO$_4$, filtered, and concentrated under reduced pressure. The residue was purified by chromatography (SiO$_2$, ethyl acetate-ethanol 4:1) to afford 1.3 g of the title compound. $^1$H NMR (300 MHz, DMSO-d$_6$) δ 1.77 (m 1H), 1.95 (m, 1H), 2.18 (m, 2H), 2.69 (s, 3H), 3.43 (m, 2H), 3.55 (m, 1H), 4.77 (t, J=6 Hz, 1H); MS (DCI/NH$_3$) m/z 130 (M+H)$^+$, 147 (M+NH$_4$)$^+$.

Example 8B

[(2S)-1-methyl-5-oxopyrrolidin-2-yl]methyl 4-methylbenzenesulfonate

Example 8A (1.29 g, 10 mmol) was dissolved in anhydrous CH$_2$Cl$_2$ (60 mL), p-toluenesulfonyl chloride (2.1 g (11 mmol)) was added followed by dropwise addition of triethylamine at 0° C. The reaction mixture was allowed to warm to ambient temperature and stirred for 16 h, washed with water, brine, dried with anhydrous MgSO$_4$, filtered, and concentrated under reduced pressure. The residue was purified by chromatography (SiO$_2$, ethyl acetate-ethanol 9:1) to afford 1.5 g of the title compound. $^1$H NMR (300 MHz, DMSO-d$_6$) δ 1.62 (m 1H), 2.06 (m, 3H), 2.42 (s, 3H), 2.57 (s, 3H), 3.72 (sextet, J=4 Hz, 1H), 4.06 (dd, J=10 Hz, 4 Hz, 1H), 4.22 (dd, J=10 Hz, 4 Hz, 1H), 7.50 (d, J=9 Hz, 2H), 7.80 (d, J=9 Hz, 2H); MS (DCI/NH$_3$) m/z 284 (M+H)$^+$, 301 (M+NH$_4$)$^+$.

Example 8C

N-[(2Z)-5-tert-butyl-3-{[(2S)-1-methyl-5-oxopyrrolidin-2-yl]methyl}-1,3,4-thiadiazol-2(3H)-ylidene]-5-chloro-2-methoxybenzamide A mixture of Example 6A (325 mg, 1 mmol), Example 8B (300 mg, 1.1 mmol), potassium carbonate (300 mg, 2.2 mmol), tetrabutylammonium iodide (15 mg (0.04 mmol), tetrabutylammonium hydrogensulfate (15 mg, 0.04 mmol) and tetraethylammonium iodide (15 mg, 0.05 mmol) in anhydrous toluene (50 mL) was refluxed for 15 h. The mixture was then cooled to room temperature, washed with water, brine, dried with anhydrous MgSO$_4$, filtered, and concentrated under reduced pressure. The residue was purified by chromatography (SiO$_2$, ethyl acetate) to afford 317 mg of the desired product. $^1$H NMR (300 MHz, DMSO-d$_6$) δ 1.36 (s, 9H), 1.75 (m, 1H), 2.00 (m, 3H), 2.77 (s, 3H), 3.80 (s, 3H), 4.05 (m, 1H), 4.46 (dd, J=13 Hz, 6 Hz, 1H), 4.65 (dd, J=13 Hz, 6 Hz, 1H), 7.15 (d, J=9 Hz, 1H), 7.50 (dd, J=9 Hz, 3 Hz, 1H), 7.77 (d, J=3 Hz, 1H); MS (DCI/NH$_3$) m/z 437 (M+H)$^+$. Anal. calcd for C$_{20}$H$_{25}$ClN$_4$O$_3$S: C, 54.97; H, 5.77; N, 12.82. Found: C, 54.90; H, 5.80; N, 12.63.

Example 9

N-[(2Z)-5-tert-butyl-3-{[1-(methylsulfonyl)azetidin-3-yl]methyl}-1,3-thiazol-2(3H)-ylidene]-5-chloro-2-methoxybenzamide

Example 9A tert-butyl 3-((5-tert-butyl-2-iminothiazol-3(2H)-yl)methyl)azetidine-1-carboxylate 3,3-Dimethylbutanal (0.7 mL, 5.4 mmol), tert-butyl 3-(aminomethyl)azetidine-1-carboxylate (Astatech, 1.0 g, 5.4 mmol) were mixed with 2 g of 4 Å molecular sieves in 5 mL of dry acetonitrile at room temperature for 20 hours. The reaction was filtered through Celite, washed with 5 mL of acetonitrile and the filtrate used without further purification. Potassium thiocyanate (0.7 g, 7.1 mmol) was added and the mixture heated to 50° C. for 10 minutes. Iodine (1.4 g, 5.4 mmol) was added and the reaction mixture was continued to stir at 50° C. for 6 hours. The reaction mixture was cooled to room temperature, 10 mL of acetonitrile was added, followed by 10 mL of 20% $Na_2S_2O_5$. The phases were separated and the organic phase was dried with $Na_2SO_4$, filtered, and the solvent removed to provide the title compound. LC/MS m/z 326.3 $(M+H)^+$. The product was used without further purification.

Example 9B

(Z)-tert-butyl 3-((5-tert-butyl-2-(5-chloro-2-methoxybenzoylimino)thiazol-3(2H)-yl)methyl)azetidine-1-carboxylate 5-Chloro-2-methoxybenzoic acid (1.0 g, 5.4 mmol) was dissolved in 3 mL of $CH_2Cl_2$ and 8 mL of oxalyl chloride (2M in $CH_2Cl_2$) was added followed by 20 μL of N,N-dimethylformamide. The reaction mixture was stirred at room temperature for 1 hour. The solvent was removed and the residue treated with toluene and solvent removed under vacuum. The residue was suspended in 6 mL of tetrahydrofuran, Example 9A (1.7 g, 5.4 mmol) was added, followed by triethylamine (2.2 mL, 16.1 mmol). The reaction mixture was stirred at room temperature for 2 hours then diluted with ethyl acetate (100 mL). The organic phase was washed with water, brine, dried with $MgSO_4$, filtered, and concentrated. The concentrate was purified by flash chromatography on $SiO_2$ eluting with a gradient from 0 to 50% ethyl acetate in hexanes over 1000 mL then isocratic for 1000 mL to provide the title compound (1.1 g, 2.2 mmol, 41%). MS $(DCI/NH_3)$ m/z 494.2 $(M+H)^+$. $^1$H NMR (300 MHz, $CDCl_3$) δ ppm 1.34 (s, 9 H) 1.44 (s, 9 H) 3.10-3.26 (m, 1 H) 3.77 (dd, J=8.82, 5.43 Hz, 2 H) 3.90 (s, 3 H) 4.05 (t, J=8.48 Hz, 2 H) 4.36 (s, 2 H) 6.62 (s, 1 H) 6.90 (d, J=8.82 Hz, 1 H) 7.33 (dd, J=8.82, 2.71 Hz, 1 H) 7.89 (d, J=3.05 Hz, 1 H).

Example 9C

(Z)—N-(3-(azetidin-3-ylmethyl)-5-tert-butylthiazol-2(3H)-ylidene)-5-chloro-2-methoxybenzamide Example 9B (1.1 g, 2.2 mmol) was dissolved in 8 mL of $CH_2Cl_2$, 2 mL of trifluoroacetic acid was added, and the reaction mixture was stirred at room temperature for 4 hours. The solvent was removed and the concentrate purified by flash chromatography on $SiO_2$ using a gradient from 0% methanol/$CH_2Cl_2$ to 10% methanol/$CH_2Cl_2$ (0.1% $NH_4OH$) over 300 mL then isocratic for 240 mL to provide the title compound (0.7 g, 1.9 mmol, 82% yield). MS $(DCI/NH_3)$ m/z 394.1 $(M+H)^+$. $^1$H NMR (300 MHz, $CDCl_3$) δ ppm 1.33 (s, 9 H) 3.52-3.66 (m, 1 H) 3.87 (s, 3 H) 3.92-4.02 (m, 2 H) 4.14 (t, J=9.32 Hz, 2 H) 4.47 (d, J=7.12 Hz, 2 H) 6.78 (s, 1 H) 6.89 (d, J=8.82 Hz, 1 H) 7.32 (dd, J=8.82, 2.71 Hz, 1 H) 7.82 (d, J=2.71 Hz, 1 H) 9.84 (s, 1 H).

Example 9D

N-[(2Z)-5-tert-butyl-3-{[1-(methylsulfonyl)azetidin-3-yl]methyl}-1,3-thiazol-2(3H)-ylidene]-5-chloro-2-methoxybenzamide Example 9C (0.6 g, 1.5 mmol) was dissolved in 15 mL of tetrahydrofuran, triethylamine (0.64 mL, 4.6 mmol) was added followed by methanesulfonyl chloride (0.14 mL, 1.8 mmol). The reaction mixture was stirred at room temperature for 1 hour, and diluted with ethyl acetate (100 mL). The organic phase was washed with water, brine, dried with $MgSO_4$, filtered, and concentrated. The concentrate was purified by flash chromatography on $SiO_2$, eluting with a gradient from $CH_2Cl_2$ to 10% B/$CH_2Cl_2$ (B=10% methanol/$CH_2Cl_2$ 0.1% $NH_4OH$) over 450 mL then isocratic for 300 mL to provide the title compound (0.36 g, 0.76 mmol, 50% yield). MS $(DCI/NH_3)$ m/z 472.1 $(M+H)^+$. $^1$H NMR (300 MHz, $CDCl_3$) δ ppm 1.35 (s, 9 H) 2.85 (s, 3 H) 3.17-3.31 (m, 1 H) 3.84 (dd, J=8.31, 5.59 Hz, 2 H) 3.90 (s, 3 H) 4.04 (t, J=8.31 Hz, 2 H) 4.42 (d, J=7.46 Hz, 2 H) 6.63 (s, 1 H) 6.92 (d, J=8.82 Hz, 1 H) 7.34 (dd, J=8.82, 2.71 Hz, 1 H) 7.91 (d, J=2.71 Hz, 1 H).

Example 10

N-[(2Z)-5-tert-butyl-3-{2-[methyl(methylsulfonyl)amino]ethyl}-1,3-thiazol-2(3H)-ylidene]-5-chloro-2-methoxybenzamide

Example 10A tert-butyl 2-(5-tert-butyl-2-iminothiazol-3(2H)-yl)ethylcarbamate tert-Butyl 2-aminoethylcarbamate (5.9 g, 37 mmol) and 3,3-dimethylbutanal (4.9 mL 95%, 37 mmol) were mixed in dry acetonitrile (30 mL) with 4 g of 4 Å (8-12 mesh beads) molecular sieves and stirred at room temperature for 24 hours. The reaction mixture was filtered through Celite and washed with acetonitrile (5 mL). Potassium thiocyanate (4.8 g, 49 mmol) was added and the mixture warmed to 50° C. for 10 minutes. Iodine (9.3 g, 37 mmol) was added and the reaction mixture was stirred at 50° C. for 6 hours. Acetonitrile (30 mL) was added followed by 10 mL of 20% $Na_2S_2O_5$. The layers were separated and the organic layer was dried with $Na_2SO_4$, filtered, and concentrated. The concentrate was purified by flash chromatography on $SiO_2$, equilibrating the column with $CH_2Cl_2$, loading the sample, and eluting with 5% methanol in $CH_2Cl_2$ (0.1% $NH_4OH$) isocratically to provide the title compound (3.5 g, 11.7 mmol, 32% yield). MS $(DCI/NH_3)$ m/z 300.2 $(M+H)^+$. $^1$H NMR (300 MHz, $CDCl_3$) δ ppm 1.31 (s, 9 H) 1.42 (s, 9 H) 3.57 (q, J=6.78 Hz, 2 H) 4.26 (t, J=6.95 Hz, 2 H) 5.63 (t, J=5.76 Hz, 1 H) 6.58 (s, 1 H).

Example 10B

(Z)-tert-butyl 2-(5-tert-butyl-2-(5-chloro-2-methoxybenzoylimino)thiazol-3(2H)-yl)ethylcarbamate 5-Chloro-2-methoxybenzoic acid (0.8 g, 4.3 mmol) was dissolved in 8 mL of $CH_2Cl_2$, oxalyl chloride (2M in $CH_2Cl_2$, 6.5 mL, 13 mmol) and N,N-dimethylformamide (20 µL) were added. The reaction mixture was stirred at room temperature for 1 hour. The solvent was removed and the residue dried twice from toluene. The residue was suspended in 5 mL of tetrahydrofuran, treated with Example 10A (1.3 g, 4.3 mmol) then triethylamine (1.8 mL, 12.9 mmol) and the reaction mixture was stirred at room temperature for 1 hour, diluted with ethyl acetate (100 mL), and separated. The organic phase was washed with water, brine, dried with $MgSO_4$, filtered, and concentrated. The residue was purified by flash chromatography on $SiO_2$, eluting with a gradient from 0 to 75% ethyl acetate in hexane over 750 mL then isocratic for 600 mL to provide the title compound (1.7 g, 3.6 mmol, 85% yield). MS (DCI/$NH_3$) m/z 468.2 $(M+H)^+$. $^1H$ NMR (300 MHz, $CDCl_3$) δ ppm 1.35 (s, 9 H) 1.39 (s, 9 H) 3.57 (q, J=5.82 Hz, 2 H) 3.90 (s, 3 H) 4.33 (t, J=5.75 Hz, 2 H) 5.41 (s, 1 H) 6.64 (s, 1 H) 6.91 (d, J=9.12 Hz, 1 H) 7.34 (dd, J=8.72, 2.78 Hz, 1 H) 7.93 (d, J=2.78 Hz, 1 H).

Example 10C (Z)-tert-butyl 2-(5-tert-butyl-2-(5-chloro-2-methoxy-benzoylimino)thiazol-3(2H)-yl)ethyl(methyl)carbamate Example 10B (0.5 g, 1.1 mmol) was dissolved in 4 mL of N,N-dimethylformamide and cooled to 0° C., treated with iodomethane (0.33 mL, 2.2 mmol) followed by NaH (60%, 0.056 g, 1.4 mmol). The reaction mixture was allowed to warm to ambient temperature and stirred for 1 hour. Ethyl acetate (100 mL) was added and the organic phase was washed with 20% $NH_4Cl$, water, brine, dried with $MgSO_4$, filtered, and concentrated to provide the title compound (0.45 g, 0.9 mmol, 87% yield). LCMS m/z 482.2 $(M+H)^+$.

Example 10D (Z)—N-(5-tert-butyl-3-(2-(methylamino)ethyl)thiazol-2(3H)-ylidene)-5-chloro-2-methoxybenzamide Example 10C (0.45 g, 0.9 mmol) was dissolved in 10 mL of $CH_2Cl_2$, treated with 2 mL of trifluoroacetic acid, and was stirred at room temperature for 90 minutes. The solvent was removed and the residue was treated with $CH_2Cl_2$ and concentrated. The residue was dissolved in 5% methanol/$CH_2Cl_2$ (0.1% $NH_4OH$), filtered through silica and washed with 5% methanol/$CH_2Cl_2$ (0.1% $NH_4OH$). The filtrate was concentrated to provide the title compound. LCMS m/z 382.2 $(M+H)^+$.

Example 10E

N-[(2Z)-5-tert-butyl-3-{2-[methyl(methylsulfonyl)amino]ethyl}-1,3-thiazol-2(3H)-ylidene]-5-chloro-2-methoxybenzamide Example 10D (0.36 g, 0.9 mmol) was dissolved in 13 mL of tetrahydrofuran, treated with methanesulfonyl chloride (0.073 mL, 0.9 mmol) and triethylamine (0.39 mL, 0.29 mmol), and stirred at room temperature for 1 hour. The mixture was diluted with ethyl acetate washed with water, brine, dried with $MgSO_4$, filtered, and concentrated. The residue was purified by flash chromatography ($SiO_2$, 0 to 75% ethyl acetate in hexane over 750 mL then isocratic for 300 mL) to provide the title compound (0.3 g, 0.65 mMol, 69% yield). MS (DCI/$NH_3$) m/z 460.1 $(M+H)^+$. $^1H$ NMR (300 MHz, $CDCl_3$) δ ppm 1.35 (s, 9 H) 2.79 (s, 3 H) 2.83 (s, 3 H) 3.61 (t, J=6.44 Hz, 2 H) 3.91 (s, 3 H) 4.38 (t, J=6.27 Hz, 2 H) 6.74 (s, 1 H) 6.92 (d, J=8.82 Hz, 1 H) 7.34 (dd, J=8.99, 2.88 Hz, 1 H) 8.00 (d, J=2.71 Hz, 1 H).

Example 11

N-[(2Z)-5-tert-butyl-3-[2-(dimethylamino)ethyl]-1,3-thiazol-2(3H)-ylidene]-5-chloro-2-methoxybenzamide Example 10B (0.35 g, 0.75 mmol) was mixed with 5 mL of 37% aq formaldehyde and mL of 88% formic acid. The mixture was refluxed at 100° C. for 3 hours. Reaction mixture was cooled, concentrated, diluted with ethyl acetate (100 mL), washed with 2N NaOH, water, brine, dried with $MgSO_4$, filtered, and concentrated. The concentrate was purified by flash chromatography ($SiO_2$, eluting with a gradient from 0 to 15% methanol in $CH_2Cl_2$ (0.1% $NH_4OH$) over 240 mL then isocratic for 300 mL) to provide the title compound (0.15 g, 0.38 mmol, 50% yield). MS (DCI/$NH_3$) m/z 396.2 $(M+H)^+$. $^1H$ NMR (300 MHz, $CDCl_3$) δ ppm 1.35 (s, 9 H) 2.63 (s, 6 H) 3.16-3.24 (m, 2 H) 3.91 (s, 3 H) 4.50-4.59 (m, 2 H) 6.88 (s, 1 H) 6.92 (d, J=8.73 Hz, 1 H) 7.35 (dd, J=8.73, 2.78 Hz, 1 H) 7.98 (d, J=2.78 Hz, 1 H).

Example 12

N-[(2Z)-5-tert-butyl-3-{2-[(methylsulfonyl)amino]ethyl}-1,3-thiazol-2(3H)-ylidene]-5-chloro-2-methoxybenzamide

Example 12A (Z)—N-(3-(2-aminoethyl)-5-tert-butylthiazol-2(3H)-ylidene)-5-chloro-2-methoxybenzamide A solution of Example 10B (0.38 g, 0.8 mmol) in $CH_2Cl_2$ (5 mL) was treated with 1 mL of trifluoroacetic acid and stirred at room temperature for 3 hours. The solvent was removed and the concentrate was purified by flash chromatography ($SiO_2$, eluting with a gradient from 0 to 15% methanol in $CH_2Cl_2$ (0.1% $NH_4OH$) in 240 mL then isocratic for 300 mL) to provide the title compound (0.29 g, 0.79 mmol, 97% yield). ESI m/z 368.0 $(M+H)^+$. $^1H$ NMR (300 MHz, DMSO-$d_6$) δ ppm 1.33 (s, 9 H) 3.23-3.38 (m, J=5.09 Hz, 2 H) 3.79 (s, 3 H) 4.27-4.47 (m, J=5.76, 5.76 Hz, 2 H) 7.13 (d, J=8.81 Hz, 1 H) 7.26 (s, 1 H) 7.47 (dd, J=8.82, 2.71 Hz, 1 H) 7.64 (d, J=2.71 Hz, 1 H) 7.95 (s, 2 H).

Example 12B

N-[(2Z)-5-tert-butyl-3-{2-[(methylsulfonyl)amino]ethyl}-1,3-thiazol-2(3H)-ylidene]-5-chloro-2-methoxybenzamide A solution of Example 12A (0.29 g, 0.79 mmol) in tetrahydrofuran (10 mL) was treated with methanesulfonyl chloride (0.6 mL, 0.79 mmol) and triethylamine (0.33 mL, 0.24 mmol) and stirred at room temperature for 1 hour. The mixture was diluted with ethyl acetate, washed with water, brine, dried with $MgSO_4$, filtered, and concentrated. The residue was purified by flash chromatography ($SiO_2$, eluting with a gradient from 0 to 100% ethyl acetate in hexane over 600 mL then isocratic for 300 mL) to provide the title compound (0.28 g, 0.63 mMol, 80% yield). MS (DCI/$NH_3$) m/z 446.1 $(M+H)^+$. $^1H$ NMR (300 MHz, $CDCl_3$) δ ppm 1.36 (s, 9 H) 2.78 (s, 3 H) 3.62 (ddd, J=6.94, 5.55, 4.16 Hz, 2 H) 3.92 (s, 3

H) 4.33-4.39 (m, 2 H) 5.80 (t, J=5.35 Hz, 1 H) 6.70 (s, 1 H) 6.93 (d, J=9.12 Hz, 1 H) 7.35 (dd, J=9.12, 2.78 Hz, 1 H) 7.89 (d, J=2.78 Hz, 1 H).

Example 13

N-[(2Z)-5-tert-butyl-3-{2-[(ethylsulfonyl)(methyl) amino]ethyl}-1,3-thiazol-2(3H)-ylidene]-5-chloro-2-methoxybenzamide Example 10D (0.17 g, 0.45 mmol), ethanesulfonyl chloride (98% 0.043 mL, 0.45 mmol), and triethylamine (0.19 mL, 1.35 mmol) were mixed in 5 mL of tetrahydrofuran and stirred at room temperature for 1 hour. The reaction was diluted with 100 mL ethyl acetate, washed with water, brine, dried with $MgSO_4$, filtered, and concentrated. The concentrate was purified by flash chromatography ($SiO_2$, eluting with a gradient from 0 to 60% ethyl acetate in hexane over 600 mL then isocratic for 300 mL) to provide the title compound (0.12 g, 0.25 mMol, 57% yield). MS ($DCI/NH_3$) m/z 474.2 $(M+H)^+$. $^1H$ NMR (300 MHz, $CDCl_3$) δ ppm 1.32 (t, J=7.46 Hz, 3 H) 1.35 (s, 9 H) 2.85 (s, 3 H) 2.96 (q, J=7.46 Hz, 2 H) 3.62-3.68 (m, 2 H) 3.91 (s, 3 H) 4.37 (t, J=6.44 Hz, 2 H) 6.75 (s, 1 H) 6.92 (d, J=8.82 Hz, 1 H) 7.34 (dd, J=8.82, 3.05 Hz, 1 H) 8.00 (d, J=2.71 Hz, 1 H).

Example 14

5-chloro-N-[(2Z)-3-[(6-fluoropyridin-3-yl)methyl]-5-methyl-1,3-thiazol-2(3H)-ylidene]-2-methoxybenzamide Example 14A 2-fluoro-5-(methylsulfonylmethyl)pyridine (6-Fluoropyridin-3-yl)methanol (215 mg, 1.69 mmol) in $CH_2Cl_2$ (10 mL) containing triethylamine (354 μL, 2.54 mmol) was treated with methanesulfonyl chloride (291 mg, 2.54 mmol) dropwise at 0° C., stirred at 0° C. for 30 min, diluted with water, and extracted with $CH_2Cl_2$ (2×10 mL). The combined organic extract was dried ($MgSO_4$), filtered, and concentrated to afford a crude oil.

Example 14B 5-chloro-N-[(2Z)-3-[(6-fluoropyridin-3-yl)methyl]-5-methyl-1,3-thiazol-2(3H)-ylidene]-2-methoxybenzamide The product from Example 18 A (125 mg, 0.44 mmol) in tetrahydrofuran/N,N-dimethylformamide (1:2) (5 mL) was treated with NaH (60%, 35 mg, 0.88 mmol), stirred for min at room temperature, and then treated with Example 14A (318 mg, 1.69 mmol). The mixture was heated at 75° C. for 12 hrs. After cooling, the mixture was diluted with water, and extracted with ethyl acetate. The organic extract was dried ($MgSO_4$), filtered, and concentrated. The concentrate was purified by reverse phase HPLC on a Waters Symmetry C8 column (25 mm×100 mm, 7 μm particle size) using a gradient of 10% to 100% acetonitrile:0.1% aqueous trifluoroacetic acid over 8 minutes (10 minutes run time) at a flow rate of 40 mL/minutes) to afford 24 mg (14%) of the title compound. $^1H$ NMR (500 MHz, DMSO-$d_6$) δ ppm 2.27 (s, 3 H) 3.80 (s, 3 H) 5.38 (s, 2 H) 7.12 (d, J=8.85 Hz, 1 H) 7.21 (dd, J=8.54, 2.75 Hz, 1 H) 7.46 (dd, J=8.85, 2.75 Hz, 2 H) 7.64 (d, J=2.75 Hz, 1 H) 8.03 (td, J=8.24, 2.75 Hz, 1 H) 8.37 (d, J=2.14 Hz, 1 H); MS (ESI) m/z 392 $(M+H)^+$.

Example 15

N-[(2Z)-3-[(2R)-azetidin-2-ylmethyl]-5-tert-butyl-1,3-thiazol-2(3H)-ylidene]-5-chloro-2-methoxybenzamide Example 15A (R)-tert-butyl 2-(tosyloxymethyl)azetidine-1-carboxylate Commercially available (R)-tert-butyl 2-(hydroxymethyl) azetidine-1-carboxylate (1.8 g, 9.61 mmol) in pyridine was treated with p-toluenesulfonyl chloride (1.83 g, 9.61 mmol). The reaction mixture was stirred at room temperature for 20 h then poured into water and extracted with ethyl acetate. The ethyl acetate layer was washed with water (3×75 mL) and then dried ($MgSO_4$), filtered, and concentrated in vacuo to afford the titled compound. MS (DCI) m/z 342 $(M+H)^+$.

Example 15B (S,Z)-tert-butyl 2-((5-tert-butyl-2-(5-chloro-2-methoxybenzoylimino)thiazol-3(2H)-yl)methyl)azetidine-1-carboxylate To a solution of Example 4C (0.4 g, 1.23 mmol) in N,N-dimethylformamide (20 mL) at 0° C. was added sodium hydride (60% dispersion in mineral oil, 0.049 g, 10.3 mmol). The reaction mixture was stirred for 30 min. and then treated with Example 15A (0.42 g, 1.23 mmol). The resulting mixture was stirred at room temperature for 18 hr, poured into water (100 mL) and extracted with ethyl acetate (2×100 mL). The organics were washed with water and brine (2×100 mL), dried over $MgSO_4$, filtered, and concentrated. The residue was purified by flash chromatography using an Analogix® Intelliflash280 ™ ($SiO_2$, 0-50% ethyl acetate in hexanes) to afford the title compound (345 mg, 56% yield). MS (DCI) m/z 494 $(M+H)^+$.

Example 15C

N-[(2Z)-3-[(2R)-azetidin-2-ylmethyl]-5-tert-butyl-1,3-thiazol-2(3H)—)-ylidene]-5-chloro-2-methoxy-benzamide A solution of Example 15B (295 mg, 0.6 mmol) in $CH_2Cl_2$ (5 mL) was treated with trifluoroacetic acid (1 mL) and the reaction mixture was stirred at room temperature for 48 hrs, concentrated on the rotovap and the residue was partitioned between ethyl acetate and saturated $NaHCO_3$. The organic layer was washed with brine, dried ($MgSO_4$), filtered, and concentrated in vacuo. The residue was purified by flash chromatography using an Analogix® Intelliflash280 ™ ($SiO_2$, 0-15% methanol in $CH_2Cl_2$) to afford the title compound (160 mg, 68% yield). MS (DCI) m/z 394 $(M+H)^+$. $^1H$ NMR (300 MHz, DMSO -$d_6$) δ ppm 1.17-1.27 (m, 2 H), 1.28-1.35 (s, 9 H), 2.05-2.19 (m, 1 H), 2.19-2.34 (m, 1 H), 3.45-3.61 (m, 1 H), 3.72-3.82 (m, 3 H), 4.20-4.35 (m, 3 H), 7.11 (d, J=8.7 Hz, 1 H), 7.30 (s, 1 H), 7.45 (dd, J=8.7, 2.8 Hz, 1 H), 7.61 (d, J=2.8 Hz, 1 H). MS (DCI) m/z 394 $(M+H)^+$.

Example 16

5-chloro-N-[(2Z)-5-chloro-3-(1,3-thiazol-4-ylmethyl)-1,3-thiazol-2(3H)-ylidene]-2-methoxybenzamide

Example 16A

N-(5-chlorothiazol-2-yl)-5-chloro-2-methoxybenzamide

Commercially available 5-chlorothiazol-2-amine and Example 3D were processed using the method described for Example 4C to afford the title compound. MS (DCI) m/z 304 $(M+H)^+$.

Example 16B 5-chloro-N-[(2Z)-5-chloro-3-(1,3-thiazol-4-ylmethyl)-1,3-thiazol-2(3H)-ylidene]-2-methoxybenzamide A mixture of Example 16A (1001 mg, 3.33 mmol), commercially available 4-(chloromethyl)thiazole (574 mg, 3.33 mmol), potassium t-butoxide (354 mg, 3.33 mmol) and tetrabutylammonium iodide (492 mg, 1.33 mmol) in anhydrous toluene (30 mL)/dioxane (10 mL) was refluxed for 15 h. The mixture was then cooled to room temperature, washed with water, brine, dried with anhydrous MgSO$_4$, filtered, and concentrated under reduced pressure. The residue was purified using an Analogix® Intelliflash280™ (SiO$_2$, 0-70% ethyl acetate in hexanes) to afford the title compound. 800 mg, 60% yield. $^1$H NMR (300 MHz, DMSO-d$_6$) δ ppm 3.79 (s, 3 H), 5.54 (s, 2 H), 7.13 (d, J=8.7 Hz, 1 H), 7.49 (dd, J=8.7, 2.8 Hz, 1 H), 7.70 (dd, J=16.3, 2.4 Hz, 2 H), 7.91 (s, 1 H), 9.10 (d, J=2.0 Hz, 1 H). MS (DCI) m/z 401 $(M+H)^+$; Anal. Calculated for C$_{15}$H$_{11}$Cl$_2$N$_3$O$_2$S$_2$: C, 45.01; H, 2.77; N, 10.50. Found: C, 44.83; H, 2.71; N, 10.16.

Example 17

N-[(2Z)-5-bromo-3-(1,3-thiazol-4-ylmethyl)-1,3-thiazol-2(3H)-ylidene]-5-chloro-2-methoxybenzamide

Example 17A

N-(5-bromothiazol-2-yl)-5-chloro-2-methoxybenzamide

Commercially available 5-bromothiazol-2-amine and Example 3D were processed using the method described for Example 4C to afford the title compound. MS (DCI) m/z 348 $(M+H)^+$.

Example 17B

N-[(2Z)-5-bromo-3-(1,3-thiazol-4-ylmethyl)-1,3-thiazol-2(3H)-ylidene]-5-chloro-2-methoxybenzamide A mixture of Example 17A (1001 mg, 3.33 mmol) and commercially available 4-(bromomethyl)thiazole were processed using the method described for Example 16B to afford the title compound (660 mg, 52% yield). $^1$H NMR (300 MHz, DMSO-d$_6$) δ ppm 3.78 (s, 3 H), 5.54 (s, 2 H), 7.12 (d, J=9.2 Hz, 1 H), 7.49 (dd, J=8.8, 2.7 Hz, 1 H), 7.69 (dd, J=15.9, 2.4 Hz, 2 H), 7.93 (s, 1 H), 9.10 (d, J=2.0 Hz, 1 H) MS (DCI) m/z 445 $(M+H)^+$; Anal. Calculated for C$_{15}$H$_{11}$BrClN$_3$O$_2$S$_2$: C, 40.51; H, 2.49; N, 9.45. Found: C, 40.85; H, 2.90; N, 9.62.

Example 18

5-chloro-2-methoxy-N-[(2Z)-5-methyl-3-(1,3-thiazol-4-ylmethyl)-1,3-thiazol-2(3H)-ylidene]benzamide

Example 18A 5-chloro-2-methoxy-N-(5-methylthiazol-2-yl)benzamide

Commercially available 5-methylthiazol-2-amine and Example 3D were processed using the method described for Example 4C to afford the title compound. MS (DCI) m/z 283 $(M+H)^+$.

Example 18B 5-chloro-2-methoxy-N-[(2Z)-5-methyl-3-(1,3-thiazol-4-ylmethyl)-1,3-thiazol-2(3H)-ylidene]benzamide To a solution of Example 18A (2.65 g, 9.4 mmol) in N,N-dimethylformamide (20 mL) at 0° C. was added sodium hydride (60% dispersion in mineral oil, 0.247 g, 10.3 mmol). The reaction mixture was stirred for 30 min. and then treated with commercially available 4-(chloromethyl)thiazole (1.25 g, 9.4 mmol). The resulting mixture was stirred at room temperature for 18 h, poured into water (100 mL) and extracted with ethyl acetate (2×100 mL). The organics were washed with water, brine (2×100 mL), dried over MgSO$_4$, filtered, and concentrated. The residue was purified by using an Analogix® Intelliflash280 ™ (SiO$_2$, 0-50% ethyl acetate in hexanes) to afford the title compound (2.56 g, 72% yield). $^1$H NMR (300 MHz, DMSO-d$_6$) δ ppm 2.28 (s, 3 H), 3.77 (s, 3 H), 5.50 (s, 2 H), 7.10 (d, J=8.7 Hz, 1H), 7.31 (d, J=1.6 Hz, 1 H), 7.38-7.52 (m, 2 H), 7.63 (dd, J=14.5, 2.6 Hz, 1 H), 9.09 (d, J=2.0 Hz, 1 H). MS (DCI) m/z 398 $(M+H)^+$; MS (DCI) m/z 380 $(M+H)^+$. Anal. Calculated for C$_{16}$H$_{14}$ClN$_3$O$_2$S$_2$: C, 50.59; H, 3.71; N, 11.06. Found: C, 50.57; H, 3.02; N, 11.03.

Example 19

N-[(2Z)-5-tert-butyl-3-(1,3-thiazol-4-ylmethyl)-1,3,4-thiadiazol-2(3H)-ylidene]-5-chloro-2-methoxybenzamide A mixture of Example 6A (489 mg, 1.5 mmol), commercially available 4-(chloromethyl)thiazole (200 mg, 1.5 mmol), potassium carbonate (415 mg, 3.0 mmol), tetrabutylammonium iodide (15 mg, 0.04 mmol), tetrabutylammonium hydrogensulfate (15 mg, 0.04 mmol) and tetraethylammonium iodide (15 mg, 0.05 mmol) in anhydrous toluene (50 mL) was refluxed for 15 h. The mixture was then cooled to room temperature, washed with water, brine, dried with anhydrous MgSO$_4$, filtered, and concentrated under reduced pressure. The residue was purified by using an Analogix® Intelliflash280™ (SiO$_2$, 0-60% ethyl acetate in hexanes) to afford the title compound (300 mg, 47% yield). $^1$H NMR (300 MHz, DMSO-d$_6$) δ ppm 1.37 (s, 9 H), 3.78 (s, 3 H), 5.69 (s, 2 H), 7.13 (d, J=9.2 Hz, 1 H), 7.49 (dd, J=8.8, 2.7 Hz, 1 H), 7.61 (d, J=2.0 Hz, 1 H), 7.71 (d, J=3.1 Hz, 1 H), 9.08 (d, J=2.0 Hz, 1

H) MS (DCI) m/z 423 (M+H)+. Anal. Calculated for $C_{18}H_{19}ClN_4O_2S_2$: C, 51.12; H, 4.53; N, 13.25. Found: C, 50.85; H, 4.32; N, 13.11.

Example 20

2,5-dichloro-N-[(2Z)-5-methyl-3-[(2-methyl-1,3-thiazol-4-yl)methyl]-1,3-thiazol-2(3H)-ylidene]benzamide

Example 20A 2,5-dichloro-N-(5-methylthiazol-2-yl)benzamide

To a solution of 5-methylthiazole-2-amine (Aldrich, 1.0 g, 8.76 mmol) in tetrahydrofuran (10 mL) was added 2,5-dichlorobenzoic acid (Aldrich) (2.01 g, 10.51 mmol), triethylamine (2.93 mL, 21.02 mmol), and 1-propanephosphonic acid cyclic anhydride (Aldrich, 50% solution in ethyl acetate, 6.19 mL, 10.51 mmol). The reaction mixture was stirred at 22° C. for 14 h., cooled, and quenched with saturated aqueous $NaHCO_3$ (20 mL). The aqueous layer was extracted with ethyl acetate (2×40 mL). The combined organic extracts were dried over anhydrous $Na_2SO_4$, filtered, and concentrated under reduced pressure. The residue was purified by column chromatography using an Analogix® Intelliflash280 ™ ($SiO_2$, 0-100% ethyl acetate in hexanes) to afford 1.99 g of the title compound. MS (ESI+) m/z 287 (M+H)+.

Example 20B 2,5-dichloro-N-[(2Z)-5-methyl-3-[(2-methyl-1,3-thiazol-4-yl)methyl]-1,3-thiazol-2(3H)-ylidene]benzamide To a solution of Example 20A (0.6 g, 2.1 mmol) in N,N-dimethylformamide/tetrahydrofuran (1:4, 20 mL) were added sodium hydride (60% dispersion in mineral oil, 0.1 g, 2.5 mmol), tetrabutylammonium iodide (0.09, 0.23 mmol) and commercially available 4-(chloromethyl)-2-methylthiazole (Maybridge, 0.37 g, 2.5 mmol). The reaction mixture was stirred at 80° C. for 16 hours, cooled, diluted with ethyl acetate (20 mL) and quenched with saturated aqueous $NaHCO_3$ (20 mL). The aqueous layer was extracted with ethyl acetate (2×20 mL). The combined organic layers were washed with water (1×25 mL), dried over anhydrous $Na_2SO_4$, filtered, and concentrated under reduced pressure. The residue was purified by column chromatography using an Analogix® Intelliflash280 ™ ($SiO_2$, 0-50% ethyl acetate in hexanes) to afford the title compound. $^1$H NMR (300 MHz, DMSO-$d_6$) δ ppm 2.30 (s, 3 H), 2.63 (s, 3 H), 5.42 (s, 2 H), 7.34-7.39 (m, 2 H), 7.51 (s, 1 H), 7.52 (s, 1 H), 7.88 (t, J=1.5 Hz, 1 H); MS (ESI+) m/z 398 (M+H)+; Anal. Calculated for $C_{16}H_{13}Cl_2N_3OS_2$ 0.75$H_2O$: C, 48.24; H, 3.29; N, 10.55. Found: C, 46.35; H, 3.46; N, 9.97.

Example 21

5-chloro-2-methoxy-N-[(2Z)-5-methyl-3-[(2-methyl-1,3-thiazol-4-yl)methyl]-1,3-thiazol-2(3H)-ylidene]benzamide Example 18A, sodium hydride (60% dispersion in mineral oil), tetrabutylammonium iodide and commercially available 4-(chloromethyl)-2-methylthiazole (Maybridge) were processed using the method described in Example 20B to afford the title compound. $^1$H NMR (300 MHz, dimethylsulfoxide-$d_6$) δ ppm 2.28 (s, 3 H), 2.63 (s, 3 H), 3.78 (s, 3 H), 5.38 (s, 2 H), 7.10 (d, J=9.1 Hz, 1 H), 7.29 (d, J=1.2 Hz, 1H), 7.35 (s, 1 H), 7.44 (dd, 1 H), 7.68 (d, J=2.8 Hz, 1 H); MS (ESI+) m/z 394 (M+H)+.

Example 22

5-chloro-2-methoxy-N-[(2Z)-5-methyl-3-(1,3-thiazol-2-ylmethyl)-1,3-thiazol-2(3H)-ylidene]benzamide Example 18A, sodium hydride (60% dispersion in mineral oil), tetrabutylammonium iodide and commercially available 2-(chloromethyl)thiazole (Chembridge) were processed using the method described in Example 20B to afford the title compound. $^1$H NMR (300 MHz, DMSO-$d_6$) δ ppm 2.29 (s, 3H), 3.77 (s, 3H), 5.68 (s, 2H), 7.10 (d, J=8.8 Hz, 1H), 7.40 (d, J=1.4 Hz, 1H), 7.45 (dd, J=8.8, 3.1 Hz, 1H), 7.71-7.76 (m, 2H), 7.76-7.85 (m, 1 H); MS (ESI+) m/z 380 (M+H)+; Anal. Calculated for $C_{16}H_{14}ClN_3O_2S_2$: C, 50.59; H, 3.71; N, 11.06. Found: C, 50.40; H, 3.45; N, 11.00.

Example 23

5-chloro-2-methoxy-N-[(2Z)-5-methyl-3-[(4-methyl-1,3-thiazol-2-yl)methyl]-1,3-thiazol-2(3H)-ylidene]benzamide Example 18A, sodium hydride (60% dispersion in mineral oil), tetrabutylammonium iodide and commercially available 2-(chloromethyl)-4-methylthiazole (Chembridge) were processed using the method described in Example 20B to afford the title compound. $^1$H NMR (300 MHz, DMSO-$d_6$) δ ppm 2.29 (s, 3 H), 2.34 (s, 3 H), 3.77 (s, 3 H), 5.61 (s, 2 H), 7.11 (d, J=8.7 Hz, 1 H), 7.25 (d, J=1.2 Hz, 1 H), 7.40 (d, J=1.6 Hz, 1 H), 7.46 (dd, J=8.7, 2.8 Hz, 1 H), 7.76 (d, J=2.8 Hz, 1 H); MS (ESI+) m/z 394 (M+H)+; Anal. Calculated for $C_{17}H_{16}ClN_3O_2S_2$: C, 51.83; H, 4.09; N, 10.67. Found: C, 51.88; H, 3.80; N, 10.53.

Example 24

5-chloro-N-[(2Z)-3-[(6-chloropyridin-3-yl)methyl]-5-methyl-1,3-thiazol-2(3H)-ylidene]-2-methoxybenzamide Example 18A, sodium hydride (60% dispersion in mineral oil), and commercially available 2-chloro-5-chloromethylpyridine were processed using the method described in Example 20B to afford the title compound. $^1$H NMR (300 MHz, DMSO-$d_6$) δ ppm 2.27 (s, 3 H), 3.79 (s, 3 H), 5.38 (s, 2 H), 7.12 (d, J=8.8 Hz, 1 H), 7.42-7.44 (m, 1 H), 7.44-7.49 (m, 1H), 7.51-7.58 (m, J=8.5 Hz, 1 H), 7.62 (d, J=3.1 Hz, 1 H), 7.86 (dd, J=8.1, 2.4 Hz, 1 H), 8.46-8.58 (m, 1 H); MS (ESI) m/z 408 (M+H)+

Example 25

5-chloro-2-methoxy-N-[(2Z)-5-methyl-3-{[6-(trifluoromethyl)pyridin-3-yl]methyl}-1,3-thiazol-2(3H)-ylidene]benzamide Example 18A, sodium hydride (60% dispersion in mineral oil), and commercially available 3-(chloromethyl)-6-(trifluoromethyl)pyridine were processed using the method described in Example 20B to afford the title compound. $^1$H NMR (300 MHz, DMSO-$d_6$) δ ppm 2.29 (s, 3 H), 3.76 (s, 3

H), 5.48 (s, 2 H), 7.08 (s, 1 H), 7.34 (d, J=1.4 Hz, 1 H), 7.44 (dd, J=8.8, 2.7 Hz, 1 H), 7.57-7.67 (m, 2 H), 8.41-8.62 (m, 2 H); MS (ESI) m/z 442 (M+H)$^+$

Example 26

N-[(2Z)-5-tert-butyl-3-(1,3-thiazol-4-ylmethyl)-1,3-thiazol-2(3H)-ylidene]-5-chloro-2-methoxybenzamide To a solution of Example 4C (0.75 g, 2.31 mmol) in N,N-dimethylformamide/tetrahydrofuran (1:4, 20 mL) were added potassium tert-butoxide (0.77 g, 6.93 mmol), tetrabutylammonium iodide (0.09, 0.23 mmol) and the commercially available HCl salt of 4-(chloromethyl)thiazole (TCI-US, 0.59 g, 3.46 mmol). The reaction mixture was stirred at 80° C. for 16 hours, cooled, diluted with ethyl acetate (20 mL) and quenched with saturated aqueous NaHCO$_3$ (20 mL). The aqueous layer was extracted with ethyl acetate (2×20 mL). The combined organic layers were washed with water (1×25 mL), dried over anhydrous Na$_2$SO$_4$, filtered, and concentrated under reduced pressure. The residue was purified by column chromatography using an Analogix® Intelliflash280™ (SiO$_2$, 0-100% ethyl acetate in hexanes) to afford the title compound. $^1$H NMR (300 MHz, DMSO-d$_6$) δ ppm 1.32 (s, 9 H), 3.76 (s, 3 H), 5.49 (s, 2 H), 7.09 (d, J=9.2 Hz, 1 H), 7.36 (s, 1 H), 7.44 (dd, J=9.0, 2.9 Hz, 1 H), 7.57 (d, J=2.0 Hz, 1 H), 7.61 (d, J=3.1 Hz, 1 H), 9.10 (d, J=2.0 Hz, 1 H); MS (ESI) m/z 422 (M+H)$^+$; Anal. Calculated for C$_{19}$H$_{20}$ClN$_3$O$_2$S$_2$: C, 54.08; H, 4.78; N, 9.96. Found: C, 54.10; H, 4.62; N, 9.81.

Example 27

2-ethoxy-N-[(2Z)-5-methyl-3-[3-(1H-pyrrol-1-yl)propyl]-1,3-thiazol-2(3H)-ylidene]benzamide Example 27A 3-(3-(1H-pyrrol-1-yl)propyl)-5-methylthiazol-2(3H)-imine A mixture of 2-amino-5-methylthiazole (0.55 g, 4.8 mmol) and 1-(3-bromopropyl)pyrrole (TCI-US, 1.0 g, 5.3 mmol) was warmed to 85° C. and was stirred for 2 h. The mixture was then cooled to ambient temperature and was purified by flash column chromatography (SiO$_2$, 10% CH$_3$OH in ethyl acetate then 9:1:0.1 CH$_2$Cl$_2$:CH$_3$OH:NH$_4$OH) to give the title compound (0.86 g, 3.9 mmol, 81% yield). MS (DCI/NH$_3$) m/z 222 (M+NH$_4$)$^+$.

Example 27B 2-ethoxy-N-[(2Z)-5-methyl-3-[3-(1H-pyrrol-1-yl)propyl]-1,3-thiazol-2(3H)-ylidene]benzamide To a solution of the product of Example 27A (0.22 g, 1.0 mmol) in tetrahydrofuran (15 mL) and N,N-dimethylformamide (2 mL) was added triethyl amine (0.42 mL, 3 mmol) followed by 2-ethoxybenzoyl chloride (0.25 g, 1.3 mmol). This mixture was stirred at ambient temperature for 18 h then was concentrated under reduced pressure. The residue was diluted with 5 mL saturated aqueous NH$_4$Cl, 2 mL H$_2$O, and 5 mL ethyl acetate. The layers were separated and the aqueous layer was extracted with 3×5 mL ethyl acetate. The combined organics were dried over anhydrous Na$_2$SO$_4$, filtered, and concentrated under reduced pressure. The concentrate was purified by column chromatography (SiO$_2$, 50% hexanes in ethyl acetate) to give the title compound (0.22 g, 0.6 mmol, 60% yield). $^1$H NMR (300 MHz, CD$_3$OD) δ ppm 1.37 (t, J=7.0 Hz, 3 H), 2.24-2.38 (m, 2 H), 2.31 (d, J=1.4 Hz, 3 H), 3.98 (t, J=6.8 Hz, 2 H), 4.10 (q, J=7.0 Hz, 2 H), 4.18 (dd, J=7.1 Hz, 2 H), 6.03 (t, J=2.2 Hz, 2 H), 6.70 (t, J=2.0 Hz, 2 H), 6.93-7.00 (m, 2 H), 7.04 (d, J=8.1 Hz, 1 H), 7.39 (ddd, J=8.4, 7.4, 1.9 Hz, 1 H), 7.77 (dd, J=7.6, 1.9 Hz, 1 H); MS (DCI/NH$_3$) m/z 370 (M+H)$^+$; Anal. calculated for C$_{20}$H$_{23}$N$_3$O$_2$S: C, 65.01; H, 6.27; N, 11.37. Found: C, 64.66; H, 6.35; N, 11.35.

Example 28

5-chloro-2-methoxy-N-[(2Z)-5-methyl-3-[3-(1H-pyrrol-1-yl)propyl]-1,3-thiazol-2(3H)-ylidene]benzamide To the product of Example 27A (0.25 g, 1.13 mmol) in tetrahydrofuran (15 mL) and N,N-dimethylformamide (2 mL) was added triethyl amine (0.47 mL, 3.4 mmol) followed by Example 3D (1.5 mmol). This mixture was warmed to 45° C. and was allowed to stir for 2 h then was allowed to cool to ambient temperature and was stirred for an additional 72 h. The mixture was concentrated under reduced pressure and the residue was diluted with 5 mL saturated aqueous NH$_4$Cl, 2 mL H$_2$O, and 5 mL ethyl acetate. The layers were separated and the aqueous layer was extracted with 3×5 mL ethyl acetate. The combined organics were dried over anhydrous Na$_2$SO$_4$, filtered, and concentrated under reduced pressure. The concentrate was purified by column chromatography (SiO$_2$, 50% hexanes in ethyl acetate) to give the title compound (0.25 g, 0.64 mmol, 57% yield). $^1$H NMR (300 MHz, CD$_3$OD) δ ppm 2.26-2.38 (m, 2 H), 2.32 (d, J=1.0 Hz, 3 H), 3.83 (s, 3 H), 3.98 (t, J=6.8 Hz, 2 H), 4.18 (dd, J=7.1 Hz, 2 H), 6.04 (t, J=2.2 Hz, 2 H), 6.70 (t, J=2.2 Hz, 2 H), 7.00 (q, J=1.1 Hz, 1 H), 7.07 (d, J=8.8 Hz, 1 H), 7.40 (dd, J=9.0, 2.9 Hz, 1 H), 7.81 (d, J=2.7 Hz, 1 H); MS (DCI/NH$_3$) m/z 390 (M+H)$^+$; Anal. calculated for C$_{19}$H$_{20}$ClN$_3$O$_2$S: C, 58.53; H, 5.17; N, 10.78. Found: C, 58.28; H, 5.13; N, 10.59.

Example 29

N-[(2Z)-5-tert-butyl-3-[(2S)-pyrrolidin-2-ylmethyl]-1,3-thiazol-2(3H)-ylidene]-5-chloro-2-methoxybenzamide Example 29A (S)-tert-butyl 2-((5-tert-butyl-2-iminothiazol-3(2H)-yl)methyl)pyrrolidine-1-carboxylate To a solution of 3,3-dimethylbutanal (130 mg, 1.30 mmol) in acetonitrile (8 mL) was added molecular sieves (4A beads, 8-12 mesh, 0.7 g) and (S)-tert-butyl 2-(aminomethyl)pyrrolidine-1-carboxylate (260 mg, 1.30 mmol). The mixture was stirred for 12 hr at room temperature, filtered, and washed with acetonitrile (5 mL). To this solution was added potassium thiocyanate (168 mg, 1.72 mmol) and the temperature was adjusted at 50° C. The reaction was stirred until all solids were dissolved then iodine (659 mg, 2.6 mmol) was added. The reaction mixture was stirred at 50° C. for another 12 hr, cooled to room temperature, and stirred with 20% sodium metabisulfite for 1 hr. The organic layer was separated and the aqueous layer was extracted with dichloromethane (3×10 mL). The combined organics were dried over sodium sulfate, filtered, and concentrated under reduced pressure to give the title compound. This intermediate was used without further purification. MS (DCI/NH$_3$) m/z 340 (M+H)$^+$.

Example 29B (S,Z)-tert-butyl 2-((5-tert-butyl-2-(5-chloro-2-methoxybenzoylimino)thiazol-3(2H)-yl)methyl)pyrrolidine-1-carboxylate To a solution of crude Example 29A (850 mg, 3.00 mmol) in dichloromethane (6 mL) was added triethylamine (0.419 mL, 3.00 mmol), followed by addition of Example 3D (513 mg, 2.504 mmol). The reaction was stirred overnight and washed with water, dried (MgSO$_4$), filtered, and concentrated. The residue was purified by column chromatography using an Analogix® Intelliflash280™ (SiO$_2$, 0-100% ethyl acetate in hexanes) to afford the title compound. $^1$H NMR (300 MHz, DMSO-d$_6$) δ ppm 1.14-1.28 (m, 9 H) 1.29 (s, 9 H) 1.52-1.64 (m, 4 H) 3.33-3.38 (m, 2 H) 3.78 (s, 3 H) 3.83-3.89 (m, 1 H) 4.00-4.06 (m, 1 H) 4.30-4.40 (m, 1 H) 7.07-7.11 (m, 1 H) 7.16-7.22 (m, 1 H) 7.39-7.47 (m, 1 H) 7.65-7.71 (m, 1 H) MS (DCI) m/z 508 (M+H)$^+$.

Example 29C

N-[(2Z)-5-tert-butyl-3-[(2S)-pyrrolidin-2-ylmethyl]-1,3-thiazol-2(3H)-ylidene]-5-chloro-2-methoxybenzamide To a solution of Example 29B (140 mg, 0.28 mmol.) in methanol (2 mL) was added hydrogen chloride in dioxane (0.5 mL, 2.000 mmol) and stirred for 12 hr. The solvent was removed under reduced pressure and the residue recrystallized from methanol:diethyl ether to provide the title compound as a hydrogen chloride salt. $^1$H NMR (300 MHz, DMSO-d$_6$) δ ppm 1.33 (s, 9 H) 1.68-1.79 (m, 1 H) 1.87-2.01 (m, 2 H) 2.03-2.12 (m, 1 H) 3.14-3.28 (m, 2 H) 3.81 (s, 3 H) 3.93-4.06 (m, 1 H) 4.47 (d, J=6.44 Hz, 2 H) 7.14 (d, J=9.16 Hz, 1 H) 7.45-7.50 (m, 2 H) 7.63 (d, J=2.71 Hz, 1 H) 9.29 (d, J=4.41 Hz, 2 H); MS (DCI) m/z 408 (M+H)$^+$. Anal. calcd for C$_{20}$H$_{26}$ClN$_3$O$_2$S.2HCl.1.0H$_2$O: C, 48.15; H, 6.06; N, 8.42. Found: C, 48.00; H, 6.04; N, 8.27.

Example 30

N-[(2Z)-5-tert-butyl-3-[(2S)-piperidin-2-ylmethyl]-1,3-thiazol-2(3H)-ylidene]-5-chloro-2-methoxybenzamide

Example 30A (S)-tert-butyl 2-((5-tert-butyl-2-iminothiazol-3(2H)-yl)methyl)piperidine-1-carboxylate The title compound was prepared and isolated as described in Example 29A, substituting (S)-tert-butyl 2-(aminomethyl)piperidine-1-carboxylate for (S)-tert-butyl 2-(aminomethyl)pyrrolidine-1-carboxylate. MS (DCI/NH$_3$) m/z 354 (M+H)$^+$.

Example 30B (S,Z)-tert-butyl 2-((5-tert-butyl-2-(5-chloro-2-methoxybenzoylimino)thiazol-3(2H)-yl)methyl)piperidine-1-carboxylate The title compound was prepared and purified as described in Example 29B, substituting Example 30A for Example 29A. $^1$H NMR (300 MHz, DMSO-d$_6$) δ ppm 1.14-1.28 (m, 9 H) 1.29 (s, 9 H) 1.52-1.64 (m, 4 H) 1.67-1.72 (m, 2 H) 3.33-3.38 (m, 1 H) 3.78 (s, 3 H) 3.83-3.90 (m, 1 H) 4.00-4.04 (m, 1 H) 4.57-4.61 (m, 1 H) 4.70-4.74 (m, 1 H) 7.07-7.11 (m, 1 H) 7.16-7.22 (m, 1 H) 7.41-7.45 (m, 1 H) 7.65-7.71 (m, 1 H); MS (DCI/NH$_3$) m/z 522 (M+H)$^+$.

Example 30C

N-[(2Z)-5-tert-butyl-3-[(2S)-piperidin-2-ylmethyl]-1,3-thiazol-2(3H)-ylidene]-5-chloro-2-methoxybenzamide The HCl salt of the title compound was prepared and purified as described in Example 29C, substituting Example 30B for Example 29B. $^1$H NMR (300 MHz, DMSO-d$_6$) δ ppm 1.27-1.38 (s, 9 H) 1.48-1.64 (m, 3 H) 1.68-1.84 (m, 3 H) 2.85 (m, 1 H) 3.26 (m, 1 H) 3.39-3.54 (m, 1 H) 3.77-3.82 (m, 3 H) 4.30-4.45 (m, 2 H) 7.13 (d, J=9.12 Hz, 1 H) 7.33 (s, 1H) 7.46 (dd, J=8.92, 2.97 Hz, 1 H) 7.63 (d, J=2.78 Hz, 1 H) 8.89 (m, 1 H) 9.02 (m, 1 H); MS (DCI) m/z 422 (M+H)$^+$. Anal. calcd for C$_{21}$H$_{28}$ClN$_3$O$_2$S*3HCl: C, 47.47; H, 5.88; N, 7.91. Found: C, 47.60; H, 6.28; N, 8.00.

Example 31

N-[(2Z)-5-tert-butyl-3-[(2R)-piperidin-2-ylmethyl]-1,3-thiazol-2(3H)-ylidene]-5-chloro-2-methoxybenzamide

Example 31A (R)-tert-butyl 2-((5-tert-butyl-2-iminothiazol-3(2H)-yl)methyl)piperidine-1-carboxylate The title compound was prepared and isolated as described in Example 29A, substituting (R)-tert-butyl 2-(aminomethyl)piperidine-1-carboxylate for (S)-tert-butyl 2-(aminomethyl)pyrrolidine-1-carboxylate. MS (DCI/NH$_3$) m/z 354 (M+H)$^+$.

Example 31B (R,Z)-tert-butyl 2-((5-tert-butyl-2-(5-chloro-2-methoxybenzoylimino)thiazol-3(2H)-yl)methyl)piperidine-1-carboxylate The title compound was prepared and purified as described in Example 29B, substituting Example 31A for Example 29A. $^1$HNMR (300 MHz, DMSO-d$_6$) δ ppm 1.14-1.28 (m, 9 H) 1.29 (s, 9 H) 1.52-1.64 (m, 4 H) 1.67-1.72 (m, 2 H) 3.33-3.38 (m, 1 H) 3.78 (s, 3 H) 3.83-3.90 (m, 1 H) 4.00-4.04 (m, 1 H) 4.57-4.61 (m, 1 H) 4.70-4.74 (m, 1 H) 7.07-7.11 (m, 1 H) 7.16-7.22 (m, 1 H) 7.41-7.45 (m, 1 H) 7.65-7.71 (m, 1 H); MS (DCI/NH$_3$) m/z 522 (M+H)$^+$.

Example 31C

N-[(2Z)-5-tert-butyl-3-[(2R)-piperidin-2-ylmethyl]-1,3-thiazol-2(3H)-ylidene]-5-chloro-2-methoxybenzamide The HCl salt of the title compound was prepared and purified as described in Example 29C, substituting Example 31B for Example 29B. $^1$H NMR (300 MHz, DMSO-d$_6$) δ ppm 1.27-1.38 (s, 9 H) 1.48-1.64 (m, 3 H) 1.68-1.84 (m, 3 H) 2.85 (dm, 1 H) 3.26 (m, 1 H) 3.39-3.54 (m, 1 H) 3.77-3.80 (s, 3 H) 4.30-4.45 (m, 2 H) 7.13 (d, J=9.12 Hz, 1 H) 7.33 (s, 1 H) 7.46

(dd, J=8.92, 2.97 Hz, 1 H) 7.63 (d, J=2.78 Hz, 1 H) 8.89 (m, 1 H) 9.02 (m, 1 H); MS (DCI) m/z 422 (M+H)$^+$. Anal. calcd for $C_{21}H_{28}ClN_3O_2S \cdot 2HCl \cdot 0.5H_2O$: C, 47.49; H, 6.17; N, 7.91. Found: C, 47.64; H, 6.49; N, 7.87.

Example 32

N-[(2Z)-5-tert-butyl-3-{[(2S)-1-methylpyrrolidin-2-yl]methyl}-1,3-thiazol-2(3H)-ylidene]-5-chloro-2-methoxybenzamide To a solution of Example 29C (100 mg, 0.208 mmol) in dichloromethane (2 mL) and acetonitrile (2 mL) was added paraformaldehyde (63 mg, 2.098 mmol), followed by addition of sodium acetate (42.6 mg, 0.520 mmol) and sodium triacetoxyhydroborate (264 mg, 1.248 mmol) and stirred for 12 hr at 50° C. The reaction was concentrated and sodium carbonate (10%, 15 mL) was added to the residue and extracted with dichloromethane (3×20 mL). The organics were combined, washed with brine, dried (MgSO$_4$), filtered, and concentrated. The residue was purified by Analogix® Intelliflash280 ™ (SiO$_2$, 0-10% dichloromethane in methanol) to afford the title compound. $^1$H NMR (300 MHz, CD$_3$OD) δ ppm 1.37-1.42 (s, 9 H) 1.69-1.82 (m, 3 H) 1.89 (m, 1 H) 2.28-2.38 (m, 1 H) 2.42 (s, 3 H) 2.85-2.94 (m, 1 H) 3.04-3.12 (m, 1 H) 3.86 (s, 3 H) 4.07-4.16 (m, 1 H) 4.44 (dd, J=13.09, 4.76 Hz, 1 H) 7.07 (d, J=8.72 Hz, 1 H) 7.20 (s, 1 H) 7.40 (dd, J=9.12, 2.78 Hz, 1 H) 7.94 (d, J=2.78 Hz, 1 H); MS (DCI) m/z 422 (M+H)$^+$. Anal. calcd for $C_{21}H_{28}ClN_3O_2S \cdot 0.5$ ethyl acetate: C, 60.21; H, 6.98; N, 9.32. Found: C, 60.08; H, 6.77; N, 9.16.

Example 33

N-[(2Z)-5-tert-butyl-3-{[(2S)-1-methylpiperidin-2-yl]methyl}-1,3-thiazol-2(3H)-ylidene]-5-chloro-2-methoxybenzamide The title compound was prepared and purified as described in Example 32, substituting Example 30C for Example 29C. $^1$H NMR (300 MHz, CD$_3$OD) δ ppm 1.25-1.35 (m, 1 H) 1.38 (s, 9 H) 1.43-1.47 (m, 1 H) 1.56-1.66 (m, 2 H) 1.72-1.80 (m, 2 H) 2.21-2.27 (m, 1 H) 2.47 (s, 3 H) 2.64-2.73 (m, 1 H) 2.86-2.94 (m, 1 H) 3.86 (s, 3 H) 4.06 (dd, J=13.22, 8.81 Hz, 1 H) 4.71 (dd, J=13.22, 4.75 Hz, 1 H) 7.05-7.10 (m, 1 H) 7.16 (s, 1 H) 7.41 (dd, J=8.81, 2.71 Hz, 1 H) 7.97 (d, J=2.71 Hz, 1 H); MS (DCI) m/z 436 (M+H)$^+$. Anal. calcd for $C_{22}H_{30}ClN_3O_2S \cdot 0.1CH_2Cl_2$: C, 59.72; H, 6.85; N, 9.45. Found: C, 59.69; H, 6.48; N, 9.54.

Example 34

N-[(2Z)-5-tert-butyl-3-{[(2R)-1-methylpiperidin-2-yl]methyl}-1,3-thiazol-2(3H)-ylidene]-5-chloro-2-methoxybenzamide The title compound was prepared and purified as described in Example 32, substituting Example 31C for Example 29C. $^1$H NMR (300 MHz, CD$_3$OD) δ ppm 1.25-1.34 (m, 2 H) 1.37 (s, 9 H) 1.46 (m, 1 H) 1.55-1.67 (m, 2 H) 1.73-1.77 (m, 1 H) 2.20-2.29 (m, 1 H) 2.47 (s, 3 H) 2.64-2.73 (m, 1 H) 2.86-2.94 (m, 1 H) 3.87 (s, 3 H) 4.06 (dd, J=13.22, 8.82 Hz, 1 H) 4.70 (dd, J=13.22, 4.75 Hz, 1 H) 7.07 (d, J=8.81 Hz, 1 H) 7.15 (s, 1 H) 7.40 (dd, J=8.81, 2.71 Hz, 1 H) 7.96 (d, J=2.71 Hz, 1 H); MS (DCI) m/z 436 (M+H)$^+$. Anal. calcd for $C_{22}H_{30}ClN_3O_2S \cdot 0.1H_2O$: C, 60.35H, 6.95; N, 9.60. Found: C, 60.38; H, 6.87; N, 9.22.

Example 35

N-[(2Z)-5-tert-butyl-3-{[(2R)-1-ethylpiperidin-2-yl]methyl}-1,3-thiazol-2(3H)-ylidene]-5-chloro-2-methoxybenzamide The title compound was prepared and purified as described in Example 32, substituting Example 31C for Example 29C and acetaldehyde for paraformaldehyde. $^1$H NMR (300 MHz, CDCl$_3$) δ ppm 1.15 (t, J=7.12 Hz, 3 H) 1.28-1.43 (m, 11 H) 1.53-1.67 (m, 3 H) 1.68-1.78 (m, 1 H) 2.38-2.47 (m, 1 H) 2.74-2.82 (m, 1 H) 2.88-2.96 (m, 2 H) 3.00-3.10 (m, 1 H) 3.90 (s, 3 H) 3.98 (dd, J=13.22, 8.81 Hz, 1 H) 4.69 (dd, J=13.22, 4.41 Hz, 1 H) 6.66 (s, 1 H) 6.90 (d, J=9.15 Hz, 1 H) 7.33 (dd, J=8.81, 2.71 Hz, 1 H) 8.03 (d, J=3.05 Hz, 1 H); MS (DCI) m/z 450 (M+H)$^+$.

Example 36

N-[(2Z)-5-tert-butyl-3-[(3R)-piperidin-3-ylmethyl]-1,3-thiazol-2(3H)-ylidene]-5-chloro-2-methoxybenzamide Example 36A (R)-tert-butyl 3-(tosyloxymethyl)piperidine-1-carboxylate To a suspension of (R)-tert-butyl 3-(hydroxymethyl)piperidine-1-carboxylate (400 mg, 1.858 mmol) and pyridine (1.10 ml, 13.60 mmol) in tetrahydrofuran (5 ml) was added p-toluenesulfonyl chloride (425 mg, 2.230 mmol) and stirred for 10 hr. To the reaction was added citric acid (4 g) and water (10 mL) and extracted with ethyl acetate (3×10 mL). The organics were combined, dried (MgSO$_4$), filtered, and concentrated. The residue was purified by Analogix® Intelliflash280 ™ (SiO$_2$, 0-40% ethyl acetate in hexanes). $^1$H NMR (300 MHz, DMSO-d$_6$) δ ppm 1.13-1.21 (m, 1 H) 1.23-1.31 (m, 1 H) 1.37 (s, 9 H) 1.46-1.55 (m, 1 H) 1.59-1.74 (m, 2 H) 2.43 (s, 3 H) 2.68-2.83 (m, 1 H) 3.28-3.32 (m, 1H), 3.67-3.73 (m, 2 H) 3.89 (d, J=6.10 Hz, 2 H) 7.49 (m, 2 H) 7.76-7.81 (m, 2 H); MS (DCI) m/z 387 (M+NH$_4$)$^+$.

Example 36B (R,Z)-tert-butyl 3-((5-tert-butyl-2-(5-chloro-2-methoxybenzoylimino)thiazol-3(2H)-yl)methyl)piperidine-1-carboxylate To a solution of Example 4C (220 mg, 0.677 mmol) in toluene (5 mL) was added Example 36A, followed by addition of tetrabutylammonium iodide (100 mg, 0.271 mmol), potassium t-butoxide (91 mg, 0.812 mmol) and dioxane (0.4 mL). The reaction mixture was refluxed overnight. Water (15 mL) was added to the cooled reaction mixture and extracted with ethyl acetate (3×15 mL). The organics were combined, washed with brine, dried (MgSO$_4$), filtered, and concentrated. The residue was purified by Analogix® Intelliflash280 ™ (SiO$_2$, 0-30% ethyl acetate in hexanes) to provide the title compound. $^1$H NMR (300 MHz, CDCl$_3$) δ ppm 0.35 (s, 9 H) 1.42 (s, 9 H) 1.43-1.49 (m, 1 H) 1.66-1.82 (m, 2 H) 2.12-2.20 (m, 3 H) 2.83-2.89 (m, 1 H) 3.79 (dd, J=13.05, 3.56 Hz, 2 H) 3.90 (s, 3 H) 3.94-4.04 (m, 1 H) 4.11-4.15 (m, 1 H) 6.65 (s, 1 H) 6.90 (d, J=8.82 Hz, 1 H) 7.33 (dd, J=8.82, 2.71 Hz, 1 H) 7.96 (d, J=2.71 Hz, 1 H); MS (DCI) m/z 522 (M+H)$^+$.

Example 36C

N-[(2Z)-5-tert-butyl-3-[(3R)-piperidin-3-ylmethyl]-1,3-thiazol-2(3H)-ylidene]-5-chloro-2-methoxybenzamide The HCl salt of the title compound was prepared and purified as described in Example 29C, substituting Example 36B for Example 29B. $^1$H NMR (300 MHz, CD$_3$OD) δ ppm 1.44 (s, 9 H) 1.46-1.55 (m, 1 H) 1.71-1.83 (m, 1 H) 1.85-1.94 (m, 1 H) 1.97-2.08 (m, 1 H) 2.45-2.60 (m, 1 H) 2.85-3.01 (m, 2 H) 3.32-3.40 (m, 1 H) 3.63-3.76 (m, 1 H) 3.99 (s, 3 H) 4.37 (dd, J=7.54, 3.97 Hz, 2 H) 7.21 (d, J=8.73 Hz, 1 H) 7.50 (s, 1 H) 7.55 (dd, J=8.73, 2.78 Hz, 1 H) 7.90 (d, J=2.78 Hz, 1 H); MS (DCI) m/z 422 (M+H)$^+$. Anal. calcd for C$_{21}$H$_{28}$ClN$_3$O$_2$S.2HCl.2H$_2$O: C, 47.51; H, 6.45; N, 7.91. Found: C, 47.54; H, 6.56; N, 7.93.

Example 37

N-[(2Z)-5-tert-butyl-3-[(2R)-pyrrolidin-2-ylmethyl]-1,3-thiazol-2(3H)-ylidene]-5-chloro-2-methoxybenzamide

Example 37A (R)-tert-butyl 2-(tosyloxymethyl)pyrrolidine-1-carboxylate

The title compound was prepared and purified as described in Example 36A, substituting (R)-tert-butyl 2-(hydroxymethyl)pyrrolidine-1-carboxylate for (R)-tert-butyl 3-(hydroxymethyl)piperidine-1-carboxylate. $^1$H NMR (300 MHz, DMSO-d$_6$) δ ppm 1.28-1.35 (m, 9 H) 1.65-1.98 (m, 4 H) 2.42 (s, 3 H) 3.09-3.24 (m, 2 H) 3.79-3.85 (s, 1 H) 3.93-4.07 (m, 2 H) 7.49 (d, J=8.14 Hz, 2 H) 7.77 (d, J=8.14 Hz, 2 H); MS (DCI) m/z 373 (M+NH$_4$)$^+$.

Example 37B (R,Z)-tert-butyl 2-((5-tert-butyl-2-(5-chloro-2-methoxybenzoylimino)thiazol-3(2H)-yl)methyl)pyrrolidine-1-carboxylate The title compound was prepared and purified as described in Example 36B, substituting Example 37A for Example 36A. $^1$H NMR (300 MHz, CDCl$_3$) δ ppm 1.34 (s, 9 H) 1.38-1.44 (m, 1 H) 1.49 (s, 9 H) 1.75-1.91 (m, 2 H) 2.03-2.13 (m, 1 H) 3.31 (d, J=6.74 Hz, 2 H) 3.90 (s, 3 H) 4.11-4.25 (m, 1 H) 4.32-4.43 (m, 1 H) 4.43-4.56 (m, 1 H) 6.88-6.93 (m, 1 H) 7.33 (dd, J=8.73, 2.78 Hz, 1 H) 7.99 (s, 1 H); MS (DCI) m/z 508 (M+H)$^+$.

Example 37C

N-[(2Z)-5-tert-butyl-3-[(2R)-pyrrolidin-2-ylmethyl]-1,3-thiazol-2(3H)-ylidene]-5-chloro-2-methoxybenzamide The HCl salt of the title compound was prepared and purified as described in Example 29C, substituting Example 37B for Example 29B. $^1$H NMR (300 MHz, METHANOL-d$_4$) δ ppm 1.42 (s, 9 H) 1.79-1.92 (m, 1 H) 1.98-2.13 (m, 2 H) 2.23-2.36 (m, 1 H) 3.33-3.36 (m, 2 H) 3.92 (s, 3 H) 4.04-4.16 (m, 1 H) 4.59-4.71 (m, 2 H) 7.39 (s, 1 H) 7.48 (dd, J=8.72, 2.78 Hz, 1 H) 7.71 (d, J=2.78 Hz, 1 H); MS (DCI) m/z 408 (M+H)$^+$.

Example 38

N-[(2Z)-5-tert-butyl-3-[2-(2-oxopyrrolidin-1-yl)ethyl]-1,3-thiazol-2(3H)-ylidene]-5-chloro-2-methoxybenzamide

Example 38A 1-(2-(5-tert-butyl-2-iminothiazol-3(2H)-yl)ethyl)pyrrolidin-2-one The title compound was prepared and isolated as described in Example 29A, substituting 1-(2-aminoethyl)pyrrolidin-2-one hydrochloride (Matrix Scientific) for (S)-tert-butyl 2-(aminomethyl)pyrrolidine-1-carboxylate. MS (DCI/NH$_3$) m/z 268 (M+H)$^+$.

Example 38B

N-[(2Z)-5-tert-butyl-3-[2-(2-oxopyrrolidin-1-yl)ethyl]-1,3-thiazol-2(3H)-ylidene]-5-chloro-2-methoxybenzamide The title compound was prepared and purified as described in Example 29B, substituting Example 38A for Example 29A. $^1$H NMR (300 MHz, CDCl$_3$) δ ppm 1.39 (s, 9 H) 1.93-2.05 (m, 2 H) 2.37 (t, J=8.13 Hz, 2 H) 3.43 (t, J=6.94 Hz, 2 H) 3.77 (t, J=6.35 Hz, 2 H) 3.95 (s, 3 H) 4.54 (t, J=6.54 Hz, 2 H) 6.97 (d, J=8.72 Hz, 1 H) 7.04 (s, 1 H) 7.45 (dd, J=9.12, 2.78 Hz, 1 H) 7.95 (d, J=2.78 Hz, 1 H); MS (DCI) m/z 436 (M+H)$^+$. Anal. Calculated for C$_{21}$H$_{26}$ClN$_3$O$_3$S.1.7TFA: C, 46.53; H, 4.43; N, 6.67. Found: C, 46.29; H, 4.28; N, 6.39.

Example 39

N-[(2Z)-5-tert-butyl-3-[2-(2-oxopiperidin-1-yl)ethyl]-1,3-thiazol-2(3H)-ylidene]-5-chloro-2-methoxybenzamide

Example 39A 1-(2-(5-tert-butyl-2-iminothiazol-3(2H)-yl)ethyl)piperidin-2-one The title compound was prepared and purified as described in Example 29A, substituting 1-(2-aminoethyl)piperidin-2-one hydrochloride (Matrix Scientific) for (S)-tert-butyl 2-(aminomethyl)pyrrolidine-1-carboxylate. MS (DCI/NH$_3$) m/z 282 (M+H)$^+$.

Example 39B

N-[(2Z)-5-tert-butyl-3-[2-(2-oxopiperidin-1-yl)ethyl]-1,3-thiazol-2(3H)-ylidene]-5-chloro-2-methoxybenzamide The title compound was prepared and purified as described in Example 29B, substituting Example 39A for Example 29A. $^1$H NMR (300 MHz, CDCl$_3$) δ ppm 1.34 (s, 9 H) 1.64-1.77 (m, 4 H) 2.36 (t, J=6.27 Hz, 2 H) 3.15 (t, J=5.43 Hz, 2 H) 3.77 (t, J=6.44 Hz, 2 H) 3.91 (s, 3 H) 4.40 (t, J=6.27 Hz, 2 H) 6.92 (d, J=9.16 Hz, 1 H) 7.34 (dd, J=8.82, 3.05 Hz, 1 H) 8.03 (d, J=3.05 Hz, 1 H); MS (DCI) m/z 450 (M+H)$^+$. Anal. Calculated for C$_{22}$H$_{28}$ClN$_3$O$_3$S.0.8H$_2$O: C, 56.91; H, 6.42; N, 9.05. Found: C, 57.31; H, 6.33; N, 8.65.

Example 40

N-[(2Z)-5-tert-butyl-3-[2-(2-oxoimidazolidin-1-yl-ethyl]-1,3-thiazol-2(3H)-ylidene]-5-chloro-2-methoxybenzamide

Example 40A 1-(2-(5-tert-butyl-2-iminothiazol-3(2H)-yl)ethyl)imidazolidin-2-one The title compound was prepared and isolated as described in Example 29A, substituting 1-(2-aminoethyl)imidazolidin-2-one (Matrix Scientific) for (S)-tert-butyl 2-(aminomethyl)pyrrolidine-1-carboxylate. MS (DCI/NH$_3$) m/z 269 (M+H)$^+$.

Example 40B

N-[(2Z)-5-tert-butyl-3-[2-(2-oxoimidazolidin-1-yl)ethyl]-1,3-thiazol-2(3H)-ylidene]-5-chloro-2-methoxybenzamide The title compound was prepared as described in Example 29B, substituting Example 40A for Example 29A, and purified by reverse phase HPLC using a Waters Sunfire C8 column (30×75 mm) eluting with a gradient of acetonitrile and 0.1% trifluoroacetic acid in water at a flow rate of 50 mL/min. Fractions selected by mass spectrometry and concentrated to provide the title compound as a trifluoroacetic acid salt. $^1$H NMR (300 MHz, CDCl$_3$) δ ppm 1.40 (s, 9 H) 3.42-3.50 (m, 2 H) 3.54-3.63 (m, 2 H) 3.72 (t, J=6.27 Hz, 2 H) 3.96-4.00 (m, 3 H) 4.60 (t, J=6.10 Hz, 2 H) 6.99 (d, J=8.82 Hz, 1 H) 7.18 (s, 1 H) 7.49 (dd, J=8.82, 2.71 Hz, 1 H) 7.96 (d, J=2.71 Hz, 1 H); MS (DCI) m/z 437 (M+H)$^+$. Anal. Calculated for C$_{20}$H$_{25}$ClN$_4$O$_3$S.2.4TFA.1H$_2$O: C, 40.88; H, 4.07; 7.69. Found: C, 41.16; H, 3.78; N, 7.37.

Example 41

(Z)—N-(5-tert-butyl-3-(2-sulfamoylethyl)thiazol-2(3H)-ylidene)-2-methoxy-5-(trifluoromethyl)benzamide

Example 41A 2-(5-tert-butyl-2-iminothiazol-3(2H)-yl)ethanesulfonamide

A mixture of 3,3-dimethylbutanal (2.15 mL, 17.1 mmol), triethylamine (2.2 mL, 15.6 mmol), 2-aminoethanesulfonamide-hydrochloric acid (2.5 g, 15.6 mmol), and 4 g of 4 Å molecular sieves (8-12 mesh beads) in acetonitrile (40 mL) was stirred at ambient temperature for 20 h. This material was filtered through Celite with acetonitrile (additional 25 mL) then potassium thiocyanate (2.0 g, 20.7 mmol) was added and the mixture was warmed to 50° C. Iodine (3.95 g, 15.6 mmol) was added and the mixture was stirred at 50° C. for 16 h then was cooled to ambient temperature. The mixture was stirred with 50 mL of 20% aqueous sodium metabisulfite for 1 h then the layers were separated and the aqueous layer was extracted with CH$_2$Cl$_2$ (3×10 mL). The combined organics were dried over anhydrous Na$_2$SO$_4$, filtered, and concentrated under reduced pressure to give the crude title compound (0.5 g, 1.9 mmol, 12.2% yield) which was carried on without further purification. MS (DCI/NH$_3$) m/z 264 (M+H)$^+$.

Example 41B (Z)—N-(5-tert-butyl-3-(2-sulfamoylethyl)thiazol-2(3H)-ylidene)-2-methoxy-5-(trifluoromethyl)benzamide To a solution of Example 41A (0.5 g, 1.9 mmol) in tetrahydrofuran (20 mL) was added triethylamine (0.80 mL, 5.7 mmol) followed by Example 1B (0.48 g, 2.0 mmol). This mixture was warmed to 50° C. and was allowed to stir for 16 h. The mixture was cooled to ambient temperature and was quenched with saturated, aqueous NH$_4$Cl. The layers were separated and the aqueous layer was extracted with ethyl acetate (3×5 mL). The combined organics was dried over anhydrous Na$_2$SO$_4$, filtered, and concentrated under reduced pressure. The crude material was purified by column chromatography (SiO$_2$, 60% hexanes in ethyl acetate) to give the title compound (0.27 g, 0.58 mmol, 31% yield). $^1$H NMR (300 MHz, CD$_3$OD) δ ppm 1.39 (s, 9 H), 3.69 (t, J=6.4 Hz, 2 H), 3.96 (s, 3 H), 4.66 (t, J=6.6 Hz, 2 H), 7.20 (s, 1 H), 7.25 (d, J=8.8 Hz, 1 H), 7.73 (ddd, J=8.8, 2.4, 0.7 Hz, 1 H), 8.16 (d, J=2.4 Hz, 1 H); MS (DCI/NH$_3$) m/z 466 (M+H)$^+$; Anal. calculated for C$_{18}$H$_{22}$F$_3$N$_3$O$_4$S$_2$: C, 46.44; H, 4.76; N, 9.03. Found: C, 46.38; H, 4.55; N, 8.93.

Example 42

N-[(2Z)-5-tert-butyl-3-{[1-(methylsulfonyl)azetidin-3-yl]methyl}-1,3-thiazol-2(3H)-ylidene]-2-{[(2S)-1-methylpyrrolidin-2-yl]methoxy}-5-(trifluoromethyl)benzamide

Example 42A tert-butyl 3-((5-tert-butyl-2-iminothiazol-3(2H)-yl)methyl)azetidine-1-carboxylate A mixture of 3,3-dimethylbutanal (3.7 mL, 30 mmol), tert-butyl 3-(aminomethyl)azetidine-1-carboxylate (Astatech, 5 g, 27 mmol), and 8 g of 4 Å molecular sieves (8-12 mesh beads) in acetonitrile (50 mL) was stirred at ambient temperature for 72 h. The material was filtered through Celite with acetonitrile (additional 25 mL) then potassium thiocyanate (3.5 g, 35 mmol) was added and the mixture was warmed to 50° C. Iodine (6.8 g, 26.8 mmol) was added and the mixture stirred at 50° C. for 16 h then was cooled to ambient temperature. The mixture was stirred with 75 mL of 20% aqueous sodium metabisulfite for 1 h then the layers were separated and the aqueous layer was extracted with 3×10 mL CH$_2$Cl$_2$. The combined organics were dried over anhydrous Na$_2$SO$_4$, filtered, and concentrated under reduced pressure to give the crude title compound (6.3 g, 19 mmol, 72% yield) which was carried on without further purification. MS (DCI/NH$_3$) m/z 326 (M+H)$^+$.

Example 42B (Z)-tert-butyl 3-((5-tert-butyl-2-(2-fluoro-5-(trifluoromethyl)benzoylimino)thiazol-3(2H)-yl)methyl)azetidine-1-carboxylate To a solution of the product of Example 42A (4.1 g, 12.5 mmol) in tetrahydrofuran (40 mL) was added triethylamine (5.2 mL, 37.6 mmol) followed by 2-fluoro-5-(trifluoromethyl)benzoyl chloride (2.0 mL, 13.2 mmol). This mixture was warmed to 50° C. and was allowed to stir for 90 min then the mixture was cooled to ambient temperature and was stirred for 16 h. The mixture was quenched with saturated, aqueous NH₄Cl (20 mL) and diluted with ethyl acetate (20 mL). The layers were separated and the aqueous layer was extracted with ethyl acetate (3×10 mL). The combined organics were dried over anhydrous Na₂SO₄, filtered, and concentrated under reduced pressure. The crude material was purified by column chromatography (SiO₂, 60% hexanes in ethyl acetate) to give the title compound (5.2 g, 10.0 mmol, 80% yield). MS (DCI/NH₃) m/z 516 (M+H)⁺.

Example 42C (Z)—N-(3-(azetidin-3-ylmethyl)-5-tert-butylthiazol-2(3H)-ylidene)-2-fluoro-5-(trifluoromethyl)benzamide A mixture of the product of Example 42B (5.2 g, 10.0 mmol) and trifluoroacetic acid (15.4 mL, 200 mmol) in CH₂Cl₂ (20 mL) was stirred at ambient temperature for 2 h then was concentrated under reduced pressure to give the crude trifluoroacetic acid salt of the title compound. This material was carried on without purification. MS (DCI/NH₃) m/z 416 (M+H)⁺.

Example 42D (Z)—N-(5-tert-butyl-3-((1-(methylsulfonyl)azetidin-3-yl)methyl)thiazol-2(3H)-ylidene)-2-fluoro-5-(trifluoromethyl)benzamide To a solution of the product of Example 42C in tetrahydrofuran (20 mL) was added triethyl amine (5.6 mL, 40.0 mmol) followed by methanesulfonyl chloride (1.6 mL, 20.0 mmol). This mixture was stirred at ambient temperature for 16 h. The mixture was quenched with saturated, aqueous NaHCO₃ (5 mL) and was diluted with ethyl acetate (5 mL). The layers were separated and the aqueous layer was extracted with ethyl acetate (3×5 mL). The combined organics were dried over anhydrous Na₂SO₄, filtered, concentrated under reduced pressure and purified via column chromatography (SiO₂, 50% hexanes/ethyl acetate then 100% ethyl acetate then 9:1:0.1 ethyl acetate:methanol:triethyl amine) to give the title compound (3.2 g, 6.5 mmol, 65% yield). MS (DCI/NH₃) m/z 494 (M+H)⁺.

Example 42E

N-[(2Z)-5-tert-butyl-3-{[1-(methylsulfonyl)azetidin-3-yl]methyl}-1,3-thiazol-2(3H)-ylidene]-2-{[(2S)-1-methylpyrrolidin-2-yl]methoxy}-5-(trifluoromethyl)benzamide To a solution of (S)-(1-methylpyrrolidin-2-yl)methanol (0.36 mL, 3.0 mmol) in tetrahydrofuran (15 mL) at ambient temperature was added potassium tert-butoxide (0.51 g, 4.5 mmol). The mixture was stirred at ambient temperature for 20 min then the product of Example 42D (0.74 g, 1.5 mmol) in 5 mL tetrahydrofuran was added via cannula. The mixture was stirred for 3 h at ambient temperature then was quenched with saturated, aqueous NaHCO₃ (10 mL) and diluted with ethyl acetate (10 mL). The layers were separated and the aqueous layer was extracted with ethyl acetate (3×10 mL). The combined organics were dried over anhydrous Na₂SO₄, filtered, and concentrated under reduced pressure. The crude material was purified via column chromatography SiO₂ (50% hexanes/ethyl acetate then 100% ethyl acetate then 9:1:0.1 ethyl acetate/methanol/triethyl amine) to give the title compound (0.64 g, 1.1 mmol, 73% yield). ¹H NMR (300 MHz, CDCl₃) δ ppm 1.36 (s, 9 H) 1.63-1.93 (m, 3 H) 2.18-2.37 (m, 1 H) 2.47 (s, 3 H) 2.74-2.86 (m, 1 H) 2.82 (s, 3 H) 3.02-3.14 (m, 1 H) 3.16-3.34 (m, 1 H) 3.81 (dd, J=8.1, 5.8 Hz, 2 H) 3.93-4.19 (m, 5 H) 4.39 (d, J=7.5 Hz, 2 H) 6.62 (s, 1 H) 7.04 (d, J=8.7 Hz, 1 H) 7.60 (dd, J=8.3, 2.4 Hz, 1 H) 8.10 (d, J=2.4 Hz, 1 H); MS (DCI/NH₃) m/z 589 (M+H)⁺; Anal. calculated for C₂₆H₃₅F₃N₄O₄S₂: Calc: C, 53.04; H, 5.99; N, 9.52. Found: 53.13; H, 5.96; N, 9.42.

Example 43

5-chloro-2-methoxy-N-[(2Z)-5-methyl-3-{3-[(methylsulfonyl)amino]propyl}-1,3-thiazol-2(3H)-ylidene]benzamide Example 43A tert-butyl 3-(2-imino-5-methylthiazol-3(2H)-yl)propylcarbamate A mixture of 2-amino-5-methylthiazole (0.58 g, 5.0 mmol) and 3-(Boc-amino)propyl bromide (1.2 g, 5.0 mmol) was warmed to 85° C. and was allowed to stir for 4 h. The mixture was cooled to ambient temperature and was purified via column chromatography (SiO₂, 9:1:0.1 CH₂Cl₂:methanol:ammonium hydroxide) to give the title compound (0.96 g, 3.5 mmol, 70% yield). MS (DCI/NH₃) m/z 272 (M+H)⁺.

Example 43B (Z)-tert-butyl 3-(2-(5-chloro-2-methoxybenzoylimino)-5-methylthiazol-3(2H)-yl)propylcarbamate To a solution of the product of Example 43A (0.96 g, 3.5 mmol) in tetrahydrofuran (25 mL) was added triethylamine (1.5 mL, 10.6 mmol) followed by Example 3D in tetrahydrofuran (5 mL) via cannula. This mixture was warmed to 50° C. and was allowed to stir for 4 h. The mixture was cooled to ambient temperature and was quenched with saturated, aqueous NH₄Cl (5 mL). The layers were separated and the aqueous layer was extracted with ethyl acetate (3×5 mL). The combined organics were dried over anhydrous Na₂SO₄, filtered, and concentrated under reduced pressure. The crude material was purified by column chromatography (SiO₂, 60% hexanes in ethyl acetate) to give the title compound (1.0 g, 2.3 mmol, 65% yield). MS (DCI/NH₃) m/z 440 (M+H)⁺.

Example 43C (Z)—N-(3-(3-aminopropyl)-5-methylthiazol-2(3H)-ylidene)-5-chloro-2-methoxybenzamide To the product of Example 43B (0.95 g, 2.2 mmol) in CH₂Cl₂ at 0° C. was added trifluoroacetic acid (10 mL). This mixture was stirred at 0° C. for 5 min then was allowed to warm to ambient temperature and was stirred for 1 h. The material was concentrated under reduced pressure and was purified via column chromatography (SiO₂, 9:1:0.1 CH₂Cl₂: methanol:ammonium hydroxide) to give the title compound (0.40 g, 1.2 mmol, 54% yield). MS (DCI/NH₃) m/z 340 (M+H)⁺.

Example 43D 5-chloro-2-methoxy-N-[(2Z)-5-methyl-3-{3-[(methylsulfonyl)amino]propyl}-1,3-thiazol-2(3H)-ylidene]benzamide To the product of Example 43C (0.22 g, 0.65 mmol) in tetrahydrofuran (7 mL) was added triethyl amine (0.27 mL, 1.9 mmol) followed by methanesulfonyl chloride (75 µL, 0.97 mmol). This mixture was stirred at ambient temperature for 3 h then was quenched with saturated, aqueous NH$_4$Cl (5 mL) and was diluted with ethyl acetate (5 mL). The layers were separated and the aqueous layer was extracted with ethyl acetate (3×5 mL). The combined organics were dried over anhydrous Na$_2$SO$_4$, filtered, concentrated under reduced pressure and purified via column chromatography (SiO$_2$, 10% hexanes in ethyl acetate) to give the title compound (0.12 g, 0.29 mmol, 44% yield). $^1$H NMR (300 MHz, CD$_3$OD) δ ppm 2.02-2.13 (m, 2 H) 2.34 (d, J=1.4 Hz, 3 H) 2.81 (s, 3 H) 3.08 (t, J=6.6 Hz, 2 H) 3.87 (s, 3 H) 4.34 (t, J=6.8 Hz, 2 H) 7.08 (d, J=9.2 Hz, 1 H) 7.15 (q, J=1.2 Hz, 1 H) 7.40 (dd, J=9.0, 2.9 Hz, 1 H) 7.81 (d, J=2.7 Hz, 1 H); MS (DCI/NH$_3$) m/z 418 (M+H)$^+$; Anal. calculated for C$_{16}$H$_{20}$ClN$_3$O$_4$S$_2$: Calc: C, 45.98; H, 4.82; N, 10.05. Found: 46.00; H, 4.98; N, 9.98.

Example 44

5-chloro-2-methoxy-N-[(2Z)-5-methyl-3-[2-(4-methyl-1,3-thiazol-5-yl)ethyl]-1,3-thiazol-2(3H)-ylidene]benzamide

Example 44A 5-methyl-3-(2-(4-methylthiazol-5-yl)ethyl)thiazol-2(3H)-imine

To a solution of 4-methyl-5-thiazoleethanol (2 mL, 16.7 mmol) in CH$_2$Cl$_2$ (10 mL) and pyridine (10 mL) was added p-toluenesulfonyl chloride (3.5 g, 18.4 mmol) portionwise over 15 min. This mixture was stirred at ambient temperature for 18 h then was quenched with 5% aqueous HCl (15 mL). The layers were separated and the aqueous layer was extracted with CH$_2$Cl$_2$ (3×10 mL). The combined organics were dried over anhydrous Na$_2$SO$_4$, filtered, concentrated under reduced pressure and purified via column chromatography (SiO$_2$, 50% hexanes/ethyl acetate) to give 2-(4-methylthiazol-5-yl)ethyl 4-methylbenzenesulfonate (3.24 g, 10.9 mmol, 65% yield). MS (DCI/NH$_3$) m/z 298 (M+H)$^+$.

A mixture of 2-(4-methylthiazol-5-yl)ethyl 4-methylbenzenesulfonate (3.23 g, 10.9 mmol), 2-amino-5-methylthiazole (1.25 g, 10.9 mmol) and tetrabutyl ammonium iodide (2 g, 5.4 mmol) in N,N-dimethylformamide (2 mL) was warmed to 85° C. and was stirred for 18 h. The mixture was cooled to ambient temperature, was diluted with CH$_2$Cl$_2$ (10 mL) and was quenched with 10% NaOH (5 mL). The layers were separated and the aqueous layer was extracted with CH$_2$Cl$_2$ (3×5 mL). The combined organics were dried over anhydrous Na$_2$SO$_4$, filtered, concentrated under reduced pressure and purified via column chromatography (SiO$_2$, 10% methanol in ethyl acetate then 9:1:0.1 CH$_2$Cl$_2$:methanol:ammonium hydroxide) to give the title compound (1.34 g, 5.6 mmol, 51% yield). MS (DCI/NH$_3$) m/z 240 (M+H)$^+$.

Example 44B 5-chloro-2-methoxy-N-[(2Z)-5-methyl-3-[2-(4-methyl-1,3-thiazol-5-yl)ethyl]-1,3-thiazol-2(3H)-ylidene]benzamide To a solution of the product of Example 44A (0.23 g, 0.97 mmol) in tetrahydrofuran (5 mL) was added triethylamine (0.40 mL, 2.9 mmol) followed by Example 3D in tetrahydrofuran (5 mL) via cannula. This mixture was warmed to 50° C. and was allowed to stir for 4 h. The mixture was cooled to ambient temperature and was quenched with saturated, aqueous NH$_4$Cl (5 mL). The layers were separated and the aqueous layer was extracted with ethyl acetate (3×5 mL). The combined organics were dried over anhydrous Na$_2$SO$_4$, filtered, and concentrated under reduced pressure. The crude material was purified by column chromatography (SiO$_2$, 60% hexanes in ethyl acetate) to give the title compound (0.25 g, 0.61 mmol, 63% yield). $^1$H NMR (300 MHz, CD$_3$OD) δ ppm 2.27 (s, 3 H) 2.29 (d, J=1.4 Hz, 3 H) 3.40 (t, J=6.8 Hz, 2 H) 3.85 (s, 3 H) 4.43 (t, J=6.8 Hz, 2 H) 6.94-6.99 (m, 1 H) 7.07 (d, J=9.2 Hz, 1 H) 7.41 (dd, J=9.0, 2.9 Hz, 1 H) 7.84 (d, J=3.1 Hz, 1 H) 8.73 (s, 1 H); MS (DCI/NH$_3$) m/z 408 (M+H)$^+$; Anal. calculated for C$_{18}$H$_{18}$ClN$_3$O$_2$S: Calc: C, 53.00; H, 4.45; N, 10.30. Found: 52.92; H, 4.32; N, 10.15.

Example 45

2-[(tert-butylamino)oxy]-N-[(2Z)-5-tert-butyl-3-{[(2S)-5-oxopyrrolidin-2-yl]methyl}-1,3,4-thiadiazol-2(3H)-ylidene]-5-(trifluoromethyl)benzamide

Example 45A

N-(5-tert-butyl-1,3,4-thiadiazol-2-yl)-2-fluoro-5-(trifluoromethyl)benzamide

To a solution of 5-tert-butyl-1,3,4-thiadiazol-2-amine (1.57 g, 10 mmol) and 2-fluoro-5-(trifluoromethyl)benzoyl chloride (2.27 g, 10 mmol) in CH$_2$Cl$_2$ (45 mL) at 0° C. was added dropwise triethylamine (1.7 mL, 12 mmol) and the reaction mixture was allowed to warm to ambient temperature for 12 h. The mixture was then washed with water, brine, dried with MgSO$_4$, and concentrated under reduced pressure to afford 3.2 g of the title compound. MS (DCI/NH$_3$) m/z 348 (M+H)$^+$.

Example 45B (S,Z)N-(5-tert-butyl-3-((5-oxopyrrolidin-2-yl)methyl)-1,3,4-thiadiazol-2(3H)-ylidene)-2-fluoro-5-(trifluoromethyl)benzamide A mixture of Example 45A (348 mg, 1 mmol), (S)-(5-oxopyrrolidin-2-yl)methyl 4-methylbenzenesulfonate (Aldrich, 673 mg, 2.5 mmol) and potassium carbonate (276 mg, 2 mmol) in toluene (25 mL) was treated with tetrabutylammonium iodide (11 mg, 0.03 mmol), tetrabutylammonium hydrogen sulfate (10 mg, 0.03 mmol) and tetraethylammonium iodide (11 mg, 0.04 mmol) and the resulting mixture was refluxed for 14 h The mixture was cooled to ambient temperature, washed with water, brine, dried with MgSO$_4$, and concentrated under reduced pressure. The residue was purified by chromatography (hexane-ethyl acetate 2:1) to afford 400 mg of the title compound. MS (DCI/NH$_3$) m/z 445 (M+H)$^+$.

Example 45C

2-[(tert-butylamino)oxy]-N-[(2Z)-5-tert-butyl-3-{[(2S)-5-oxopyrrolidin-2-yl]methyl}-1,3,4-thiadiazol-2(3H)-ylidene]-5-(trifluoromethyl)benzamide To a solution of N-tert-butylhydroxylamine [prepared from commercially available t-butylhydroxylamine acetate (Aldrich) by adding saturated sodium bicarbonate solution and extracting the free base with ethyl ether) (461 mg, 5.2 mmol) and Example 45B (1.15 g, 2.6 mmol) in anhydrous tetrahydrofuran (50 mL) was added potassium tert-butoxide (1N solution in tetrahydrofuran) (5.2 mL, 5.2 mmol) and the reaction was left at 40° C. for 15 h. The solvent was removed under reduced pressure and the residue was partitioned between water and ethyl acetate. The organic layer was washed with brine, dried with $MgSO_4$ and concentrated under reduced pressure. The residue was purified by chromatography (hexane-ethyl acetate 1:1) to provide 260 mg of the title compound. $^1$H NMR (300 MHz, DMSO-$d_6$) δ ppm 1.07-1.15 (m, 9 H), 1.39 (s, 9 H), 1.81-1.92 (m, 1 H), 2.05-2.24 (m, 3 H), 4.03-4.14 (m, 1 H), 4.22-4.36 (m, 1 H), 4.39-4.58 (m, 1 H), 7.35 (s, 1 H), 7.70-7.88 (m, 3 H), 8.08 (d, J=2.0 Hz, 1 H); MS (DCI/$NH_3$) m/z 514 (M+H)$^+$. Anal. calculated for $C_{23}H_{30}F_3N_5O_3S \cdot 0.5$ ethyl acetate: C, 53.79; H, 5.89; N, 13.64. Found: C, 53.49; H, 6.15; N, 12.56.

Example 46 tert-butyl 2-[(2Z)-5-tert-butyl-2-[(5-chloro-2-methoxybenzoyl)imino]-1,3-thiazol-3(2H)-yl]ethylcarbamate Example 46A tert-butyl 2-(5-tert-butyl-2-iminothiazol-3(2H)-yl)ethylcarbamate A mixture of tert-butyl 2-aminoethylcarbamate (5.9 g, 37 mmol) and 3,3-dimethylbutanal (4.9 mL 95%, 37 mmol) in 30 mL of dry acetonitrile with 4 g of 4 Å (8-12 mesh beads) molecular sieves was stirred at ambient temperature for 24 hours. The mixture was filtered through Celite and washed with 5 mL of acetonitrile. Potassium thiocyanate (4.8 g, 49 mmol) was added and the mixture warmed to 50° C. for 10 minutes. Iodine (9.3 g, 37 mmol) was added and the reaction stirred at 50° C. for 6 hours. Acetonitrile (30 mL) was added followed by 10 mL of 20% $Na_2S_2O_5$. The layers were separated and the organic layer was dried with $Na_2SO_4$, filtered, and the solvent removed. The residue was chromatographed by equilibrating the column with $CH_2Cl_2$, loading the sample, and eluting with 5% methanol in $CH_2Cl_2$ (0.1% $NH_4OH$) isocratically to afford the title compound (3.5 g, 11.7 mmol, 32% yield). MS (DCI/$NH_3$) m/z 300.2 (M+H)$^+$. $^1$H NMR (300 MHz, CHLOROFORM-D) δ ppm 1.31 (s, 9 H) 1.42 (s, 9 H) 3.57 (q, J=6.78 Hz, 2 H) 4.26 (t, J=6.95 Hz, 2 H) 5.63 (t, J=5.76 Hz, 1 H) 6.58 (s, 1 H).

Example 46B tert-butyl 2-[(2Z)-5-tert-butyl-2-[(5-chloro-2-methoxybenzoyl)imino]-1,3-thiazol-3(2H)-yl]ethylcarbamate Oxalyl chloride (6.5 mL, 2M in $CH_2Cl_2$) was added to 5-chloro-2-methoxybenzoic acid (0.8 g, 4.3 mmol) in 8 mL of $CH_2Cl_2$ followed by 20 μL of N,N-dimethylformamide. The reaction was stirred at ambient temperature for 1 hour. The solvent was removed and the residue dried twice from toluene. The residue was suspended in 5 mL of tetrahydrofuran, Example 46A (1.3 g, 4.3 mmol) was added followed by triethylamine (1.8 mL, 12.9 mmol) and the reaction was stirred at ambient temperature for 1 hour. The reaction mixture was diluted with 100 mL of ethyl acetate, the organic phase was washed with water, brine, dried with $MgSO_4$, filtered, and the solvent removed. The final product was purified by flash chromatography using a gradient from hexane to 75% ethyl acetate in hexane over 750 mL then isocratic for 600 mL to afford the title compound (1.7 g, 3.6 mmol, 85% yield). MS (DCI/$NH_3$) m/z 468.2 (M+H)$^+$. $^1$H NMR (300 MHz, CHLOROFORM-D) δ ppm 1.35 (s, 9 H) 1.39 (s, 9 H) 3.57 (q, J=5.82 Hz, 2 H) 3.90 (s, 3 H) 4.33 (t, J=5.75 Hz, 2 H) 5.41 (s, 1 H) 6.64 (s, 1 H) 6.91 (d, J=9.12 Hz, 1 H) 7.34 (dd, J=8.72, 2.78 Hz, 1 H) 7.93 (d, J=2.78 Hz, 1 H).

Example 47

N-[(2Z)-5-tert-butyl-3-[2-(methylamino)ethyl]-1,3-thiazol-2(3H)-ylidene]-5-chloro-2-methoxybenzamide Example 47A (Z)-tert-butyl 2-(5-tert-butyl-2-(5-chloro-2-methoxybenzoylimino)thiazol-3(2H)-yl)ethyl(methyl)carbamate Example 46B (0.5 g, 1.1 mmol) was dissolved in 4 mL of N,N-dimethylformamide and cooled to 0° C., iodomethane (0.33 mL, 2.2 mmol) was added followed by NaH (60% in mineral oil, 0.056 g, 1.4 mmol). The reaction mixture was allowed to warm to ambient temperature and stir for 1 hour. Ethyl acetate (100 mL) was added and the organic phase was washed with 20% $NH_4Cl$, water, brine, dried with $MgSO_4$, filtered, and the solvent removed to provide the title compound (0.45 g, 0.9 mmol, 87% yield). LCMS m/z 482.2 (M+H)$^+$.

Example 47B

N-[(2Z)-5-tert-butyl-3-[2-(methylamino)ethyl]-1,3-thiazol-2(3H)-ylidene]-5-chloro-2-methoxybenzamide Example 47A (0.45 g, 0.9 mmol) was dissolved in 10 mL of $CH_2Cl_2$, 2 mL of trifluoroacetic acid was added the reaction mixture was stirred at ambient temperature for 90 minutes. The solvent was removed and the residue was twice dissolved in $CH_2Cl_2$ and solvent evaporated. The residue was dissolved in 5% methanol/$CH_2Cl_2$ (0.1% $NH_4OH$), filtered through silica and washed with 5% methanol/$CH_2Cl_2$ (0.1% ammonium hydroxide) and the solvents evaporated to afford the title compound. MS (DCI/$NH_3$) m/z 382.2 (M+H)$^+$. $^1$H NMR (300 MHz, CHLOROFORM-D) δ ppm 1.37 (s, 9 H), 2.54 (s, 3 H), 3.47 (s, 2 H), 3.92 (s, 3 H), 4.54-4.62 (m, 2 H), 6.82 (s, 1 H), 6.98 (d, J=8.82 Hz, 1 H), 7.43 (dd, J=8.81, 2.71 Hz, 1 H), 7.80 (d, J=2.71 Hz, 1 H), 10.89 (s, 1 H).

Example 48

2-(azetidin-3-yloxy)-N-[(2Z)-5-tert-butyl-3-{[1-(methylsulfonyl)azetidin-3-yl]methyl}-1,3-thiazol-2(3H)-ylidene]-5-(trifluoromethyl)benzamide Example 48A (Z)-tert-butyl 3-(2-(5-tert-butyl-3-((1-(methylsulfonyl)azetidin-3-yl)methyl)thiazol-2(3H)-ylidenecarbamoyl)-4-(trifluoromethyl)phenoxy)azetidine-1-carboxylate Potassium t-butoxide (2.0 mL, 1M in tetrahydrofuran) was added to tert-butyl 3-hydroxyazetidine-1-carboxylate (0.37 g, 2.1 mmol) in 0.5 mL of tetrahydrofuran and stirred for 10 minutes. Example 42D (0.5 g, 1.0 mmol) in 2.0 mL of tetrahydrofuran was added and the mixture stirred for 1 hour. The mixture was diluted with ethyl acetate, washed with saturated NaHCO$_3$, water, brine, dried with MgSO$_4$, filtered and the solvent removed under reduced pressure. The residue was chromatographed to afford the title compound (0.58 g, 0.9 mmol, 89% yield). (solvent A=hexane; solvent B=hexane:ethyl acetate:triethylamine (1:3:0.2); 100% solvent A to 100% B over 750 mL then isocratic for 180 mL). MS (DCI/NH$_3$) m/z 647.2 (M+H)$^+$. $^1$H NMR (300 MHz, DMSO-D6) δ ppm 1.33 (s, 9 H), 1.39 (s, 9 H), 2.94 (s, 3 H), 3.76-3.85 (m, 4 H), 3.91 (t, J=8.3 Hz, 2 H), 4.34 (dd, J=9.1, 6.7 Hz, 2 H), 4.40 (d, J=6.7 Hz, 2 H), 5.14 (ddd, J=10.2, 6.4, 4.0 Hz, 1 H), 7.01 (d, J=8.7 Hz, 1 H), 7.45 (s, 1 H), 7.74 (dd, J=8.7, 2.4 Hz, 1 H), 8.01 (d, J=2.4 Hz, 1 H).

Example 48B 2-(azetidin-3-yloxy)-N-[(2Z)-5-tert-butyl-3-{[1-(methylsulfonyl)azetidin-3-yl]methyl}-1,3-thiazol-2(3H)-ylidene]-5-(trifluoromethyl)benzamide Trifluoroacetic acid (1.4 mL 18 mmol) was added to Example 48A (0.58 g, 0.9 mmol) in 6.0 mL of dichloromethane and stirred for 1 hour. Solvent was removed under reduced pressure and the residue dissolved in ethyl acetate, washed with saturated NaHCO$_3$, water, brine, the organic layer dried with MgSO$_4$, filtered, and the solvent removed under reduced pressure. The residue was purified by flash chromatography to afford the title compound. (solvent A=hexane:ethyl acetate:triethylamine (1:3:0.2); solvent B=hexane:ethyl acetate:MeOH:triethylamine (1:3:2:0.2); 100% solvent A to 100% solvent B over 300 mL then isocratic for 600 mL). Pooled fractions were concentrated (0.14 g, 0.26 mmol, 29% yield), the residue was dissolved in 3 mL of ethyl acetate, 65 mg of p-toluene sulfonic acid hydrate dissolved in 1 mL of ethyl acetate was added, then 1 mL of hexane. The solution was cooled in the refrigerator overnight. The next day the solution was filtered, the precipitate was washed with hexane, diethyl ether, then dried under vacuum to provide the title compound as the bis-para-toluene sulfonate salt (75 mg). MS (ESI$^+$) m/z 547.1 (M+H)$^+$. $^1$H NMR (500 MHz, PYRIDINE-d$_5$) δ ppm 1.27 (s, 9 H), 3.11 (s, 3 H), 3.23-3.35 (m, 1 H), 4.06-4.18 (m, 4 H), 4.66 (d, J=7.0 Hz, 2 H), 4.73 (dd, J=11.9, 4.9 Hz, 2 H), 5.15 (dd, J=12.1, 6.6 Hz, 2 H), 5.70-5.77 (m, 1 H), 7.07 (d, J=8.5 Hz, 1 H), 7.34 (s, 1 H), 7.64 (dd, J=8.5, 2.1 Hz, 1 H), 8.56 (d, J=2.1 Hz, 1 H). Analytical calculated for C$_{23}$H$_{29}$F$_3$N$_4$O$_4$S$_2$.2C$_7$H$_8$O$_3$S: C, 49.87; H, 5.09; N, 6.29. Found: C, 49.52; H, 5.21; N, 6.31.

Example 49

5-chloro-N-[(2Z)-3-[(2-fluoropyridin-3-yl)methyl]-5-methyl-1,3-thiazol-2(3H)-ylidene]-2-methoxybenzamide Example 49A (2-fluoropyridin-3-yl)methyl methanesulfonate To a solution of (2-fluoropyridin-3-yl)methanol (200 mg, 1.57 mmol) and triethylamine (658 µL, 4.72 mmol) in CH$_2$Cl$_2$ (10 mL) was added methanesulfonyl chloride (269 mg, 2.36 mmol). The reaction mixture was kept at 0° C. for 30 min., poured into water, and the mixture was extracted with CH$_2$Cl$_2$ (2×20 mL). The combined organic layers were dried over anhydrous Na$_2$SO$_4$, filtered, and concentrated under reduced pressure. The product was used without further purification.

Example 49B 5-chloro-N-[(2Z)-3-[(2-fluoropyridin-3-yl)methyl]-5-methyl-1,3-thiazol-2(3H)-ylidene]-2-methoxybenzamide To a solution of Example 18A (100 mg, 0.31 mmol) in N,N-dimethylformamide:tetrahydrofuran (1:2, 20 mL) was added sodium hydride (60% dispersion in mineral oil, 19 mg, 0.46 mmol). The mixture was stirred at room temperature for 15 min. To this mixture was added tetrabutylammonium iodide (5 mg) and Example 49A (201 mg, 1 mmol). The reaction mixture was stirred at 75° C. for 12 hours, cooled, diluted with ethyl acetate (20 mL) and quenched with saturated aqueous NaHCO$_3$ (20 mL). The aqueous layer was extracted with ethyl acetate (2×20 mL). The combined organic layers were washed with water (1×25 mL), dried over anhydrous Na$_2$SO$_4$, filtered, and concentrated under reduced pressure. The residue was purified by column chromatography using an Analogix® Intelliflash280™ (SiO$_2$, 10-100% ethyl acetate in hexanes) to afford 14.5 mg (12%) of the title compound. $^1$H NMR (500 MHz, CHLOROFORM-D) δ ppm 2.33 (s, 3 H) 3.91 (s, 3 H) 5.43 (s, 2 H) 6.89 (s, 1 H) 6.93 (d, J=8.85 Hz, 1 H) 7.24 (ddd, J=4.88, 1.53 Hz, 1 H) 7.38 (dd, J=8.85, 2.75 Hz, 1 H) 7.92 (d, J=2.75 Hz, 1 H) 8.00 (t, J=9.46, 7.63 Hz, 1 H) 8.22 (d, J=4.88 Hz, 1 H); MS (DCI/NH$_3$) m/z 392 (M+H)$^+$.

Example 50

N-[(2Z)-5-tert-butyl-3-{[(2R)-5-thioxopyrrolidin-2-yl]methyl}-1,3-thiazol-2(3H)-ylidene]-5-chloro-2-methoxybenzamide A solution of Example 4D (263 mg, 0.62 mmol) in toluene was treated with Lawesson's reagent (151 mg, 0.373 mmol) and the reaction mixture was heated at 80° C. for 6 hours. The reaction mixture was cooled to room temperature, and diluted with ethyl acetate, washed with a 10% solution of sodium bicarbonate, brine, dried (anhydrous MgSO$_4$), filtered, and concentrated under reduced pressure. Purification of the residue by column chromatography (1:1 Hexane-ethyl acetate) provided the title compound (73 mg, 26% yield). $^1$H NMR (300 MHz, DMSO-d$_6$) δ ppm 1.23-1.42 (m, 9 H), 1.87-2.04 (m, 1 H), 2.04-2.30 (m, 1 H), 2.56-2.81 (m, 1 H), 3.78 (s, 3 H), 3.91-4.17 (m, 2 H), 4.34-4.65 (m, 2 H), 7.05-7.16 (m, 1 H), 7.16-7.27 (m, 1 H), 7.44 (dd, J=9.0, 2.9 Hz, 1 H), 7.66 (d, J=2.7 Hz, 1 H), 10.34 (s, 1 H). MS (DCI$^+$) m/z 438 (M+H)$^+$.

Example 51

N-[(2Z)-5-tert-butyl-3-{[(2R)-5-thioxopyrrolidin-2-yl]methyl}-1,3,4-thiadiazol-2(3H)-ylidene]-5-chloro-2-methoxybenzamide Example 7 and Lawesson's reagent were processed according to the procedure described in Example 50 to provide the title compound (215 mg, 63% yield). $^1$H NMR (300 MHz, CHLOROFORM-D) δ ppm 1.37-1.51 (m, 9 H), 2.06-2.22 (m, 1 H), 2.37-2.60 (m, 1 H), 2.82-2.99 (m, 2 H), 3.94 (s, 3 H), 4.29-4.51 (m, 1 H), 4.66-4.82 (m, 2 H), 6.87-7.00 (m, 1

H), 7.38 (dd, J=9.0, 2.9 Hz, 1 H), 7.93 (d, J=3.1 Hz, 1 H), 8.53 (s, 1 H). MS (DCI+) m/z 439 (M+H)+.

Example 52

N-[(2Z)-5-tert-butyl-3-{[(2S)-5-oxopyrrolidin-2-yl]methyl}-1,3,4-thiadiazol-2(3H)-ylidene]-2-methoxy-5-(trifluoromethyl)benzamide The title compound was prepared according to the procedures described in Example 6, substituting Example 3D with commercially available 5-trifluoromethyl-2-methoxybenzoyl chloride (228 mg, 59% yield). $^1$H NMR (300 MHz, DMSO-$d_6$) δ ppm 1.35-1.46 (m, 9 H), 2.01-2.22 (m, 2 H), 2.74 (t, J=6.9 Hz, 2 H), 3.87 (s, 3 H), 4.07-4.22 (m, 1 H), 4.23-4.38 (m, 1 H), 4.40-4.56 (m, 1 H), 7.30 (d, J=8.7 Hz, 1 H), 7.71-7.93 (m, 2 H), 8.57 (d, J=7.1 Hz, 1 H). MS (DCI+) m/z 457 (M+H)+ Anal. Calculated for $C_{20}H_{23}F_3N_4O_3S$: C, 52.62; H, 5.08; N, 12.27. Found: C, 52.71; H, 5.07; N, 11.71.

Example 53

N-[(2Z)-5-tert-butyl-3-{[(2R)-5-oxopyrrolidin-2-yl]methyl}-1,3,4-thiadiazol-2(3H)-ylidene]-2-methoxy-5-(trifluoromethyl)benzamide The title compound was prepared according to the procedures described in Example 7, substituting Example 3D with commercially available 5-trifluoromethyl-2-methoxybenzoyl chloride (230 mg, 60% yield). $^1$H NMR (300 MHz, DMSO-$d_6$) δ ppm 1.36-1.46 (m, 9 H), 1.99-2.21 (m, 2 H), 2.74 (t, J=7.0 Hz, 2 H), 3.87 (s, 3 H), 4.05-4.19 (m, 1 H), 4.24-4.38 (m, 1 H), 4.40-4.61 (m, 1 H), 7.30 (d, J=8.5 Hz, 1 H), 7.71-7.86 (m, 2 H), 8.57 (d, J=7.1 Hz, 1 H). MS (DCI+) m/z 457 (M+H)+. Anal. Calculated for $C_{20}H_{23}F_3N_4O_3S$: C, 52.62; H, 5.08; N, 12.27. Found: C, 52.73; H, 5.07; N, 11.86.

Example 54

N-[(2Z)-5-tert-butyl-3-[(1,3-dimethyl-1H-pyrazol-5-yl)methyl]-1,3-thiazol-2(3H)-ylidene]-5-chloro-2-methoxybenzamide The title compound was prepared according to the procedure described in Example 4D, substituting Example 4A with commercially available 5-(chloromethyl)-1,3-dimethyl-1H-pyrazole (165 mg, 45% yield). $^1$H NMR (300 MHz, DMSO-$d_6$) δ ppm 1.28-1.35 (m, 9 H), 2.08 (s, 3 H), 3.78 (d, J=3.4 Hz, 6 H), 5.36 (s, 2 H), 6.02 (s, 1 H), 7.11 (d, J=9.2 Hz, 1 H), 7.35 (s, 1 H), 7.45 (dd, J=8.8, 3.1 Hz, 1 H), 7.64 (d, J=2.7 Hz, 1 H). MS (DCI+) m/z 434 (M+H)+. Anal. Calculated for $C_{21}H_{25}ClN_4O_2S$: C, 58.25; H, 5.82; N, 12.94. Found: C, 58.24; H, 5.69; N, 12.27.

Example 55

N-[(2Z)-5-tert-butyl-3-{[(2S)-5-oxopyrrolidin-2-yl]methyl}-1,3,4-thiadiazol-2(3H)-ylidene]-2-{[(2S)-5-oxopyrrolidin-2-yl]methoxy}-5-(trifluoromethyl)benzamide The title compound was prepared according to the procedure described in Example 45C, substituting N-tert-butylhydroxylamine with commercially available (S)-5-(hydroxymethyl)pyrrolidin-2-one (130 mg, 56% yield). $^1$H NMR (300 MHz, DMSO-$d_6$) δ ppm 1.39 (s, 9 H), 1.77-1.94 (m, 2 H), 2.01-2.22 (m, 5 H), 2.22-2.39 (m, 1 H), 3.91 (dd, J=8.0, 3.9 Hz, 1 H), 3.97-4.16 (m, 4 H), 4.17-4.34 (m, 1 H), 4.46 (dd, J=13.4, 7.6 Hz, 1 H), 7.69 (s, 1 H), 7.80 (dd, J=9.0, 2.2 Hz, 1 H), 7.91-8.04 (m, 2 H) MS (DCI+) m/z 538 (M+H)+.
Anal. Calculated for $C_{24}H_{28}F_3N_5O_4S$: C, 52.37; H, 5.35; N, 12.72. Found: C, 52.29; H, 5.17; N, 12.41.

Example 56

N-[(2Z)-5-tert-butyl-3-{[(2S)-5-oxopyrrolidin-2-yl]methyl}-1,3-thiazol-2(3H)-ylidene]-2-{[(2S)-1-methylpyrrolidin-2-yl]methoxy}-5-(trifluoromethyl)benzamide Example 57 and commercially available (S)-(1-methylpyrrolidin-2-yl)methanol were processed according to the method described in Example 45C to provide the title compound (170 mg, 47% yield). $^1$H NMR (300 MHz, DMSO-$d_6$) δ ppm 1.32 (s, 9 H), 1.49-1.74 (m, 3 H), 1.73-1.95 (m, 2 H), 2.02-2.11 (m, 3 H), 2.16 (q, J=8.7 Hz, 1 H), 2.31 (s, 3 H), 2.57 (dd, J=8.6, 5.9 Hz, 1 H), 2.81-3.01 (m, 1 H), 3.97-4.16 (m, 4 H), 4.20-4.43 (m, 1 H), 7.18-7.38 (m, 2 H), 7.73 (dd, J=9.0, 2.2 Hz, 1 H), 7.83-8.00 (m, 2 H). MS (DCI+) m/z 538 (M+H)+. Anal. Calculated for $C_{26}H_{33}F_3N_4O_3S$ C, 56.96; H, 6.14; N, 9.91. Found: C, 56.96; H, 6.14; N, 9.91.

Example 57

N-[(2Z)-5-tert-butyl-3-{[(2S)-5-oxopyrrolidin-2-yl]methyl}-1,3-thiazol-2(3H)-ylidene]-2-fluoro-5-(trifluoromethyl)benzamide The title compound was prepared according to the procedures described in Example 45A and Example 45B, substituting 5-tert-butyl-1,3,4-thiadiazol-2-amine with Example 4B (300 mg, 62% yield). $^1$H NMR (300 MHz, DMSO-$d_6$) δ ppm 1.24-1.42 (m, 9 H), 1.75-1.92 (m, 1 H), 2.00-2.20 (m, 3 H), 4.04-4.23 (m, 2 H), 4.23-4.46 (m, 1 H), 7.35 (s, 1 H), 7.44-7.62 (m, 1 H), 7.81-8.00 (m, 2 H), 8.29 (dd, J=6.4, 2.4 Hz, 1 H). MS (DCI+) m/z 444 (M+H)+.

Example 58

N-[(2Z)-5-tert-butyl-3-{[(2S)-5-oxopyrrolidin-2-yl]methyl}-1,3-thiazol-2(3H)-ylidene]-2-(pyridin-2-ylmethoxy)-5-(trifluoromethyl)benzamide Example 57 and commercially available pyridin-2-ylmethanol were processed according to the method described in Example 45C to provide the title compound (185 mg, 38% yield). $^1$H NMR (300 MHz, DMSO-$d_6$) δ ppm 1.24-1.42 (m, 9 H), 1.66-1.84 (m, 1 H), 1.88-2.13 (m, 3 H), 3.93-4.14 (m, 2 H), 4.16-4.37 (m, 1 H), 5.36 (s, 2 H), 7.22-7.40 (m, 3 H), 7.61 (d, J=7.9 Hz, 1 H), 7.68-7.92 (m, 3 H), 8.00 (d, J=2.4 Hz, 1 H), 8.57 (d, J=4.0 Hz, 1 H). MS (DCI+) m/z 533 (M+H)+. Anal. Calculated for $C_{26}H_{27}F_3N_4O_3S \cdot 0.5H_2O$: C, 57.66; H, 5.21; N, 10.34. Found: C, 57.55; H, 5.15; N, 10.43.

Example 59

N-[(2Z)-3-[(2R)-2-aminopropyl]-5-tert-butyl-1,3-thiazol-2(3H)-ylidene]-5-chloro-2-methoxybenzamide Example 59A (R)-tert-butyl 2-methylaziridine-1-carboxylate To a solution of (R)-tert-butyl 1-hydroxypropan-2-ylcarbamate (756 mg, 4.31 mmol) and 4-methylbenzene-1-sulfonyl chloride (905 mg, 4.75 mmol) in ethyl ether (30 mL) was added powdered potassium hydroxide (968 mg, 17.26 mmol) and reaction was refluxed for 2 hr. The reaction mixture was poured into a separatory funnel that contained crushed ice and extracted with ether (2×20 mL). The organics were combined, dried with sodium sulfate, filtered, and concentrated. $^1$H NMR (300 MHz, DMSO-d$_6$) δ ppm 1.16 (d, J=5.43 Hz, 3 H) 1.38 (s, 9 H) 1.83 (d, J=3.73 Hz, 1 H) 2.17 (d, J=5.76 Hz, 1 H) 2.40 (qd, J=5.65, 3.73 Hz, 1 H).

Example 59B (R,Z)-tert-butyl 1-(5-tert-butyl-2-(5-chloro-2-methoxybenzoylimino)thiazol-3(2H)-yl)propan-2-ylcarbamate In a vial, a mixture of Example 4B (70 mg, 0.448 mmol) and Example 59A (225 mg, 1.43 mmol) was heated at 85° C. for 24 hr. The reaction mixture was taken to the next step without further purification.

The above mixture was dissolved in CH$_2$Cl$_2$ (3 mL) and N,N-dimethylformamide (3 mL). N,N-dimethylpyridin-4-amine (109 mg, 0.896 mmol) was added followed by addition of Example 3D (92 mg, 0.448 mmol) and the mixture was stirred for 24 hr. To the reaction was added water and the mixture was extracted with CH$_2$Cl$_2$ (2×10 mL). The organics were combined, washed with H$_2$O, dried (MgSO$_4$), filtered, and concentrated. The residue was triturated with CH$_2$Cl$_2$: hexane (1:2) and the resulting solid was filtered (120 mg, 56%). $^1$H NMR (300 MHz, CHLOROFORM-D) δ ppm 1.23-1.27 (m, 3 H) 1.33-1.35 (m, 18 H) 3.90 (s, 3 H) 4.02-4.16 (m, 2 H) 4.34-4.48 (m, 1 H) 5.73-5.75 (m, 1 H) 6.65-6.70 (m, 1 H) 6.89-6.93 (m, 1 H) 7.33 (dt, J=8.73, 2.58 Hz, 1 H) 7.89-7.96 (m, 1 H); MS (DCI) m/z 482 (M+H)$^+$.

Example 59C

N-[(2Z)-3-[(2R)-2-aminopropyl]-5-tert-butyl-1,3-thiazol-2(3H)-ylidene]-5-chloro-2-methoxybenzamide In a 20 mL vial, to a solution of Example 59B (75 mg, 0.156 mmol) in MeOH (1 mL) was added a solution of hydrogen chloride (0.039 mL, 0.156 mmol) in dioxane and the mixture was stirred for 24 hr. The reaction was concentrated and the residue was purified by preparative HPLC on a Waters Symmetry C8 column (25 mm×100 mm, 7 m particle size) using a gradient of 10-100% acetonitrile (A) and 10 mM ammonium acetate in water (B), at a flow rate of 2.0 mL/min (0-0.1 min 10% A, 0.1-2.6 min 10-100% A, 2.6-2.9 min 100% A, 2.9-3.0 min 100-10% A. 0.5 min post-run delay) to obtain the title compound (32 mg, 59%). $^1$H NMR (300 MHz, METHANOL-d$_4$) δ ppm 1.26 (d, J=6.78 Hz, 3 H) 1.40 (s, 9 H) 3.64-3.73 (m, 1 H) 3.86 (s, 3 H) 4.26-4.31 (m, 2 H) 7.09 (d, J=8.82 Hz, 1 H) 7.18 (s, 1 H) 7.41 (dd, J=8.82, 2.71 Hz, 1 H) 7.74 (d, J=2.71 Hz, 1 H); MS (DCI) m/z 382 (M+H)$^+$.

Example 60

2-[(2Z)-5-tert-butyl-2-[(5-chloro-2-methoxybenzoyl)imino]-1,3-thiazol-3(2H)-yl]ethyl carbamate Example 60A (Z)—N-(5-tert-butyl-3-(2-hydroxyethyl)thiazol-2(3H)-ylidene)-5-chloro-2-methoxybenzamide To a solution of 3,3-dimethylbutanal (5 mL, 39.8 mmol) in acetonitrile (40 mL) were added molecular sieves (1 g) and 2-aminoethanol (2.433 g, 39.8 mmol). The reaction mixture was stirred at room temperature for 48 hr and then filtered. To the filtrate was added potassium thiocyanate (5.15 g, 53.0 mmol). The temperature was adjusted to 50° C. and the mixture was stirred until the solids were dissolved. Then, iodine (10.11 g, 39.8 mmol) was added to the mixture and stirred at 50° C. for 48 hr. The reaction mixture was cooled, concentrated and dissolved in ethyl acetate (50 mL). The solution was washed with sodium meta-bisulfite (20%, 50 mL) by mixing the layers for 30 min. The aqueous layer was isolated. The organic layer was washed twice with HCl (1 N, 50 mL). The aqueous layers were combined and adjusted to pH=9 by adding NH$_4$OH. The product was extracted with ethyl acetate (4×50 mL). The combined organic extracts were dried (Na$_2$SO$_4$), filtered, and concentrated to obtain the crude mixture, which was used without further purification.

To a solution of the above mixture (2.21 g) in CH$_2$Cl$_2$ (20 mL) was added triethylamine (3.08 mL, 22.07 mmol), followed by addition of Example 3D (2.04 g, 9.93 mmol). The reaction was stirred overnight, washed with H$_2$O. The organic layer was separated, dried with Na$_2$SO$_4$, filtered, concentrated and the residue was purified using Analogix® Intelliflash280 ™ (SiO$_2$, 90-30% hexane in ethyl acetate over 25 min) in 18% yield. $^1$H NMR (300 MHz, DMSO-d$_6$) δ ppm 1.32 (s, 9 H) 3.73-3.82 (m, 5 H) 4.20 (t, J=5.35 Hz, 2 H) 4.92-4.99 (m, 1 H) 7.10 (d, J=9.12 Hz, 1 H) 7.24 (s, 1 H) 7.44 (dd, J=8.72, 2.78 Hz, 1 H) 7.62 (d, J=2.78 Hz, 1 H); MS (DCI) m/z 369 (M+H)$^+$.

Example 60B

2-[(2Z)-5-tert-butyl-2-[(5-chloro-2-methoxybenzoyl)imino]-1,3-thiazol-3(2H)-yl]ethyl carbamate To a solution of Example 60A (110 mg, 0.298 mmol) in CH$_2$Cl$_2$ (2 mL) was added trichloroacetyl isocyanate (67.4 mg, 0.358 mmol) and the mixture was stirred for 2 hr. The reaction was concentrated and dissolved in methanol (0.5 mL). A solution of potassium carbonate (140 mg, 1.013 mmol) in water was added and the mixture was stirred for 24 hr. The reaction was concentrated, partitioned between ethyl acetate (3×10 mL) and water (10 mL). The organics were combined, dried, filtered, concentrated and the residue was triturated with CH$_2$Cl$_2$ and hexane (1:3). The solid was collected by filtration (80 mg, 70%). $^1$H NMR (300 MHz, DMSO-d$_6$) δ ppm 1.32 (s, 9 H) 3.79 (s, 3 H) 4.29-4.38 (m, 4 H) 6.55 (s, 1 H) 7.10 (d, J=9.12 Hz, 1 H) 7.19 (s, 1 H) 7.44 (dd, J=9.12, 2.78 Hz, 1 H) 7.67 (d, J=2.78 Hz, 1 H); MS (DCI) m/z 412 (M+H)$^+$. Anal calcd C$_{18}$H$_{22}$ClN$_3$O$_4$S.0.5H$_2$O: C, 51.36; H, 5.51; N, 9.98. Found: C, 51.23; H, 5.33; N, 9.92.

Example 61

2-[(2Z)-2-{[2-azetidin-1-yl-5-(trifluoromethyl)benzoyl]imino}-5-tert-butyl-1,3-thiazol-3(2H)-yl]ethyl azetidine-1-carboxylate Example 61A (Z)—N-(5-tert-butyl-3-(2-hydroxyethyl)thiazol-2(3H)-ylidene)-2-fluoro-5-(trifluoromethyl)benzamide The title compound was prepared as described in Example 60A, substituting 2-fluoro-5-trifluorobenzoyl chloride for Example 3D. $^1$H NMR (300 MHz, DMSO-d$_6$) δ ppm 1.33 (s, 9 H) 3.80 (q, J=5.43 Hz, 2 H) 4.27 (t, J=5.59 Hz, 2 H) 4.94-4.98 (m, 1 H) 7.31 (s, 1 H) 7.48-7.55 (m, 1 H) 7.89-7.96 (m, 1 H) 8.27 (dd, J=6.78, 2.71 Hz, 1 H); MS (DCI) m/z 391 (M+H)$^+$.

Example 61B (Z)-2-(5-tert-butyl-2-(2-fluoro-5-(trifluoromethyl)benzoylimino)thiazol-3(2H)-yl)ethyl carbonochloridate To a solution of Example 61A (300 mg, 0.768 mmol) and triethylamine (233 mg, 2.305 mmol) in Et$_2$O (5 mL) was added activated charcoal (10 mg, 0.768 mmol), followed by addition of bis(trichloromethyl) carbonate (114 mg, 0.384 mmol) and the mixture was stirred for 2 hr. The reaction was filtered, and concentrated to give the title compound as an oil (340 mg, 0.751 mmol, 98%). $^1$H NMR (300 MHz, DMSO-d$_6$) δ ppm 1.33 (s, 9H) 3.80 (t, J=5.43 Hz, 2 H) 4.27 (t, J=5.43 Hz, 2 H) 7.32 (s, 1 H) 7.46-7.56 (m, 1 H) 7.88-7.97 (m, 1 H) 8.24-8.33 (m, 1 H); MS (DCI) m/z 453 (M+H)$^+$.

Example 61C

2-[(2Z)-2-{[2-azetidin-1-yl-5-(trifluoromethyl)benzoyl]imino}-5-tert-butyl-1,3-thiazol-3(2H)-yl]ethyl azetidine-1-carboxylate To a solution of Example 61B (174 mg, 0.384 mmol) in CH$_2$Cl$_2$ (1.4 mL) was added azetidine (110 mg, 1.920 mmol) in methanol (0.5 mL) and the mixture was stirred for 2 hr. The reaction mixture was concentrated and the residue was purified by preparative HPLC on a Waters Symmetry C8 column (25 mm×100 mm, 7 μm particle size) using a gradient of 10-100% acetonitrile (A) and 10 mM ammonium acetate in water (B), at a flow rate of 2.0 mL/min (0-0.1 min 10% A, 0.1-2.6 min 10-100% A, 2.6-2.9 min 100% A, 2.9-3.0 min 100-10% A. 0.5 min post-run delay) to obtain the title compound (38 mg, 0.074 mmol, 19.38%). $^1$H NMR (300 MHz, DMSO-d$_6$) δ ppm 1.32 (m, 9H) 1.99-2.12 (m, 2 H) 2.18-2.29 (m, 2 H) 3.78 (t, J=7.29 Hz, 4 H) 3.87 (t, J=7.46 Hz, 4 H) 4.35 (dd, J=14.24, 4.75 Hz, 4 H) 6.57 (d, J=8.82 Hz, 1 H) 7.27 (s, 1 H) 7.51 (dd, J=8.65, 1.86 Hz, 1 H) 7.87 (d, J=1.70 Hz, 1 H); MS (DCI) m/z 511 (M+H)$^+$.

It is understood that the foregoing detailed description and accompanying examples are merely illustrative and are not to be taken as limitations upon the scope, which is defined solely by the appended claims and their equivalents. Various changes and modifications to the disclosed embodiments will be apparent to those skilled in the art. Such changes and modifications, including without limitation those relating to the chemical structures, substituents, derivatives, intermediates, syntheses, formulations and/or methods of use, may be made without departing from the spirit and scope thereof.

What is claimed is:
1. A compound of formula (I), or a pharmaceutically acceptable salt thereof,

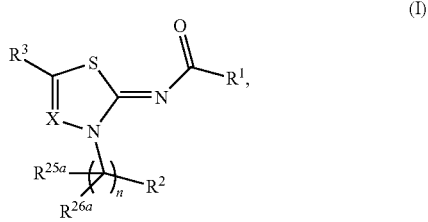

(I)

wherein
X is CR$^4$;
R$^1$ is phenyl or quinolin-8-yl wherein said phenyl is substituted with one group represented by R$^{10}$ and optionally further substituted with 1, 2, or 3 groups represented by R$^{11a}$;
and wherein said quinolin-8-yl is optionally substituted with 1 or 2 groups represented by R$^{11b}$;
R$^2$ is —NR$^{23a}$SO$_2$R$^{105a}$, —NR$^{23b}$COR$^{105b}$, —NR$^{23b}$CO(O)R$^{105b}$, —NR$^{23c}$CONR$^{101a}$R$^{102a}$, —NR$^{23d}$SO$_2$NR$^{101b}$R$^{102b}$, —NR$^{23e}$R$^{24}$, —SO$_2$NR$^{101c}$R$^{102c}$, —OC(O)NR$^{101a}$R$^{102a}$, A$^1$, A$^2$, or A$^3$; with the proviso that when X is CR$^4$, R$^1$ is substituted phenyl, and R$^2$ is —OC(O)NR$^{101a}$R$^{102a}$ wherein R$^{101a}$ and R$^{102a}$ are each independently hydrogen, alkyl, alkoxyalkyl, cycloalkyl, haloalkyl, or haloalkoxyalkyl, then R$^{10}$ is other than haloalkoxyalkoxy, —O—NR$^{23f}$R$^{23g}$, —O—(CR$^{25b}$R$^{26b}$)$_u$-A$^4$, —O—(CR$^{25b}$R$^{26b}$)$_u$—C(=S)NR$^{101d}$R$^{102d}$, —O—(CR$^{25b}$R$^{26b}$)$_u$—C(O)NR$^{101d}$R$^{102d}$, —O—(CR$^{25b}$R$^{26b}$)$_u$—SO$_2$NR$^{101d}$R$^{102d}$, and —O—(CR$^{25b}$R$^{26b}$)$_q$—NR$^{103}$R$^{104}$;
A$^1$ is a monocyclic heterocycle containing 1 or 2 nitrogen atoms and 0 or 1 sulfur atoms, wherein each A$^1$ is independently unsubstituted or substituted with 1, 2, or 3 substituents represented by R$^{21a}$;
A$^2$ is a bicyclic spiroheterocycle containing 1 or 2 nitrogen atoms and 0 or 1 sulfur atoms, wherein each A$^2$ is independently unsubstituted or substituted with 1, 2, or 3 substituents represented by R$^{21b}$;
A$^3$ is imidazolyl, pyrazolyl, pyrrolyl, thiazolyl, thiadiazolyl, isothiazolyl, triazolyl, or pyridinyl, wherein each A$^3$ is independently unsubstituted or substituted with 1, 2, or 3 substituents represented by R$^{22a}$;
R$^3$ is hydrogen, alkyl, alkenyl, alkynyl, cycloalkyl, cycloalkylalkyl, alkoxyalkyl, hydroxyalkyl, haloalkyl, halo, cyano, or cyanoalkyl; with the proviso that when n is 1, R$^1$ is substituted phenyl, X is CR$^4$ wherein R$^4$ is hydrogen, R$^2$ is A$^3$, and A$^3$ is pyridinyl or 1,3-thiazolyl, then R$^3$ is other than hydrogen;
R$^4$ is alkyl, alkenyl, alkynyl, cycloalkyl, hydrogen, or haloalkyl;
R$^{10}$ is alkoxy, alkoxyalkoxy, alkoxyalkyl, alkyl, alkenyl, alkynyl, alkylcarbonyl, cycloalkylalkyl, cyano, cyanoalkyl, formyl, halo, haloalkoxy, haloalkoxyalkoxy, haloalkyl, —CR$^{106a}$(=N—OR$^{106b}$), —O—NR$^{23f}$R$^{23g}$, —O—(CR$^{25b}$R$^{26b}$)$_u$-A$^4$, —O—(CR$^{25b}$R$^{26b}$)$_u$—C(=O)NR$^{101d}$R$^{102d}$, —O—(CR$^{25b}$R$^{26b}$)$_u$—C(=S)NR$^{101d}$R$^{102d}$, —O—(CR$^{25b}$R$^{26b}$)$_u$—SO$_2$NR$^{101d}$R$^{102d}$, —O—(CR$^{25b}$R$^{26b}$)$_q$—NR$^{103}$R$^{104}$, —NR$^{23f}$R$^{23g}$, —NR$^{23f}$—(CR$^{25b}$R$^{26b}$)$_u$-A$^4$, —NR$^{23f}$—(CR$^{25b}$R$^{26b}$)$_u$—C(=O)NR$^{101d}$R$^{102d}$, —NR$^{23f}$—(CR$^{25b}$R$^{26b}$)$_u$—C(=S)NR$^{101d}$R$^{102d}$, —NR$^{23f}$—(CR$^{25b}$R$^{26b}$)$_u$—SO$_2$NR$^{101d}$R$^{102d}$, —NR$^{23f}$—(CR$^{25b}$R$^{26b}$)$_q$—NR$^{103}$R$^{104}$, or A$^4$;
R$^{11a}$ and R$^{11b}$, at each occurrence, are each independently alkoxy, alkyl, alkenyl, alkynyl, alkylcarbonyl, cycloalkyl, cycloalkyloxy, cyano, cyanoalkyl, formyl, halo, haloalkoxy, haloalkoxyalkoxy, haloalkyl, —CR$^{106a}$(=N—OR$^{106b}$), furanyl, oxazolyl, oxadiazolyl, isoxazolyl, triazolyl, pyrazolyl, thiazolyl, oxetanyl, tetrahydrofuranyl, or pyranyl;
R$^{21a}$, R$^{21b}$, R$^{21c}$, and R$^{21d}$, at each occurrence, are each independently alkyl, alkenyl, alkynyl, alkoxy, alkoxyalkoxy, alkoxyalkyl, halo, haloalkyl, haloalkoxy, haloalkoxyalkyl, oxo, =S, hydroxy, cyano, cyanoalkyl, =N—CN, =N—OR$^{106b}$, —CR$^{106a}$(=N—OR$^{106b}$), —CONR$^{101d}$R$^{102d}$, —SO$_2$NR$^{101d}$R$^{102d}$, —COR$^{105d}$, —C(O)OR$^{105c}$, or —SO$_2$R$^{105c}$;

$R^{22a}$ and $R^{22b}$, at each occurrence, are each independently alkyl, alkenyl, alkynyl, alkoxy, alkoxyalkoxy, alkoxyalkyl, halo, haloalkyl, haloalkoxy, haloalkoxyalkyl, hydroxy, cyano, cyanoalkyl, $-CR^{106a}(=N-OR^{106b})$, $-CONR^{101d}R^{102d}$, $-SO_2NR^{101d}R^{102d}$, $-COR^{105d}$, $-C(O)OR^{105c}$, or $-SO_2R^{105c}$;

$R^{23a}$, $R^{23b}$, $R^{23c}$, $R^{23d}$, $R^{23e}$, $R^{23f}$, and $R^{23g}$ are each independently hydrogen, alkyl, cycloalkyl, haloalkyl, alkoxyalkyl, or haloalkoxyalkyl;

$R^{24}$ is alkyl, haloalkyl, alkoxyalkyl, haloalkoxyalkyl, or $A^5$;

$A^4$ and $A^5$, at each occurrence, are each independently a cycloalkyl, a monocyclic heterocycle that is optionally substituted with 1, 2, or 3 substituents represented by $R^{21c}$; a bicyclic spiroheterocycle that is optionally substituted with 1, 2, or 3 substituents represented by $R^{21d}$; or a monocyclic heteroaryl that is optionally substituted with 1, 2, or 3 substituents represented by $R^{22b}$;

$R^{25a}$ and $R^{26a}$, at each occurrence, are each independently hydrogen, alkyl, cyclopropyl, cyclobutyl, cyclopentyl, halo, haloalkyl, or alkoxy; $R^{25a}$ and $R^{26a}$ taken together with the carbon atom to which they are attached optionally form a monocyclic ring selected from the group consisting of cyclopropyl, cyclobutyl, cyclopentyl, and cyclohexyl; wherein each of the cyclopropyl, cyclobutyl, cyclopentyl, and cyclohexyl is independently unsubstituted or substituted with 1, 2, 3, 4, 5, or 6 substituents independently selected from the group consisting of alkyl, halo, haloalkyl, alkoxy, oxo, hydroxy, cyano, and haloalkoxy;

$R^{25b}$ and $R^{26b}$, at each occurrence, are each independently hydrogen, alkyl, cyclopropyl, cyclobutyl, cyclopentyl, halo, haloalkyl, or alkoxy;

$R^{101a}$, $R^{101b}$, $R^{101c}$, $R^{102a}$, $R^{102b}$, and $R^{102c}$, at each occurrence, are each independently hydrogen, alkyl, alkoxyalkyl, cycloalkyl, haloalkyl or haloalkoxyalkyl; $R^{101a}$ and $R^{102a}$, or $R^{101b}$ and $R^{102b}$, or $R^{101c}$ and $R^{102c}$, together with the respective nitrogen atom to which they are attached optionally form a 4-7 membered monocyclic heterocycle; wherein said monocyclic heterocycle contains 0 or 1 additional heteroatom, 0 or 1 double bond, and is optionally substituted with 1, 2, or 3 substituents independently selected from the group consisting of alkyl, alkoxy, haloalkyl, halo, hydroxy, and oxo;

$R^{101d}$ and $R^{102d}$, at each occurrence, are each independently hydrogen, alkyl, alkoxyalkyl, cycloalkyl, haloalkyl or haloalkoxyalkyl; $R^{101d}$ and $R^{102d}$, together with the nitrogen atom to which they are attached, optionally form a 4-7 membered monocyclic heterocycle; wherein said monocyclic heterocycle contains 0 or 1 additional heteroatom, 0 or 1 double bond, and is optionally substituted with 1, 2, or 3 substituents independently selected from the group consisting of alkyl, alkoxy, haloalkyl, halo, hydroxy, and oxo;

$R^{103}$ is hydrogen, alkyl, haloalkyl, or alkoxyalkyl;

$R^{104}$ is hydrogen, alkyl, alkylcarbonyl, alkylsulfonyl, alkoxyalkyl, cycloalkyl, haloalkyl, or haloalkoxyalkyl;

$R^{105a}$, $R^{105b}$, and $R^{105c}$, at each occurrence, are each independently alkyl, cycloalkyl, cycloalkylalkyl, alkoxyalkyl, haloalkyl, or cyanoalkyl;

$R^{105d}$, at each occurrence, is independently hydrogen, alkyl, cycloalkyl, cycloalkylalkyl, alkoxyalkyl, haloalkyl, or cyanoalkyl;

$R^{106a}$ and $R^{106b}$, at each occurrence, are each independently hydrogen, methyl, ethyl, propyl, isopropyl, n-butyl, sec-butyl, isobutyl, tert-butyl, cyclopropyl, or cyclobutyl;

n is 1, 2, 3, or 4;

u is 0, 1, 2, 3, or 4;

q is 2, 3, or 4, and each occurrence of the cycloalkyl, the cycloalkyl moiety of the cycloalkylalkyl and the cycloalkyloxy, the cyclopropyl, the cyclobutyl, and the cyclopentyl, as represented by $R^3$, $R^4$, $R^{10}$, $R^{11a}$, $R^{11b}$, $R^{23a}$, $R^{23b}$, $R^{23c}$, $R^{23d}$, $R^{23e}$, $R^{23f}$, $R^{23g}$, $A^4$, $A^5$, $R^{25a}$, $R^{26a}$, $R^{25b}$, $R^{26b}$, $R^{101a}$, $R^{101b}$, $R^{101c}$, $R^{101d}$, $R^{102a}$, $R^{102b}$, $R^{102c}$, $R^{102d}$, $R^{104}$, $R^{105a}$, $R^{105b}$, $R^{105c}$, $R^{105d}$, $R^{106a}$, and $R^{106b}$, are each independently unsubstituted or substituted with 1, 2, 3, 4, 5, or 6 substituents independently selected from the group consisting of alkyl, halo, haloalkyl, alkoxy, oxo, hydroxy, cyano, and haloalkoxy.

2. The compound of claim 1 having formula (I), or a pharmaceutically acceptable salt thereof, wherein $R^2$ is $-NR^{23a}SO_2R^{105a}$, $-NR^{23b}C(O)OR^{105B}$, $-NR^{23e}R^{24}$, $-SO_2NR^{101c}R^{102c}$, or $-OC(O)NR^{101a}R^{102a}$.

3. The compound of claim 1 having formula (I), or a pharmaceutically acceptable salt thereof, wherein $R^2$ is $A^1$, $A^2$, or $A^3$.

4. The compound of claim 1 having formula (I-A), or a pharmaceutically acceptable salt thereof

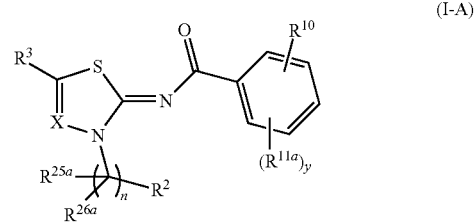

(I-A)

wherein y is 0, 1, 2, or 3.

5. The compound of claim 4 having formula (I-A), or a pharmaceutically acceptable salt thereof wherein $R^2$ is $-NR^{23a}SO_2R^{105a}$, $-NR^{23b}C(O)OR^{105B}$, $-NR^{23e}R^{24}$, $-SO_2NR^{101c}R^{102c}$, or $-OC(O)NR^{101a}R^{102a}$.

6. The compound of claim 4 having formula (I-A), or a pharmaceutically acceptable salt thereof wherein $R^2$ is $-NR^{23a}SO_2R^{105a}$, $-NR^{23b}C(O)OR^{105B}$, $-NR^{23e}R^{24}$, $-SO_2NR^{101c}R^{102c}$, or $-OC(O)NR^{101a}R^{102a}$; and $R^3$ is $C_{1-6}$ alkyl, optionally substituted cycloalkyl, halo, haloalkyl, or hydroxyalkyl.

7. The compound of claim 4 having formula (I-A), or a pharmaceutically acceptable salt thereof wherein $R^2$ is $A^1$, $A^2$, or $A^3$.

8. The compound of claim 4 having formula (I-A), or a pharmaceutically acceptable salt thereof wherein $R^2$ is $A^1$, $R^3$ is $C_{1-6}$ alkyl, optionally substituted cycloalkyl, halo, haloalkyl, or hydroxyalkyl.

9. The compound of claim 4 having formula (I-A), or a pharmaceutically acceptable salt thereof wherein $R^2$ is $A^3$, $R^3$ is $C_{1-6}$ alkyl, optionally substituted cycloalkyl, halo, haloalkyl, or hydroxyalkyl.

10. The compound of claim 1 having formula (I-D), or a pharmaceutically acceptable salt thereof

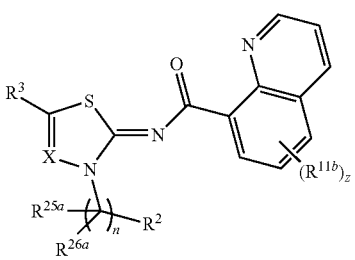

(I-D)

wherein z is 0, 1, or 2.

11. The compound according to claim 1 or a pharmaceutically acceptable salt thereof, selected from the group consisting of N-[(2Z)-5-tert-butyl-3-{[1-(methylsulfonyl)azetidin-3-yl]methyl}-1,3-thiazol-2(3H)-ylidene]-2-methoxy-5-(trifluoromethyl)benzamide;

N-[(2Z)-5-tert-butyl-3-{[1-(cyclopropylsulfonyl)azetidin-3-yl]methyl}-1,3-thiazol-2(3H)-ylidene]-2-methoxy-5-(trifluoromethyl)benzamide;

5-chloro-2-methoxy-N-[(2Z)-5-methyl-3-{[1-(methylsulfonyl)azetidin-3-yl]methyl}-1,3-thiazol-2(3H)-ylidene]benzamide;

N-[(2Z)-5-tert-butyl-3-{[(2R)-5-oxopyrrolidin-2-yl]methyl}-1,3-thiazol-2(3H)-ylidene]-5-chloro-2-methoxybenzamide;

N-[(2Z)-5-tert-butyl-3-{[(2S)-5-oxopyrrolidin-2-yl]methyl}-1,3-thiazol-2(3H)-ylidene]-5-chloro-2-methoxybenzamide;

N-[(2Z)-5-tert-butyl-3-{[1-(methylsulfonyl)azetidin-3-yl]methyl}-1,3-thiazol-2(3H)-ylidene]-5-chloro-2-methoxybenzamide;

N-[(2Z)-5-tert-butyl-3-{2-[methyl(methylsulfonyl)amino]ethyl}-1,3-thiazol-2(3H)-ylidene]-5-chloro-2-methoxybenzamide;

N-[(2Z)-5-tert-butyl-3-[2-(dimethylamino)ethyl]-1,3-thiazol-2(3H)-ylidene]-5-chloro-2-methoxybenzamide;

N-[(2Z)-5-tert-butyl-3-{2-[(methylsulfonyl)amino]ethyl}-1,3-thiazol-2(3H)-ylidene]-5-chloro-2-methoxybenzamide;

N-[(2Z)-5-tert-butyl-3-{2-[(ethylsulfonyl)(methyl)amino]ethyl}-1,3-thiazol-2(3H)-ylidene]-5-chloro-2-methoxybenzamide;

5-chloro-N-[(2Z)-3-[(6-fluoropyridin-3-yl)methyl]-5-methyl-1,3-thiazol-2(3H)-ylidene]-2-methoxybenzamide;

N-[(2Z)-3-[(2R)-azetidin-2-ylmethyl]-5-tert-butyl-1,3-thiazol-2(3H)-ylidene]-5-chloro-2-methoxybenzamide;

5-chloro-N-[(2Z)-5-chloro-3-(1,3-thiazol-4-ylmethyl)-1,3-thiazol-2(3H)-ylidene]-2-methoxybenzamide;

N-[(2Z)-5-bromo-3-(1,3-thiazol-4-ylmethyl)-1,3-thiazol-2(3H)-ylidene]-5-chloro-2-methoxybenzamide;

5-chloro-2-methoxy-N-[(2Z)-5-methyl-3-(1,3-thiazol-4-ylmethyl)-1,3-thiazol-2(3H)-ylidene]benzamide;

2,5-dichloro-N-[(2Z)-5-methyl-3-[(2-methyl-1,3-thiazol-4-yl)methyl]-1,3-thiazol-2(3H)-ylidene]benzamide;

5-chloro-2-methoxy-N-[(2Z)-5-methyl-3-[(2-methyl-1,3-thiazol-4-yl)methyl]-1,3-thiazol-2(3H)-ylidene]benzamide;

5-chloro-2-methoxy-N-[(2Z)-5-methyl-3-(1,3-thiazol-2-ylmethyl)-1,3-thiazol-2(3H)-ylidene]benzamide;

5-chloro-2-methoxy-N-[(2Z)-5-methyl-3-[(4-methyl-1,3-thiazol-2-yl)methyl]-1,3-thiazol-2(3H)-ylidene]benzamide;

5-chloro-N-[(2Z)-3-[(6-chloropyridin-3-yl)methyl]-5-methyl-1,3-thiazol-2(3H)-ylidene]-2-methoxybenzamide;

5-chloro-2-methoxy-N-[(2Z)-5-methyl-3-{[6-(trifluoromethyl)pyridin-3-yl]methyl}-1,3-thiazol-2(3H)-ylidene]benzamide;

N-[(2Z)-5-tert-butyl-3-(1,3-thiazol-4-ylmethyl)-1,3-thiazol-2(3H)-ylidene]-5-chloro-2-methoxybenzamide;

2-ethoxy-N-[(2Z)-5-methyl-3-[3-(1H-pyrrol-1-yl)propyl]-1,3-thiazol-2(3H)-ylidene]benzamide;

5-chloro-2-methoxy-N-[(2Z)-5-methyl-3-[3-(1H-pyrrol-1-yl)propyl]-1,3-thiazol-2(3H)-ylidene]benzamide;

N-[(2Z)-5-tert-butyl-3-[(2S)-pyrrolidin-2-ylmethyl]-1,3-thiazol-2(3H)-ylidene]-5-chloro-2-methoxybenzamide;

N-[(2Z)-5-tert-butyl-3-[(2S)-piperidin-2-ylmethyl]-1,3-thiazol-2(3H)-ylidene]-5-chloro-2-methoxybenzamide;

N-[(2Z)-5-tert-butyl-3-[(2R)-piperidin-2-ylmethyl]-1,3-thiazol-2(3H)-ylidene]-5-chloro-2-methoxybenzamide;

N-[(2Z)-5-tert-butyl-3-{[(2S)-1-methylpyrrolidin-2-yl]methyl}-1,3-thiazol-2(3H)-ylidene]-5-chloro-2-methoxybenzamide;

N-[(2Z)-5-tert-butyl-3-{[(2S)-1-methylpiperidin-2-yl]methyl}-1,3-thiazol-2(3H)-ylidene]-5-chloro-2-methoxybenzamide;

N-[(2Z)-5-tert-butyl-3-{[(2R)-1-methylpiperidin-2-yl]methyl}-1,3-thiazol-2(3H)-ylidene]-5-chloro-2-methoxybenzamide;

N-[(2Z)-5-tert-butyl-3-{[(2R)-1-ethylpiperidin-2-yl]methyl}-1,3-thiazol-2(3H)-ylidene]-5-chloro-2-methoxybenzamide;

N-[(2Z)-5-tert-butyl-3-[(3R)-piperidin-3-ylmethyl]-1,3-thiazol-2(3H)-ylidene]-5-chloro-2-methoxybenzamide;

N-[(2Z)-5-tert-butyl-3-[(2R)-pyrrolidin-2-ylmethyl]-1,3-thiazol-2(3H)-ylidene]-5-chloro-2-methoxybenzamide;

N-[(2Z)-5-tert-butyl-3-[2-(2-oxopyrrolidin-1-yl)ethyl]-1,3-thiazol-2(3H)-ylidene]-5-chloro-2-methoxybenzamide;

N-[(2Z)-5-tert-butyl-3-[2-(2-oxopiperidin-1-yl)ethyl]-1,3-thiazol-2(3H)-ylidene]-5-chloro-2-methoxybenzamide;

N-[(2Z)-5-tert-butyl-3-[2-(2-oxoimidazolidin-1-yl)ethyl]-1,3-thiazol-2(3H)-ylidene]-5-chloro-2-methoxybenzamide;

(Z)—N-(5-tert-butyl-3-(2-sulfamoylethyl)thiazol-2(3H)-ylidene)-2-methoxy-5-(trifluoromethyl)benzamide;

N-[(2Z)-5-tert-butyl-3-{[1-(methylsulfonyl)azetidin-3-yl]methyl}-1,3-thiazol-2(3H)-ylidene]-2-{[(2S)-1-methylpyrrolidin-2-yl]methoxy}-5-(trifluoromethyl)benzamide;

5-chloro-2-methoxy-N-[(2Z)-5-methyl-3-{3-[(methylsulfonyl)amino]propyl}-1,3-thiazol-2(3H)-ylidene]benzamide;

5-chloro-2-methoxy-N-[(2Z)-5-methyl-3-[2-(4-methyl-1,3-thiazol-5-yl)ethyl]-1,3-thiazol-2(3H)-ylidene]benzamide;

tert-butyl 2-[(2Z)-5-tert-butyl-2-[(5-chloro-2-methoxybenzoyl)imino]-1,3-thiazol-3(2H)-yl]ethylcarbamate;

N-[(2Z)-5-tert-butyl-3-[2-(methylamino)ethyl]-1,3-thiazol-2(3H)-ylidene]-5-chloro-2-methoxybenzamide;
2-(azetidin-3-yloxy)-N-[(2Z)-5-tert-butyl-3-{[1-(methylsulfonyl)azetidin-3-yl]methyl}-1,3-thiazol-2(3H)-ylidene]-5-(trifluoromethyl)benzamide;
5-chloro-N-[(2Z)-3-[(2-fluoropyridin-3-yl)methyl]-5-methyl-1,3-thiazol-2(3H)-ylidene]-2-methoxybenzamide;
N-[(2Z)-5-tert-butyl-3-{[(2R)-5-thioxopyrrolidin-2-yl]methyl}-1,3-thiazol-2(3H)-ylidene]-5-chloro-2-methoxybenzamide;
N-[(2Z)-5-tert-butyl-3-[(1,3-dimethyl-1H-pyrazol-5-yl)methyl]-1,3-thiazol-2(3H)-ylidene]-5-chloro-2-methoxybenzamide;
N-[(2Z)-5-tert-butyl-3-{[(2S)-5-oxopyrrolidin-2-yl]methyl}-1,3-thiazol-2(3H)-ylidene]-2-{[(2S)-1-methylpyrrolidin-2-yl]methoxy}-5-(trifluoromethyl)benzamide;
N-[(2Z)-5-tert-butyl-3-{[(2S)-5-oxopyrrolidin-2-yl]methyl}-1,3-thiazol-2(3H)-ylidene]-2-fluoro-5-(trifluoromethyl)benzamide;
N-[(2Z)-5-tert-butyl-3-{[(2S)-5-oxopyrrolidin-2-yl]methyl}-1,3-thiazol-2(3H)-ylidene]-2-(pyridin-2-ylmethoxy)-5-(trifluoromethyl)benzamide;
2-[(2Z)-5-tert-butyl-2-[(5-chloro-2-methoxybenzoyl)imino]-1,3-thiazol-3(2H)-yl]ethyl carbamate; and
2-[(2Z)-2-{[2-azetidin-1-yl-5-(trifluoromethyl)benzoyl]imino}-5-tert-butyl-1,3-thiazol-3(2H)-yl]ethyl azetidine-1-carboxylate.

12. A pharmaceutical composition comprising a therapeutically effective amount of a compound of formula (I) according to claim 1, or a pharmaceutically acceptable salt thereof, in combination with one or more pharmaceutically acceptable carrier.

13. A method for treating pain in a mammal in need of such treatment comprising administering to the mammal a therapeutically effective amount of a compound of formula (I) according to claim 1, or a pharmaceutically acceptable salt thereof.

* * * * *